United States Patent
Bandiera et al.

(10) Patent No.: US 12,391,680 B2
(45) Date of Patent: Aug. 19, 2025

(54) COMPOUNDS AND COMPOSITIONS FOR THE TREATMENT OF CYSTIC FIBROSIS

(71) Applicants: FONDAZIONE ISTITUTO ITALIANO DI TECNOLOGIA, Genoa (IT); ISTITUTO GIANNINA GASLINI, Genoa (IT); FONDAZIONE PER LA RICERCA SULLA FIBROSI CISTICA—ONLUS, Verona (IT)

(72) Inventors: Tiziano Bandiera, Genoa (IT); Fabio Bertozzi, Genoa (IT); Giorgia Zaetta, Genoa (IT); Frederico Sorana, Verona (IT); Emanuela Caci, Verona (IT); Loretta Ferrera, Verona (IT); Nicoletta Pedemonte, Genoa (IT); Luis Juan Vicente Galietta, Genoa (IT)

(73) Assignees: FONDAZIONE ISTITUTO ITALIANO DI TECNOLOGIA, Genoa (IT); ISTITUTO GIANNINA GASLINI, Genoa (IT); FONDAZIONE PER LA RICERCA SULLA FIBROSI CISTICA—ONLUS, Verona (IT)

( * ) Notice: Subject to any disclaimer, the term of this patent is extended or adjusted under 35 U.S.C. 154(b) by 829 days.

(21) Appl. No.: 17/422,598

(22) PCT Filed: Jan. 16, 2020

(86) PCT No.: PCT/IB2020/050350
§ 371 (c)(1),
(2) Date: Jul. 13, 2021

(87) PCT Pub. No.: WO2020/148703
PCT Pub. Date: Jul. 23, 2020

(65) Prior Publication Data
US 2022/0089584 A1 Mar. 24, 2022

(30) Foreign Application Priority Data
Jan. 16, 2019 (IT) .................. 102019000000687

(51) Int. Cl.
*C07D 413/14* (2006.01)
*C07D 413/04* (2006.01)
(52) U.S. Cl.
CPC ......... *C07D 413/14* (2013.01); *C07D 413/04* (2013.01)
(58) Field of Classification Search
CPC ....... C07D 413/14; C07D 413/04; A61P 1/10; A61P 11/00; A61P 27/02
See application file for complete search history.

(56) References Cited

FOREIGN PATENT DOCUMENTS

| CN | 104926804 B | * 1/2019 | ........... C07D 409/12 |
|---|---|---|---|
| WO | 2014/081820 | 5/2014 | |
| WO | 2014/160478 | 10/2014 | |
| WO | 2017/208115 | 12/2017 | |
| WO | 2018/201126 | 11/2018 | |

OTHER PUBLICATIONS

Lopes-Pacheco, M. CFTR Modulators: The Changing Face of Cystic Fibrosis in the Era of Precision Medicine. Front Pharmacol., 2020. vol. 10, 1662: 1-29. Published Feb. 20, 2020 (Year: 2020).*
Patel, S.D. et al. CFTR targeted therapies: recent advances in cystic fibrosis and possibilities in other diseases of the airways. Eur Respir Rev, 2020. vol. 29(156):190068. Published Jun. 16, 2020. (Year: 2020).*
CAS Registry No. 1380686-40-7 (Entered STN Registry on Jul. 3, 2012). (Year: 2012).*
CAS Registry No. 1380816-69-2 (Entered STN Registry on Jul. 3, 2012). (Year: 2012).*
CAS Registry No. 1380817-07-1 (Entered STN Registry on Jul. 3, 2012). (Year: 2012).*
CAS Registry No. 1380823-13-1 (Entered STN Registry on Jul. 3, 2012). (Year: 2012).*
CAS Registry No. 1381150-22-6 (Entered STN Registry on Jul. 4, 2012). (Year: 2012).*
CAS Registry No. 1381150-29-3 (Entered STN Registry on Jul. 4, 2012). (Year: 2012).*
CAS Registry No. 1381152-02-8 (Entered STN Registry on Jul. 4, 2012). (Year: 2012).*
CAS Registry No. 2060627-57-6 (Entered STN Registry on Jan. 27, 2017). (Year: 2017).*
CAS Registry No. 2062077-43-2 (Entered STN Registry on Jan. 27, 2017). (Year: 2017).*

(Continued)

*Primary Examiner* — Jean P Cornet
*Assistant Examiner* — Chihyi Lee
(74) *Attorney, Agent, or Firm* — Lathrop GPM LLP; Malaika O. D. Tyson

(57) ABSTRACT

The present invention relates to compounds of Formula (Ia) or pharmaceutically acceptable salts, hydrates, solvates, clathrates, polymorphs, stereoisomers thereof. It further discloses a pharmaceutical composition comprising compounds of Formula (Ia) and the use of compounds of Formula (Ib), in particular to modulate CFTR protein or ABC protein activities.

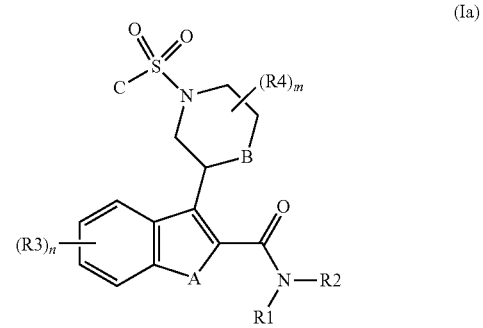

(Ia)

9 Claims, No Drawings

(56) References Cited

OTHER PUBLICATIONS

CAS Registry No. 2061716-26-3 (Entered STN Registry on Jan. 30, 2017). (Year: 2017).*
CAS Registry No. 2061716-09-2 (Entered STN Registry on Jan. 30, 2017). (Year: 2017).*
CAS Registry No. 2061716-02-5 (Entered STN Registry on Jan. 30, 2017). (Year: 2017).*
CAS Registry No. 2061012-48-2 (Entered STN Registry on Jan. 29, 2017). (Year: 2017).*
CAS Registry No. 2061012-23-3 (Entered STN Registry on Jan. 29, 2017). (Year: 2017).*
CAS Registry No. 2060627-68-9 (Entered STN Registry on Jan. 27, 2017). (Year: 2017).*
International Search Report and Written Opinion corresponding to International Patent Application No. PCT/IB2020/050350, mailed Feb. 26, 2020.
Stefano Ponzano et al., "A European regulatory perspective on cystic fibrosis: current treatments, trends in drug development and translational challenges for CFTR modulators", European Respiratory Review, vol. 27, No. 148, Apr. 13, 2018, p. 170124, XP055597485.

* cited by examiner

COMPOUNDS AND COMPOSITIONS FOR THE TREATMENT OF CYSTIC FIBROSIS

CROSS-REFERENCE TO RELATED APPLICATIONS

The present application is filed pursuant to 35 U.S.C. 371 as a U.S. National Phase application of International Patent Application No. PCT/IB2020/050350, which was filed Jan. 16, 2020, claiming the benefit of Italian patent application no. 102019000000687 filed on Jan. 16, 2019. The entire text of the aforementioned applications is incorporated herein by reference in its entirety.

TECHNICAL FIELD

The present invention relates to novel compounds to modulate CFTR protein or ABC protein activities, in particular for the treatment of cystic fibrosis.

BACKGROUND ART

Cystic fibrosis is an autosomal recessive genetic disorder caused by mutations of the gene encoding for the cystic fibrosis transmembrane conductance regulator (CFTR). The incidence of the disease among the Caucasian population is 1/2000-3000 newborns, whereas it is much lower among native Africans and Asians. Despite progress in the treatment of cystic fibrosis, there is no cure.

The cystic fibrosis transmembrane conductance regulator (CFTR) gene encodes an epithelial ion channel responsible for aiding in the regulation of salt and water absorption and secretion in various tissues.

Specifically, CFTR is a 1480 amino acid plasma membrane protein that belongs to the superfamily of ATP-binding cassette (ABC) transporters. CFTR structure consists of a cytosolic N-terminus followed by six transmembrane helices, a nucleotide-binding domain (NBD1), a regulatory (R) domain, six additional transmembrane helices, a second nucleotide-binding domain (NBD2), and a cytosolic C-terminus (Riordan, *Annu Rev Biochem* 77:701-726, 2008; Liu, Cell 169:85-95, 2017). The transmembrane helices form a pore permeable to chloride, bicarbonate, iodide, and other anions. Opening of the pore requires the phosphorylation of the R domain by the CAMP-dependent protein kinase A as well as binding of two ATP molecules in two pockets formed by the assembly of NBD1 and NBD2.

CFTR is a CAMP/ATP-modulated anion channel that is expressed in a variety of cells types, and particularly in epithelial cells of various organs including lungs, pancreas, liver, and intestine (Mall and Hartl, *Eur Respir J* 44:1042-1054, 2014). Physiological signals that increase intracellular CAMP levels elicit CFTR activation. In most tissues, opening of CFTR pore leads to chloride and bicarbonate secretion. The sweat gland duct in which CFTR mediates chloride absorption and not secretion represents a notable exception.

In epithelial cells, normal functioning of CFTR is critical for the maintenance of electrolyte transport throughout the body, including respiratory and digestive tissues The important role of CFTR is demonstrated by the severe pathological manifestations occurring in cystic fibrosis (CF), an inherited disease caused by mutations that lead to CFTR loss of function. In the lungs, lack of CFTR-dependent anion secretion impairs mucociliary clearance and innate antimicrobial mechanisms (Collawn and Matalon, *Am J Physiol* 307: L917-L923, 2014). Consequently, the airways become colonized by antibiotic-resistant bacteria that trigger a severe inflammatory response and a progressive loss of respiratory function.

The gene encoding CFTR has been identified and sequenced (see Gregory, R. J. et al. (1990) Nature 347:382-386; Rich, D. P. et al. (1990) Nature 347:358-362; Riordan, J. R. et al. (1989) Science 245:1066-1073). Defects in this gene cause mutations in CFTR protein resulting in cystic fibrosis, the most common fatal genetic disease in humans. Within the general United States population, up to 10 million people carry a single copy of the defective gene without apparent ill effects. In contrast, individuals with two copies of the cystic fibrosis associated gene suffer from the debilitating and fatal effects of cystic fibrosis, including chronic lung disease.

In addition to respiratory disease, cystic fibrosis patients typically suffer from gastrointestinal problems and pancreatic insufficiency. If left untreated, cystic fibrosis results in death. In addition, the majority of males with cystic fibrosis are infertile and fertility is decreased among females with cystic fibrosis. In contrast to the severe effects of two copies of the cystic fibrosis associated gene, individuals with a single copy of the cystic fibrosis associated gene may exhibit increased resistance to dehydration resulting from diarrhea. This heterozygote advantage could explain the relatively high frequency of the cystic fibrosis gene within the population.

Sequence analysis of the CFTR gene of cystic fibrosis patients has revealed a variety of disease causing mutations (Cutting, G. R. et al. (1990) Nature 346:366-369; Dean, M. et al. (1990) Cell 61:863-870; Kerem, B—S. et al. (1989) Science 245:1073-1080; Kerem, B—S. et al. (1990) Proc. Natl. Acad. Sci. USA 87:8447-8451). To date, more than 2000 CF-causing mutations in the cystic fibrosis gene have been identified, involving 6 classes of molecular defects of the protein (Class I: premature stop of CFTR protein synthesis; Class II: defective maturation and intracellular localisation of the CFTR protein; Class III: impaired opening of CFTR pore; Class IV: reduced ability of CFTR pore to translocate anions; Class V: reduced CFTR protein synthesis due to altered RNA splicing; Class VI: reduced stability of CFTR at the plasma membrane leading to accelerated internalization and degradation).

A large majority of mutations have low or very low frequency (Bobadilla et al., *Hum Mutat* 19:575-606, 2002). However, a single mutation, F508del, is present in 50-90% of CF patients. F508del, i.e. loss of phenylalanine at position 508 within NBD1, causes multiple defects to CFTR protein (Okiyoneda et al., *Nat Chem Biol* 9:444-454, 2013). First of all, F508del-CFTR folding and stability are severely impaired. Such problems, which arise from the intrinsic instability of NBD1 and the altered interaction between NBD1 and the cytosolic loop 4, strongly reduce the trafficking of F508del-CFTR to the plasma membrane (trafficking defect). Indeed, mutant CFTR remains trapped in the endoplasmic reticulum (ER) where it is rapidly degraded by the ubiquitin-proteasome system (Lukacs and Verkman, *Trends Mol Med* 18:81-91, 2012). A second defect caused by F508del is the reduction of the open channel probability, i.e. the fraction of time spent by the channel in the open state (gating defect). Furthermore, if moved to the plasma membrane by rescue maneuvers, F508del-CFTR shows also a decreased half-time. Because of such defects, F508del mutation has combined class II, class III, and class VI characteristics.

The trafficking and gating defects can also be caused, often separately, by other CF mutations. For example, G85E, L1077P, A455E, and N1303K, defined as class II mutations, impair CFTR trafficking (Van Goor et al., *J Cyst Fibros* 13:29-36, 2014). Instead, G551D, G1349D, G178R, and G970R, defined as class III mutations, do not affect trafficking but strongly reduce CFTR open time (Yu et al., *J Cyst Fibros* 11:237-245, 2012).

The most prevalent mutation, i.e. the F508del, is associated with a severe disease.

The reduced number of channels in the membrane and the defective gating lead to reduced anion transport across epithelia leading to defective ion and fluid transport.

As discussed above, it is believed that the deletion of residue 508 in CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. This cellular phenomenon of defective ER processing of ABC transporters by the ER machinery has been shown to be the underlying basis not only for cystic fibrosis disease, but for other diseases (Loo et al., *Journal of Bioenergetics and Biomembranes*, 2005, 37, 501-507).

At present, the treatment of lung disorders in cystic fibrosis requires the development of innovative drugs aimed at the concomitant aspects of the disease and, consequently, modulators of the defective CFTR protein, new antibacterials and new anti-inflammatory agents, which can be used in parallel to obtain a synergistic action. Trafficking and gating defects caused by mutations in the CFTR protein are amenable to pharmacological treatment (Veit et al., *Mol Biol Cell* 27:424-433, 2016). Mistrafficking can be targeted with small molecules called correctors. Gating can be improved with so-called potentiators. There have been several attempts to identify potentiators and correctors (Galietta, *Pediatr Drugs* 15:393-402, 2013). The most advanced molecule is VX-770, also known as ivacaftor, developed by Vertex Pharmaceuticals (Van Goor et al., *Proc Natl Acad Sci USA* 106:18825-18830, 2009). Given its high efficacy in clinical trials (Ramsey et al., *N Engl J Med* 365:1663-1672, 2011), VX-770 has been approved for the treatment of patients with G551D and other eight mutations belonging to class III, who represent about 5% of all the cystic fibrosis patients. VX-770 has no significant therapeutic efficacy in patients who are homozygous for the F508del-CFTR mutation, confirming the need for customised treatments for sub-groups of patients suffering from cystic fibrosis depending on the specific CFTR protein molecular defect. For patients with the F508del-CFTR mutation, new molecules functioning as "correctors" of the mutated CFTR protein are under study. The VX-809 molecule, also known as lumacaftor, has been extensively characterized in cell models in vitro. In clinical trials on cystic fibrosis patients with F508del mutation, VX-809 did not show a clear therapeutic benefit (Clancy et al., *Thorax* 67:12-18, 2012). However, the combination of VX-809 and VX-770, commercially named Orkambi, elicited a significant although modest improvement in respiratory function (Wainwright et al., *N Engl J Med* 373:220-231, 2015). Recently, the combination of the corrector tezacaftor (also known as VX-661) with ivacaftor, commercially named Symdeko, has been approved for the treatment of cystic fibrosis patients homozygous for the CFTR F508del mutations and of patients having one copy of F508del-CFTR gene and one copy of a so-called "residual function" mutation CFTR gene. In clinical trials, Symdeko showed safety and efficacy in cystic fibrosis patients, but improvement in lung function is still modest (Taylor-Cousar et al., *N Engl J Med* 377:2013-2023, 2017; Rowe et al., *N Engl J Med* 377:2024-2035, 2017). Briefly, the treatment of cystic fibrosis patients requires different modulators of the mutated CFTR protein, namely "correctors" and/or "potentiators", depending on the mutations of the CFTR gene, which divide the patients into genetically distinct sub-groups, and complementary medicaments with an antibacterial action and an anti-inflammatory action.

Accordingly, there is a need for novel compounds to be used for the treatment of CFTR mediated diseases, which involve CFTR modulator compounds.

DISCLOSURE OF INVENTION

The aim of the present invention is to provide novel compounds acting as CFTR modulators.

The aforementioned objective has been met according to compounds of claim 1, to a pharmaceutical composition of claim 7, to the uses of claims 8 and 9. Preferred embodiments are set out within the dependent claims.

The following paragraphs provide definitions of the various chemical moieties of the compounds according to the invention and are intended to apply uniformly throughout the specification and claims unless an otherwise expressly set out definition provides a broader definition.

The term "alkyl", as used herein, refers to saturated or partially unsaturated aliphatic hydrocarbon groups. Such term includes straight (unbranched) chains or branched chains.

Non-limiting examples of alkyl groups according to the invention are, for example, methyl, ethyl, propyl, isopropyl, n-butyl, iso-butyl, tert-butyl, n-pentyl, iso-pentyl, n-hexyl, ethenyl, 1-propenyl, 2-propenyl, 1- or 2-butenyl, ethynyl, 1-propynyl, 2-propynyl, 1- or 2-butynyl, and the like.

Alkyl groups according to the present invention may be unsubstituted or substituted by one or more substituents as defined below.

The term "cycloalkyl", as used herein, refers to a saturated or partially unsaturated carbocyclic group having a single ring. It includes cycloalkenyl groups.

Non-limiting examples of cycloalkyl groups according to the invention are, for example, cyclopropane, cyclobutane, cyclopentane, cyclohexane, cycloheptane, cyclopentene, cyclohexene, cyclohexadiene and the like.

Cycloalkyl groups according to the present invention may be unsubstituted or substituted by one or more substituents as defined below.

The term "heterocycloalkyl" group, ("non-aromatic heterocycle" group), refers to a cycloalkyl group (non aromatic group) wherein at least one of the carbon atoms has been replaced by a heteroatom selected from nitrogen, oxygen and sulfur. Heterocycloalkyl groups can be unsubstituted or substituted by one or more substituents as defined below.

Examples of heterocycloalkyls include, but are not limited to lactams, lactones, cyclic imides, cyclic thioimides, cyclic carbamates, 1-(1,2,5,6-tetrahydropyridyl), tetrahydrothiopyran, 4H-pyran, tetrahydropyran, piperidine (1-piperidinyl, 2-piperidinyl, 3-piperidinyl), 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, morpholine (4-morpholinyl, 3-morpholinyl, 2-morpholinyl) trioxane, hexahydro-1,3,5-triazine, tetrahydrothiophene, tetrahydrofuran (tetrahydrofuran-2-yl, tetrahydrofuran-3-yl), pyrroline, pyrrolidine, pyrrolidone, pyrrolidindione, pyrazoline, pyrazolidine, imidazoline, imidazolidine, 1,3-dioxole, 1,3-dioxolane, 1,3-dithiole, 1,3- dithiolane, isoxazoline, isoxazolidine, oxazoline, oxazolidine, oxazolidinone, thiazoline, thiazolidine, and 1,3-oxathiolane.

The term "halogen", as used herein, refers to fluorine, chlorine, bromine and iodine.

The term "aryl", as used herein, refers to a hydrocarbon consisting of an unsubstituted or substituted mono-, bi- or tricarbocyclic ring system, wherein the rings are fused together and at least one of the carbocyclic ring is aromatic. The term "aryl" means for example a cyclic aromatic such as a 6-membered hydrocarbon ring, a two six-membered fused hydrocarbon rings. Non-limiting examples of aryl groups are, for example, phenyl, alpha- or beta-naphthyl, 9,10-dihydroanthracenyl, indanyl, fluorenyl and the like. Aryl groups according to the present invention may be unsubstituted or substituted by one or more substituents as defined below.

The term "heteroaryl", as used herein, refers to an aryl as defined above wherein one to four carbon atoms are independently replaced by heteroatoms chosen from the group consisting of nitrogen, oxygen and sulphur. Non-limiting examples of heteroaryl groups are, for example, pyrrolyl, furyl, thiophenyl, imidazolyl, pyrazolyl, oxazolyl, isoxazolyl, thiazolyl, isothiazolyl, indolyl, benzofuranyl, benzothiophenyl, benzimidazolyl, benzopyrazolyl, benzoxazolyl, benzoisoxazolyl, benzothiazolyl, benzoisothiazolyl, triazolyl, oxadiazolyl, tetrazolyl, pyridyl, pyrazinyl, pyrimidinyl, pyridazinyl, quinolinyl, isoquinolinyl, quinazolinyl, quinoxalinyl. Heteroaryl groups according to the present invention may be unsubstituted or substituted by one or more substituents as defined below.

Unless otherwise indicated, the term "substituted", as used herein, means that one or more hydrogen atoms of the above mentioned groups are replaced with another non-hydrogen atom or functional group referred to as substituent, provided that normal valencies are maintained and that the substitution results in a stable compound. Non-limiting example of substituents are, for example, OH, $C_{1-6}$alkyl, aryl, $C_{1-6}$alkylaryl, $C_{3-6}$cycloalkyl, O—$C_{1-6}$alkyl, O—$C_{3-6}$cycloalkyl, O-aryl, O—$C_{1-6}$alkylaryl, heteroaryl, heterocycloalkyl, O-heteroaryl, O-heterocycloalkyl, trifluoromethyl, difluoromethyl, trifluoromethoxy, difluoromethoxy, acyl, aroyl, heteroaroyl, halogen, nitro, cyano, $COOR^z$, alkylthio, arylthio, alkylsulfinyl, arylsulfinyl, alkylsulfonyl, arylsulfonyl, —O—C(=O)—$NR^hR^k$, —C(=O)—$NR^hR^k$, and —$NR^pR^q$, wherein each of $R^z$, $R^h$, and $R^k$, independently represents hydrogen, $C_{1-6}$alkyl, $C_{3-6}$Cycloalkyl, aryl, $C_{1-6}$alkylaryl, heteroaryl, heterocycloalkyl, and $R^p$ and $R^q$ independently represents hydrogen, $C_{1-6}$alkyl, $C_{3-6}$cycloalkyl, aryl, $C_{1-6}$alkylaryl, heteroaryl, heterocycloalkyl, $COR^z$, $COOR^z$, —C(=O)—$NR^hR^k$, —S(=O)$_2$—$R^z$, and —S(=O)$_2$—$NR^hR^k$, and when $R^h$ and $R^k$, or $R^p$ and $R^q$ are taken together with the nitrogen atom to which they are bound, the group-$NR^hR^k$ or the group $NR^pR^q$ represent a heterocycloalkyl residue, and wherein the terms alkyl, cycloalkyl, aryl, heteroaryl, heterocyclyl are as above defined.

Preferred substituents are OH, $C_{1-6}$alkyl, O—$C_{1-6}$alkyl, trifluoromethyl, difluoromethyl, halogen, $C_{3-6}$cycloalkyl, O—$C_{3-6}$cycloalkyl, trifluoromethoxy, difluoromethoxy, cyano, —$NR^pR^q$ and $COOR^z$ wherein $R^z$ is selected from the group consisting of H, methyl, ethyl, propyl, butyl, i-propyl, t-butyl, and $R^p$ and $R^q$ are independently selected from H, methyl, ethyl, butyl, i-propyl, phenyl, $COR^z$, $COOR^z$, —C(=O)—$NR^hR^k$, and —S(=O)$_2$—$R^z$. More preferred substituents are selected from OH, methyl, methoxy, chlorine, fluorine, trifluoromethyl, trifluoromethoxy, cyano, —$NR^pR^q$ and $COOR^z$ wherein $R^z$ is selected from the group consisting of H, methyl, ethyl and t-butyl, and $R^p$ and $R^q$ are independently selected from H, methyl, ethyl, butyl, i-propyl, phenyl, and acyl.

The term "pharmaceutically acceptable salts" refers to salts of the below identified compounds of Formula (Ia) and (Ib) that retain the desired biological activity and are accepted by regulatory authorities.

As used herein, the term "salt" refers to any salt of a compound according to the present invention prepared from an inorganic or organic acid or base and internally formed salts. Typically, such salts have a physiologically acceptable anion or cation.

Furthermore, the compounds of Formula (Ia) and (Ib) may form an acid addition salt or a salt with a base, depending on the kind of the substituents, and these salts are included in the present invention, as long as they are pharmaceutically acceptable salts.

Examples of such salts include, but are not restricted to acid addition salts formed with inorganic acids (e. g. hydrochloric acid, hydrobromic acid, sulfuric acid, phosphoric acid, nitric acid, and the like), and salts formed with organic acids such as acetic acid, trifluoroacetic acid, oxalic acid, tartaric acid, succinic acid, malic acid, fumaric acid, maleic acid, ascorbic acid, benzoic acid, alginic acid, polyglutamic acid, methanesulfonic acid, p-toluene sulfonic acid, and naphthalene sulfonic acid.

The compounds of Formula (Ia) and (Ib) containing acidic protons may be converted into their therapeutically active, non-toxic base addition salt forms, e.g. metal or amine salts, by treatment with appropriate organic and inorganic bases. Appropriate base salt forms include, for example, ammonium salts, alkali and earth alkaline metal salts, e.g. lithium, sodium, potassium, magnesium, calcium salts and the like, salts with organic bases, e.g. N-methyl-D-glucamine, hydrabamine salts, and salts with amino acids such as, for example, arginine, lysine and the like.

Physiologically or pharmaceutically acceptable salts are particularly suitable for medical applications because of their greater aqueous solubility relative to the parent compound.

Pharmaceutically acceptable salts may also be prepared from other salts including other pharmaceutically acceptable salts of the compounds of Formula (Ia) and (Ib) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compounds of the invention are within the scope of the invention. The compounds of Formula (Ia) and (Ib) may readily be isolated in association with solvent molecules by crystallization or evaporation of an appropriate solvent to give the corresponding solvates.

The compounds of Formula (Ia) and (Ib) may be in crystalline form. In certain embodiments, the crystalline forms of the compounds of Formula (Ia) and (Ib) are polymorphs.

The subject invention also includes isotopically-labelled compounds, which are identical to those recited in Formula (Ia) and (Ib) and following, but differ for the fact that one or more atoms are replaced by an atom having an atomic mass or mass number different from the atomic mass or mass number usually found in nature. Examples of isotopes that can be incorporated into the compounds of the invention and pharmaceutically acceptable salts thereof include isotopes of hydrogen, carbon, nitrogen, oxygen, sulfur, fluorine, and chlorine, such as $^2H$, $^3H$, $^{11}C$, $^{13}C$, $^{14}C$, $^{15}N$, $^{17}O$, $^{18}O$, $^{35}S$, $^{18}F$, $^{36}Cl$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3H$, $^{14}C$ are incorporated, are useful in drug and/or substrate tissue distribution assays. Tritiated, i.e. $^3H$, and carbon-14, i.e. $^{14}C$, isotopes are particularly preferred for their ease of preparation and detectability. $^{11}C$ and $^{18}F$ isotopes are particularly useful in PET (Positron Emission Tomography). Furthermore, substitution with heavier isotopes such as deuterium, i.e. $^2H$, can afford certain therapeutic advantages resulting from greater metabolic stability, for example increased in vivo half-life or reduced dosage requirements and, hence, may be preferred in some circumstances. Isotopically-labelled compounds of Formula (Ia) and (Ib) and following of this invention can generally be prepared by carrying out the procedures disclosed in the Schemes and/or in the Examples below, by replacing a non-isotopically-labelled reagent with a readily available isotopically-labelled reagent.

Certain groups/substituents included in the present invention may be present as isomers or in one or more tautomeric forms. Accordingly, in certain embodiments, the compounds of Formula (Ia) and (Ib) may exist in the form of other tautomers or geometrical isomers in some cases, depending on the kinds of the substituents. In the present specification, the compounds may be described in only one form of such isomers, but the present invention includes all such isomers, isolated forms of the isomers, or a mixture thereof. Furthermore, the compounds of Formula (Ia) and (Ib) may have asymmetric carbon atoms or axial asymmetries in some cases and, correspondingly, they may exist in the form of optical isomers such as an (R)-form, an(S)-form, and the like. The present invention includes within the scope all such isomers, including racemates, enantiomers and mixtures thereof.

In particular, within the scope of the present invention are included all stereoisomeric forms, including enantiomers, diastereoisomers, and mixtures thereof, including racemates and the general reference to the compounds of Formula (Ia) and (Ib) includes all the stereoisomeric forms, unless otherwise indicated.

In general, the compounds or salts of the invention should be interpreted as excluding those compounds (if any) which are so chemically unstable, either per se or in water, that they are clearly unsuitable for pharmaceutical use through all administration routes, whether oral, parenteral, or otherwise. Such compounds are known to the skilled chemist.

BEST MODE FOR CARRYING OUT THE INVENTION

According to a first aspect of the invention, compounds of Formula (Ia):

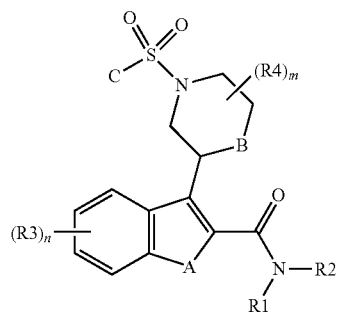

or pharmaceutically acceptable salts, hydrates, solvates, clathrates, polymorphs, stereoisomers thereof are provided.

In the compounds of Formula (Ia):

R1 and R2 are independently selected from the group consisting of hydrogen, $C_{1-4}$alkyl, hydroxy$C_{1-4}$alkyl, and $C_{1-4}$alkyl-O—$C_{1-4}$alkyl;

R3 is selected from the group consisting of $C_{1-6}$alkyl, halo$C_{1-6}$alkyl, OH, O—$C_{1-6}$alkyl, $C_{1-6}$alkyl-O—$C_{1-6}$alkyl, CN, $NO_2$ and halogen;

R4 is independently selected from the group consisting of $C_{1-6}$alkyl, halo$C_{1-6}$alkyl and halogen; A is selected from the group consisting of S, SO, and $SO_2$;

B is selected from the group consisting of $CR^{iv}R^v$, O, and $NR^{ii}$;

C is selected from the group consisting of $C_{1-6}$alkyl, halo$C_{1-6}$alkyl, $C_{3-6}$cycloalkyl optionally substituted with one or more R5, $C_{3-6}$heterocycloalkyl optionally substituted with one or more R5, aryl optionally substituted with one or more R5, heteroaryl optionally substituted with one or more R5, $C_{1-6}$alkyl-O—$C_{1-6}$alkyl, $C_{1-6}$alkyl-O-aryl, $C_{1-6}$alkyl-O-heteroaryl, $C_{1-6}$alkyl-O—$C_{3-6}$heterocycloalkyl, aryl-O-aryl, and aryl-O-heteroaryl;

R5 is selected from the group consisting of $C_{1-6}$alkyl, halo$C_{1-6}$alkyl, O—$C_{1-6}$alkyl, $C_{3-6}$Cycloalkyl, $C_{3-6}$heterocycloalkyl, aryl, heteroaryl, O-aryl, O-aryl-O—$C_{1-6}$alkyl, O-heteroaryl, O—$C_{3-6}$heterocycloalkyl, O-halo$C_{1-6}$alkyl, OH, CN, $NO_2$, $SF_6$, halogen and $COOR^i$;

n is an integer comprised from 0 to 2;

m is an integer comprised from 0 to 2;

$R^i$ is independently selected from the group consisting of hydrogen and $C_{1-6}$alkyl;

$R^{ii}$ is independently selected from the group consisting of hydrogen and $C_{1-6}$alkyl;

$R^{iv}$ and $R^v$ are independently selected from the group consisting of hydrogen, $C_{1-6}$alkyl and hydroxy$C_{1-6}$alkyl;

provided that:

a) when A is S, B is O, R1 and R2 are both $CH_3$, R3 and R4 are both H, C is not one of

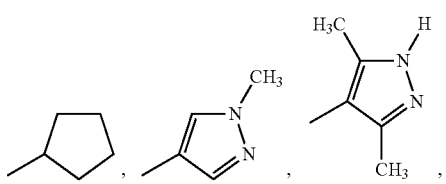

-continued

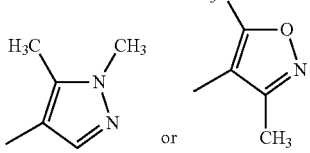
or b) when A is S, B is O, R1 and R2 are respectively CH₃ and H, R3 and R4 are both H, C is not one of

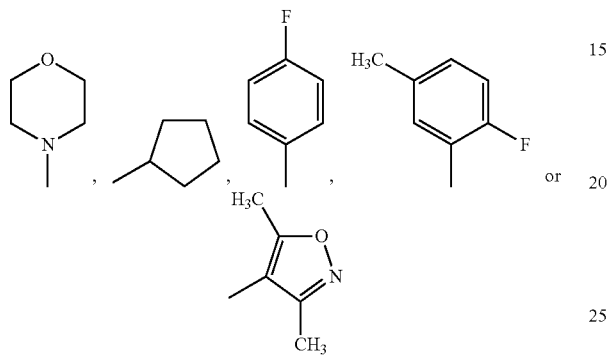
or c) when A is S, B is O, R1 and R2 are respectively isopropyl and H, R3 and R4 are both H, C is not one of

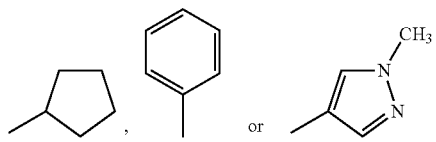
or d) when A is S, B is O, R1 and R2 are both H, R3 and R4 are both H, C is not one of

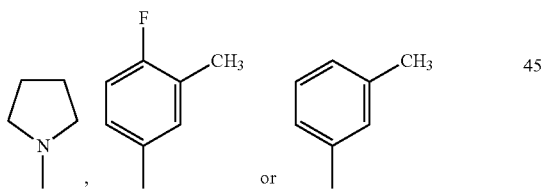
or e) when A is S, B is O, R1 and R2 are respectively H and CH₂CH₂OH, R3 and R4 are both H, C is not phenyl.

According to a first embodiment, B is O.

According to a second embodiment, R1 and R2 are hydrogen, $C_{1-4}$alkyl and hydroxy$C_{1-4}$alkyl. In a further embodiment R1 and R2 are independently selected from the group consisting of hydrogen, methyl, ethyl, isopropyl and hydroxyethyl; preferably R1 and R2 are hydrogen.

According to a third embodiment, R3 and R4 are hydrogen.

According to a fourth embodiment, A is selected from the group consisting of S and SO₂.

According to a fifth embodiment, C is selected from the group consisting of $C_{1-6}$alkyl, $C_{3-6}$cycloalkyl optionally substituted with one or more R5, $C_{3-6}$heterocycloalkyl optionally substituted with one or more R5, aryl optionally substituted with one or more R5, heteroaryl optionally substituted with one or more R5 and $C_{1-6}$alkyl-O—$C_{1-6}$alkyl.

In a sixth embodiment, C is selected from the group consisting of $C_{1-6}$alkyl, $C_{1-6}$alkyl-O—$C_{1-6}$alkyl, $C_{3-6}$cycloalkyl optionally substituted with one or more R5,

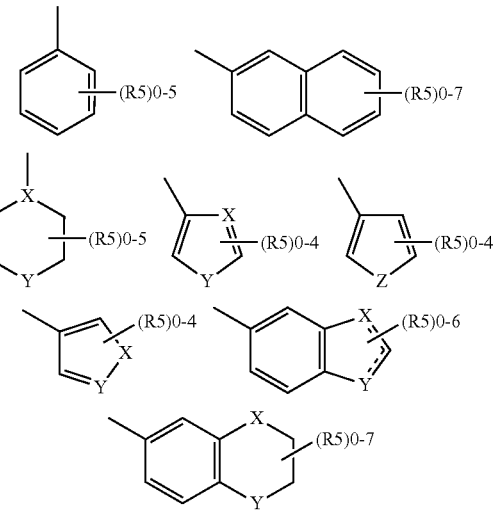

wherein X and Y are selected from the group consisting of C, O and N, and Z is selected from the group consisting of N, O and S.

In a seventh embodiment, C is selected from the group consisting of:

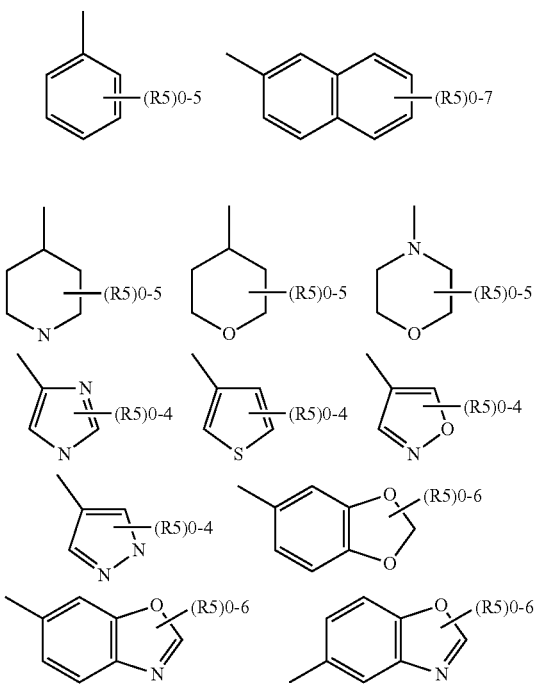

According to an eighth embodiment, the compounds of Formula (Ia) are selected from the group consisting of:

| | |
|---|---|
| 002 | rac-3-[4-(1,2-dimethylimidazol-4-yl) sulfonylmorpholin-2-yl]benzothiophene-2-carboxamide |
| 003 | rac-3-[4-(benzenesulfonyl)morpholin-2-yl]benzothiophene-2-carboxamide |
| 004 | rac-3-[4-(1H-imidazol-4-ylsulfonyl)morpholin-2-yl]benzothiophene-2-carboxamide |
| 005 | rac-3-[4-(3-thienylsulfonyl)morpholin-2-yl]benzothiophene-2-carboxamide |
| 006 | rac-3-[4-(4-phenoxyphenyl)sulfonylmorpholin-2-yl]benzothiophene-2-carboxamide |
| 007 | rac-methyl 3-[2-(2-carbamoylbenzothiophen-3-yl)morpholin-4-yl] sulfonylbenzoate |
| 008 | rac-3-[4-(3,5-dimethylisoxazol-4-yl) sulfonylmorpholin-2-yl]benzothiophene-2-carboxamide |
| 009 | rac-3-[4-(3-bromophenyl)sulfonylmorpholin-2-yl]benzothiophene-2-carboxamide |
| 010 | rac-3-[4-(4-methoxyphenyl)sulfonylmorpholin-2-yl]benzothiophene-2-carboxamide |
| 011 | rac-3-[4-[4-(trifluoromethyl)phenyl] sulfonylmorpholin-2-yl]benzothiophene-2-carboxamide |
| 012 | rac-3-[4-(m-tolylsulfonyl)morpholin-2-yl]benzothiophene-2-carboxamide |
| 015 | rac-3-[4-[4-(2-oxopyrrolidin-1-yl)phenyl] sulfonylmorpholin-2-yl]benzothiophene-2-carboxamide |
| 016 | rac-3-[4-cyclohexylsulfonylmorpholin-2-yl]benzothiophene-2-carboxamide |
| 017 | rac-3-[4-(1,3-benzodioxol-5-ylsulfonyl)morpholin-2-yl]benzothiophene-2-carboxamide |
| 018 | rac-3-[(4-(2,3-dihydro-1,4-benzodioxin-6-ylsulfonyl)morpholin-2-yl]benzothiophene-2-carboxamide |
| 019 | rac-3-[4-[4-(4-methoxyphenoxy)phenyl] sulfonylmorpholin-2-yl]benzothiophene-2-carboxamide |
| 020 | rac-3-[4-(3-fluorophenyl)sulfonylmorpholin-2-yl]benzothiophene-2-carboxamide |
| 021 | rac-3-[4-(3,4-difluorophenyl)sulfonylmorpholin-2-yl]benzothiophene-2-carboxamide |
| 022 | rac-3-[4-(4-fluorophenyl)sulfonylmorpholin-2-yl]benzothiophene-2-carboxamide |
| 023 | rac-3-[4-(4-methoxy-3-methyl-phenyl) sulfonylmorpholin-2-yl]benzothiophene-2-carboxamide |
| 024 | rac-3-[4-[4-(4-pyridyloxy)phenyl]sulfonylmorpholin-2-yl]benzothiophene-2-carboxamide |
| 025 | rac-3-[4-(4-fluoro-3-methyl-phenyl) sulfonylmorpholin-2-yl]-N,N-dimethyl-benzothiophene-2-carboxamide |
| 026 | rac-3-[4-(3-fluoro-4-methyl-phenyl)sulfonylmorpholin-2-yl]benzothiophene-2-carboxamide |
| 027 | rac-3-[4-(5-fluoro-2-methyl-phenyl)sulfonylmorpholin -2-yl]benzothiophene-2-carboxamide |
| 028 | rac-3-[4-(4-fluoro-3-methyl-phenyl) sulfonylmorpholin-2-yl]-N-methyl-benzothiophene-2-carboxamide |
| 029 | rac-3-[4-(4-fluoro-3-methyl-phenyl)sulfonyl morpholin-2-yl]-N-(2-hydroxyethyl)benzothiophene-2-carboxamide |
| 030 | rac-N-ethyl-3-[4-(4-fluoro-3-methyl-phenyl)sulfonylmorpholin-2-yl]benzothiophene-2-carboxamide |
| 031 | rac-3-[4-(4-fluoro-3-methyl-phenyl) sulfonylmorpholin-2-yl]-N-isopropyl-benzothiophene-2-carboxamide |
| 032 | rac-3-[4-(2,4,6-trimethylphenyl)sulfonylmorpholin-2-yl]benzothiophene-2-carboxamide |
| 033 | rac-3-[4-(p-tolylsulfonyl)morpholin-2-yl] benzothiophene-2-carboxamide |
| 034 | rac-3-[4-[(2-methyl-1,3-benzoxazol-6-yl) sulfonyl]morpholin-2-yl]benzothiophene-2-carboxamide |
| 035 | rac-3-[4-[3-(trifluoromethyl)phenyl] sulfonylmorpholin-2-yl]benzothiophene-2-carboxamide |
| 036 | rac-3-[4-(4-tert-butylphenyl)sulfonylmorpholin-2-yl]benzothiophene-2-carboxamide |
| 037 | rac-3-[4-(4-cyanophenyl)sulfonylmorpholin-2-yl]benzothiophene-2-carboxamide |
| 038 | rac-3-[4-[4-fluoro-3-(trifluoromethyl)phenyl] sulfonylmorpholin-2-yl]benzothiophene-2-carboxamide |
| 039 | rac-3-[4-[4-(trifluoromethoxy)phenyl] sulfonylmorpholin-2-yl]benzothiophene-2-carboxamide |
| 040 | rac-3-[4-(4-chlorophenyl)sulfonylmorpholin-2-yl]benzothiophene-2-carboxamide |
| 041 | rac-3-[4-[3-fluoro-4-(trifluoromethyl)phenyl] sulfonylmorpholin-2-yl]benzothiophene-2-carboxamide |
| 042 | 3-[(R) or (S)-4-[4-(trifluoromethyl)phenyl] sulfonylmorpholin-2-yl]benzothiophene-2-carboxamide |

| | |
|---|---|
| 043 | 3-[(S) or (R)-4-[4-(trifluoromethyl)phenyl] sulfonylmorpholin-2-yl]benzothiophene-2-carboxamide |
| 044 | rac-3-[4-[3-methyl-4-(trifluoromethyl)phenyl] sulfonylmorpholin-2-yl]benzothiophene-2-carboxamide |
| 045 | rac-3-[4-[3-methoxy-4-(trifluoromethyl)phenyl] sulfonylmorpholin-2-yl]benzothiophene-2-carboxamide |
| 046 | rac-3-[4-[4-methoxy-3-(trifluoromethyl)phenyl] sulfonylmorpholin-2-yl]benzothiophene-2-carboxamide |
| 047 | rac-3-[4-(4-methoxy-3-nitro-phenyl) sulfonylmorpholin-2-yl]benzothiophene-2-carboxamide |
| 048 | rac-3-[4-(3-methoxyphenyl)sulfonylmorpholin-2-yl]benzothiophene-2-carboxamide |
| 049 | rac-3-[4-[3-(trifluoromethoxy)phenyl] sulfonylmorpholin-2-yl]benzothiophene-2-carboxamide |
| 050 | rac-3-[4-(2-methoxyphenyl)sulfonylmorpholin-2-yl]benzothiophene-2-carboxamide |
| 051 | rac-3-[4-(4-phenylphenyl)sulfonylmorpholin-2-yl]benzothiophene-2-carboxamide |
| 052 | rac-3-[4-(2-naphthylsulfonyl)morpholin-2-yl]benzothiophene-2-carboxamide |
| 053 | rac-3-[4-(3-fluoro-4-methoxy-phenyl) sulfonylmorpholin-2-yl]benzothiophene-2-carboxamide |
| 054 | rac-3-[4-(3,4-dimethoxyphenyl)sulfonylmorpholin-2-yl]benzothiophene-2-carboxamide |
| 055 | 3-[(S) or (R)-4-[3-fluoro-4-(trifluoromethyl)phenyl] sulfonylmorpholin-2-yl]benzothiophene-2-carboxamide |
| 056 | 3-[(R) or (S)-4-[3-fluoro-4-(trifluoromethyl)phenyl] sulfonylmorpholin-2-yl]benzothiophene-2-carboxamide |
| 057 | rac-3-[4-[(4-methyl-2,3-dihydro-1,4-benzoxazin-7-yl)sulfonyl]morpholin-2-yl]benzothiophene-2-carboxamide |
| 058 | rac-3-[4-tetrahydropyran-4-ylsulfonylmorpholin-2-yl]benzothiophene-2-carboxamide |
| 059 | rac-3-[4-(2-methoxyethylsulfonyl)morpholin-2-yl]benzothiophene-2-carboxamide |
| 060 | rac-3-[4-[4-(pentafluoro-lambda6-sulfanyl) phenyl]sulfonylmorpholin-2-yl]benzothiophene-2-carboxamide |
| 061 | rac-3-[4-butylsulfonylmorpholin-2-yl]benzothiophene-2-carboxamide |
| 062 | rac-3-[4-(3-cyanophenyl)sulfonylmorpholin-2-yl]benzothiophene-2-carboxamide |
| 063 | rac-methyl 4-[2-(2-carbamoylbenzothiophen-3-yl)morpholin-4-yl]sulfonylbenzoate |
| 064 | rac-tert-butyl 4-[2-(2-carbamoylbenzothiophen-3-yl)morpholin-4-yl]sulfonylpiperidine-1-carboxylate |
| 065 | rac-3-[4-(4-nitrophenyl)sulfonylmorpholin-2-yl] benzothiophene-2-carboxamide |
| 066 | rac-3-[4-[2-(trifluoromethyl)phenyl] sulfonylmorpholin-2-yl]benzothiophene-2-carboxamide |
| 067 | rac-3-[4-[2-(trifluoromethoxy)phenyl] sulfonylmorpholin-2-yl]benzothiophene-2-carboxamide |
| 068 | rac-3-[4-(4-hydroxyphenyl)sulfonylmorpholin-2-yl]benzothiophene-2-carboxamide |
| 069 | rac-3-[4-(4-isopropoxyphenyl)sulfonylmorpholin-2-yl]benzothiophene-2-carboxamide |
| 070 | 3-[(S) or (R)-4-[(2-methyl-1,3-benzoxazol-6-yl) sulfonyl]morpholin-2-yl]benzothiophene-2-carboxamide |
| 071 | 3-[(R) or (S)-4-[(2-methyl-1,3-benzoxazol-6-yl) sulfonyl]morpholin-2-yl]benzothiophene-2-carboxamide |
| 072 | 3-[(S) or (R)-4-(3-fluoro-4-methyl-phenyl) sulfonylmorpholin-2-yl]benzothiophene-2-carboxamide |
| 073 | 3-[(R) or (S)-4-(3-fluoro-4-methyl-phenyl) sulfonylmorpholin-2-yl]benzothiophene-2-carboxamide and |
| 074 | rac-1,1-dioxo-3-[4-[3-fluoro-4-(trifluoromethyl) phenyl]sulfonylmorpholin-2-yl]benzothiophene-2-carboxamide. |

A second aspect of the present invention relates to a pharmaceutical composition comprising a compound of Formula (Ia) or pharmaceutically acceptable salts, hydrates, solvates, clathrates, polymorphs, stereoisomers thereof and a pharmaceutically acceptable carrier, stabilizer, diluent or excipient thereof. A person skilled in the art is aware of a whole variety of such carrier, diluent or excipient compounds suitable to formulate a pharmaceutical composition.

Compounds (Ib) have the following Formula:

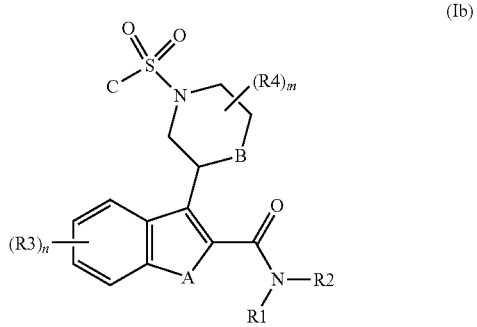

or pharmaceutically acceptable salts, hydrates, solvates, clathrates, polymorphs, stereoisomers thereof wherein:

R1 and R2 are independently selected from the group consisting of hydrogen, $C_{1-4}$alkyl, hydroxy$C_{1-4}$alkyl, and $C_{1-4}$alkyl-O—$C_{1-4}$alkyl;

R3 is selected from the group consisting of $C_{1-6}$alkyl, halo$C_{1-6}$alkyl, OH, O—$C_{1-6}$alkyl, $C_{1-6}$alkyl-O—$C_{1-6}$alkyl, CN, $NO_2$ and halogen;

R4 is independently selected from the group consisting of $C_{1-6}$alkyl, halo$C_{1-6}$alkyl and halogen;

A is selected from the group consisting of S, SO, and $SO_2$;

B is selected from the group consisting of $CR^{iv}R^{v}$, O, and $NR^{ii}$;

C is selected from the group consisting of $C_{1-6}$alkyl, halo$C_{1-6}$alkyl, $C_{3-6}$cycloalky optionally substituted with one or more R5, $C_{3-6}$heterocycloalkyl optionally substituted with one or more R5, aryl optionally substituted with one or more R5, heteroaryl optionally substituted with one or more R5, $C_{1-6}$alkyl-O—$C_{1-6}$alkyl, $C_{1-6}$alkyl-O-aryl, $C_{1-6}$alkyl-O-heteroaryl, $C_{1-6}$alkyl-O—$C_{3-6}$heterocycloalkyl, aryl-O-aryl, and aryl-O-heteroaryl;

R5 is selected from the group consisting of $C_{1-6}$alkyl, halo$C_{1-6}$alkyl, O—$C_{1-6}$alkyl, $C_{3-6}$cycloalkyl, $C_{3-6}$ heterocycloalkyl, aryl, heteroaryl, O-aryl, O-aryl-O—$C_{1-6}$alkyl, O-heteroaryl, O—$C_{3-6}$heterocycloalkyl, O-halo$C_{1-6}$alkyl, OH, CN, $NO_2$, $SF_6$, halogen and $COOR^i$;

n is an integer comprised from 0 to 2;

m is an integer comprised from 0 to 2;

$R^i$ is independently selected from the group consisting of hydrogen and $C_{1-6}$alkyl;

$R^{ii}$ is independently selected from the group consisting of hydrogen and $C_{1-6}$alkyl;

$R^{iv}$ and $R^v$ are independently selected from the group consisting of hydrogen, $C_{1-6}$alkyl and hydroxy$C_{1-6}$alkyl.

According to a further embodiment, B is O.

According to a further embodiment, R1 and R2 are hydrogen, $C_{1-4}$alkyl and hydroxy$C_{1-4}$alkyl. In a further embodiment R1 and R2 are independently selected from the group consisting of hydrogen, methyl, ethyl, isopropyl and hydroxyethyl; preferably R1 and R2 are hydrogen.

According to a further embodiment, R3 and R4 are hydrogen.

According to a further embodiment, A is selected from the group consisting of S and $SO_2$.

According to a further embodiment, C is selected from the group consisting of $C_{1-6}$alkyl, $C_{3-6}$cycloalkyl optionally substituted with one or more R5, $C_{3-6}$heterocycloalkyl optionally substituted with one or more R5, aryl optionally substituted with one or more R5, heteroaryl optionally substituted with one or more R5 and $C_{1-6}$alkyl-O—$C_{1-6}$alkyl.

In a further embodiment, C is selected from the group consisting of $C_{1-6}$alkyl, $C_{1-6}$alkyl-O—$C_{1-6}$alkyl, $C_{3-6}$Cycloalkyl optionally substituted with one or more R5,

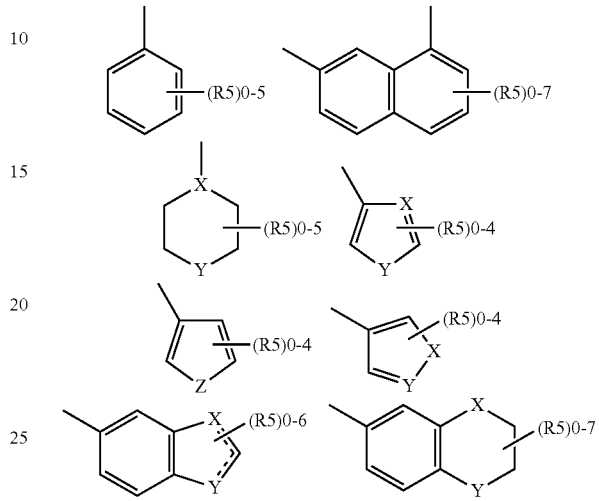

wherein X and Y are selected from the group consisting of C, O and N and Z is selected from the group consisting of N, O and S.

In a further embodiment, C is selected from the group consisting of:

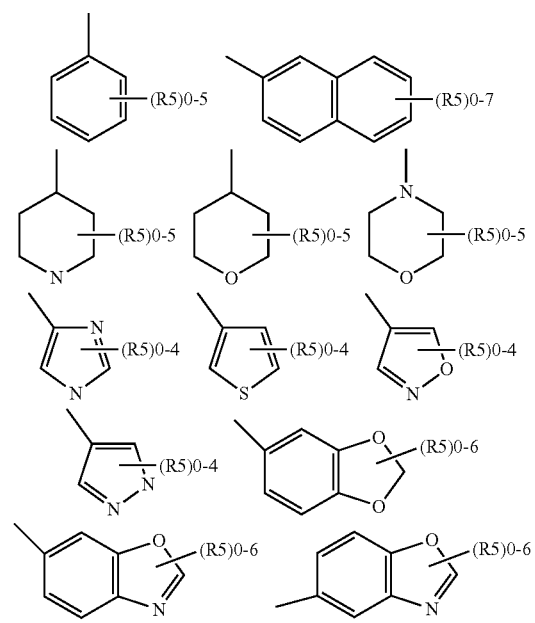

Compounds of Formula (Ia), together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral administration (including subcutaneous and intravenous use). Such pharmaceutical compositions and unit dosage thereof may comprise ingredients in conventional proportions, with or without additional active compounds or principles, and such unit dosage forms may contain any suitable effective amount of the active ingredient commensurate with the intended daily dosage range to be employed.

Pharmaceutical compositions containing a compound of this invention can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the present invention can be administered by a variety of routes including oral, rectal, subcutaneous, intravenous, intramuscular, intranasal and pulmonary routes. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include pre-filled, pre-measured ampoules or syringes of the liquid compositions or pills, tablets, capsules or the like in the case of solid compositions.

Liquid forms suitable for oral administration may include a suitable aqueous or non-aqueous vehicle with buffers, suspending and dispensing agents, colorants, flavours and the like. Solid forms may include, for example, any of the following ingredients, or compounds of a similar nature: a binder such as microcrystalline cellulose, gum tragacanth, acacia, corn starch or gelatine; an excipient such as starch, dicalcium phosphate or lactose, a disintegrating agent such as alginic acid, Primogel or corn starch; a lubricant such as magnesium stearate; a glidant such as colloidal silicon dioxide; a sweetening agent such as sucrose, lactose or saccharin; or a flavouring agent such as peppermint, methyl salicylate, or orange flavouring.

Injectable compositions are typically based upon injectable sterile saline or phosphate-buffered saline or other injectable carriers known in the art.

The pharmaceutical compositions may be in the form of tablets, pills, capsules, solutions, suspensions, emulsion, powders, suppository and as sustained release formulations.

If desired, tablets may be coated by standard aqueous or non-aqueous techniques. In certain embodiments, such compositions and preparations can contain at least 0.1 percent of active compound. The percentage of active compound in these compositions may, of course, be varied and may conveniently be between about 1 percent to about 60 percent of the weight of the unit. The amount of active compound in such therapeutically useful compositions is such that therapeutically active dosage will be obtained.

When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring agent such as cherry or orange flavor. To prevent breakdown during transit through the upper portion of the gastrointestinal tract, the composition be an enteric coated formulation.

The active compounds can also be administered intranasally as, for example, liquid drops or spray.

Compositions for pulmonary administration include, but are not limited to, dry powder compositions consisting of the powder of a compound of Formula (Ia) or a salt thereof, and the powder of a suitable carrier and/or lubricant. The compositions for pulmonary administration can be inhaled from any suitable dry powder inhaler device known to a person skilled in the art.

Administration of the compositions is performed under a protocol and at a dosage sufficient to reduce the inflammation and pain in the subject. In some embodiments, in the pharmaceutical compositions of the present invention the active principle or active principles are generally formulated in dosage units. The dosage unit may contain from 0.1 to 1000 mg of a compound of Formula (Ia) per dosage unit for daily administration.

In some embodiments, the amounts effective for a specific formulation will depend on the severity of the disease, disorder or condition, previous therapy, the individual's health status and response to the drug. In some embodiments, the dose is in the range from 0.001% by weight to about 60% by weight of the formulation.

When used in combination with one or more other active ingredients, the compound of the present invention and the other active ingredient may be used in lower doses than when each is used singly.

Concerning formulations with respect to any variety of routes of administration, methods and formulations for the administration of drugs are disclosed in Remington's Pharmaceutical Sciences, 17th Edition, Gennaro et al. Eds., Mack Publishing Co., 1985, and Remington's Pharmaceutical Sciences, Gennaro A R ed. 20th Edition, 2000, Williams & Wilkins PA, USA, and Remington: The Science and Practice of Pharmacy, 21st Edition, Lippincott Williams & Wilkins Eds., 2005; and in Loyd V. Allen and Howard C. Ansel, Ansel's Pharmaceutical Dosage Forms and Drug Delivery Systems, 10th Edition, Lippincott Williams & Wilkins Eds., 2014.

The above described components for orally administered or injectable compositions are merely representative.

The compounds of this invention can also be administered in sustained release forms or from sustained release drug delivery systems.

A third aspect of the present invention relates to of compounds Formula (Ib) as disclosed above or the pharmaceutical composition thereof, for the use as a medicament.

A fourth aspect of the present invention relates to compounds of Formula (Ib) or pharmaceutically acceptable solvates, salts, hydrates, clathrates, polymorphs, stereoisomers thereof, for the use to modulate, in particular to correct, CFTR protein or ABC protein activities.

Compounds of Formula (Ia) and (Ib) as disclosed above may also be effective for the treatment of patients with other protein misfolding diseases. In this respect, other, structurally different CFTR correctors were found to rescue proteins (AVPR2, HCNH2, and ABCC8) with mutations causing trafficking defects (Sampson et al., *Orphanet J Rare Dis* 8:11, 2013). The compounds of Formula (Ia) and (Ib) may be indicated in particular for ABC proteins that share with CFTR a similar structure, particularly at the level of nucleotide-binding domains (Rudashevskaya et al., *Drug Discov*

Today Technol 12: e87-94, 2014). A list of ABC proteins with trafficking defects and associated diseases that could benefit from modulators CFTR includes ABCA1 (Tangier disease), ABCA3 (fatal surfactant deficiency), ABCA 4 (Stargardt disease), ABCB 4 (progressive familial intrahepatic cholestasis type 3), ABCB11 (progressive familial intrahepatic cholestasis type 2), ABCC2 (Dubin-Johnson syndrome), ABCC8 (hyperinsulinemic hypoglycemia of infancy) and ABCG2 (gout).

According to an aspect of the present invention, compounds of Formula (Ia) and (Ib) as disclosed above or the pharmaceutical composition thereof can be used in the treatment of a disease selected from the group consisting of cystic fibrosis, chronic obstructive pulmonary disease, chronic constipation, and dry eye syndrome, preferably cystic fibrosis.

In particular, the following compounds can be used:

| | |
|---|---|
| 001 | rac-3-[4-(4-Fluoro-3-methyl-benzenesulfonyl)-morpholin-2-yl]-benzo[b]thiophene-2-carboxylic acid amide |
| 002 | rac-3-[4-(1,2-dimethylimidazol-4-yl) sulfonylmorpholin-2-yl]benzothiophene-2-carboxamide |
| 003 | rac-3-[4-(benzenesulfonyl)morpholin-2-yl]benzothiophene-2-carboxamide |
| 004 | rac-3-[4-(1H-imidazol-4-ylsulfonyl)morpholin-2-yl]benzothiophene-2-carboxamide |
| 005 | rac-3-[4-(3-thienylsulfonyl)morpholin-2-yl]benzothiophene-2-carboxamide |
| 006 | rac-3-[4-(4-phenoxyphenyl)sulfonylmorpholin-2-yl]benzothiophene-2-carboxamide |
| 007 | rac-methyl 3-[2-(2-carbamoylbenzothiophen-3-yl)morpholin-4-yl] sulfonylbenzoate |
| 008 | rac-3-[4-(3,5-dimethylisoxazol-4-yl) sulfonylmorpholin-2-yl]benzothiophene-2-carboxamide |
| 009 | rac-3-[4-(3-Bromophenyl)sulfonylmorpholin-2-yl]benzothiophene-2-carboxamide |
| 010 | rac-3-[4-(4-methoxyphenyl)sulfonylmorpholin-2-yl]benzothiophene-2-carboxamide |
| 011 | rac-3-[4-[4-(trifluoromethyl)phenyl] sulfonylmorpholin-2-yl]benzothiophene-2-carboxamide |
| 012 | rac-3-[4-(m-tolylsulfonyl)morpholin-2-yl]benzothiophene-2-carboxamide |
| 013 | 3-[(R)or (S)-4-(4-fluoro-3-methyl-phenyl) sulfonylmorpholin-2-yl]benzothiophene-2-carboxamide |
| 014 | 3-[(S) or (R)-4-(4-fluoro-3-methyl-phenyl) sulfonylmorpholin-2-yl]benzothiophene-2-carboxamide |
| 015 | rac-3-[4-[4-(2-oxopyrrolidin-1-yl)phenyl] sulfonylmorpholin-2-yl]benzothiophene-2-carboxamide |
| 016 | rac-3-[4-cyclohexylsulfonylmorpholin-2-yl]benzothiophene-2-carboxamide |
| 017 | rac-3-[4-(1,3-benzodioxol-5-ylsulfonyl)morpholin-2-yl]benzothiophene-2-carboxamide |
| 018 | rac-3-[(4-(2,3-dihydro-1,4-benzodioxin-6-ylsulfonyl)morpholin-2-yl]benzothiophene-2-carboxamide |
| 019 | rac-3-[4-[4-(4-methoxyphenoxy)phenyl] sulfonylmorpholin-2-yl]benzothiophene-2-carboxamide |
| 020 | rac-3-[4-(3-fluorophenyl)sulfonylmorpholin-2-yl]benzothiophene-2-carboxamide |
| 021 | rac-3-[4-(3,4-difluorophenyl)sulfonylmorpholin-2-yl]benzothiophene-2-carboxamide |
| 022 | rac-3-[4-(4-fluorophenyl)sulfonylmorpholin-2-yl]benzothiophene-2-carboxamide |
| 023 | rac-3-[4-(4-methoxy-3-methyl-phenyl) sulfonylmorpholin-2-yl]benzothiophene-2-carboxamide |
| 024 | rac-3-[4-[4-(4-pyridyloxy)phenyl] sulfonylmorpholin-2-yl]benzothiophene-2-carboxamide |
| 025 | rac-3-[4-(4-fluoro-3-methyl-phenyl) sulfonylmorpholin-2-yl]-N,N-dimethyl-benzothiophene-2-carboxamide |
| 026 | rac-3-[4-(3-fluoro-4-methyl-phenyl) sulfonylmorpholin-2-yl]benzothiophene-2-carboxamide |
| 027 | rac-3-[4-(5-fluoro-2-methyl-phenyl) sulfonylmorpholin-2-yl]benzothiophene-2-carboxamide |
| 028 | rac-3-[4-(4-fluoro-3-methyl-phenyl)sulfonylmorpholin -2-yl]-N-methyl-benzothiophene-2-carboxamide |
| 029 | rac-3-[4-(4-fluoro-3-methyl-phenyl) sulfonylmorpholin-2-yl]-N-(2-hydroxyethyl) benzothiophene-2-carboxamide |
| 030 | rac-N-ethyl-3-[4-(4-fluoro-3-methyl-phenyl) sulfonylmorpholin-2-yl]benzothiophene-2-carboxamide |
| 031 | rac-3-[4-(4-fluoro-3-methyl-phenyl) sulfonylmorpholin-2-yl]-N-isopropyl-benzothiophene-2-carboxamide |
| 032 | rac-3-[4-(2,4,6-trimethylphenyl)sulfonylmorpholin-2-yl]benzothiophene-2-carboxamide |
| 033 | rac-3-[4-(p-tolylsulfonyl)morpholin-2-yl]benzothiophene-2-carboxamide |
| 034 | rac-3-[4-[(2-methyl-1,3-benzoxazol-6-yl) sulfonyl]morpholin-2-yl]benzothiophene-2-carboxamide |
| 035 | rac-3-[4-[3-(trifluoromethyl)phenyl] sulfonylmorpholin-2-yl]benzothiophene-2-carboxamide |
| 036 | rac-3-[4-(4-tert-butylphenyl)sulfonylmorpholin-2-yl]benzothiophene-2-carboxamide |
| 037 | rac-3-[4-(4-cyanophenyl)sulfonylmorpholin-2-yl]benzothiophene-2-carboxamide |

| | |
|---|---|
| 038 | rac-3-[4-[4-fluoro-3-(trifluoromethyl)phenyl] sulfonylmorpholin-2-yl]benzothiophene-2-carboxamide |
| 039 | rac-3-[4-[4-(trifluoromethoxy)phenyl] sulfonylmorpholin-2-yl]benzothiophene-2-carboxamide |
| 040 | rac-3-[4-(4-chlorophenyl)sulfonylmorpholin-2-yl]benzothiophene-2-carboxamide |
| 041 | rac-3-[4-[3-fluoro-4-(trifluoromethyl)phenyl] sulfonylmorpholin-2-yl]benzothiophene-2-carboxamide |
| 042 | 3-[(R) or (S)-4-[4-(trifluoromethyl)phenyl] sulfonylmorpholin-2-yl]benzothiophene-2-carboxamide |
| 043 | 3-[(S) or (R)-4-[4-(trifluoromethyl)phenyl] sulfonylmorpholin-2-yl]benzothiophene-2-carboxamide |
| 044 | rac-3-[4-[3-methyl-4-(trifluoromethyl)phenyl] sulfonylmorpholin-2-yl]benzothiophene-2-carboxamide |
| 045 | rac-3-[4-[3-methoxy-4-(trifluoromethyl)phenyl] sulfonylmorpholin-2-yl]benzothiophene-2-carboxamide |
| 046 | rac-3-[4-[4-methoxy-3-(trifluoromethyl)phenyl] sulfonylmorpholin-2-yl]benzothiophene-2-carboxamide |
| 047 | rac-3-[4-(4-methoxy-3-nitro-phenyl) sulfonylmorpholin-2-yl]benzothiophene-2-carboxamide |
| 048 | rac-3-[4-(3-methoxyphenyl)sulfonylmorpholin-2-yl]benzothiophene-2-carboxamide |
| 049 | rac-3-[4-[3-(trifluoromethoxy)phenyl] sulfonylmorpholin-2-yl]benzothiophene-2-carboxamide |
| 050 | rac-3-[4-(2-methoxyphenyl)sulfonylmorpholin-2-yl]benzothiophene-2-carboxamide |
| 051 | rac-3-[4-(4-phenylphenyl)sulfonylmorpholin-2-yl]benzothiophene-2-carboxamide |
| 052 | rac-3-[4-(2-naphthylsulfonyl)morpholin-2-yl]benzothiophene-2-carboxamide |
| 053 | rac-3-[4-(3-fluoro-4-methoxy-phenyl) sulfonylmorpholin-2-yl]benzothiophene-2-carboxamide |
| 054 | rac-3-[4-(3,4-dimethoxyphenyl)sulfonylmorpholin-2-yl]benzothiophene-2-carboxamide |
| 055 | 3-[(S) or (R)-4-[3-fluoro-4-(trifluoromethyl) phenyl]sulfonylmorpholin-2-yl]benzothiophene-2-carboxamide |
| 056 | 3-[(R) or (S)-4-[3-fluoro-4-(trifluoromethyl) phenyl]sulfonylmorpholin-2-yl]benzothiophene-2-carboxamide |
| 057 | rac-3-[4-[(4-methyl-2,3-dihydro-1,4-benzoxazin-7-yl)sulfonyl]morpholin-2-yl]benzothiophene-2-carboxamide |
| 058 | rac-3-[4-tetrahydropyran-4-ylsulfonylmorpholin-2-yl]benzothiophene-2-carboxamide |
| 059 | rac-3-[4-(2-methoxyethylsulfonyl)morpholin-2-yl]benzothiophene-2-carboxamide |
| 060 | rac-3-[4-[4-(pentafluoro-lambda6-sulfanyl) phenyl] sulfonylmorpholin-2-yl]benzothiophene-2-carboxamide |
| 061 | rac-3-[4-butylsulfonylmorpholin-2-yl]benzothiophene-2-carboxamide |
| 062 | rac-3-[4-(3-cyanophenyl)sulfonylmorpholin-2-yl]benzothiophene-2-carboxamide |
| 063 | rac-methyl 4-[2-(2-carbamoylbenzothiophen-3-yl)morpholin-4-yl]sulfonylbenzoate |
| 064 | rac-tert-butyl 4-[2-(2-carbamoylbenzothiophen-3-yl)morpholin-4-yl]sulfonylpiperidine-1-carboxylate |
| 065 | rac-3-[4-(4-nitrophenyl)sulfonylmorpholin-2-yl] benzothiophene-2-carboxamide |
| 066 | rac-3-[4-[2-(trifluoromethyl)phenyl] sulfonylmorpholin-2-yl]benzothiophene-2-carboxamide |
| 067 | rac-3-[4-[2-(trifluoromethoxy)phenyl] sulfonylmorpholin-2-yl]benzothiophene-2-carboxamide |
| 068 | rac-3-[4-(4-hydroxyphenyl)sulfonylmorpholin-2-yl]benzothiophene-2-carboxamide |
| 069 | rac-3-[4-(4-isopropoxyphenyl)sulfonylmorpholin-2-yl]benzothiophene-2-carboxamide |
| 070 | 3-[(S) or (R)-4-[(2-methyl-1,3-benzoxazol-6-yl) sulfonyl]morpholin-2-yl]benzothiophene-2-carboxamide |
| 071 | 3-[(R) or (S)-4-[(2-methyl-1,3-benzoxazol-6-yl) sulfonyl]morpholin-2-yl]benzothiophene-2-carboxamide |
| 072 | 3-[(S) or (R)-4-(3-fluoro-4-methyl-phenyl) sulfonylmorpholin-2-yl]benzothiophene-2-carboxamide |
| 073 | 3-[(R) or (S)-4-(3-fluoro-4-methyl-phenyl) sulfonylmorpholin-2-yl]benzothiophene-2-carboxamide |
| 074 | rac-1,1-dioxo-3-[4-[3-fluoro-4-(trifluoromethyl) phenyl]sulfonylmorpholin-2-yl]benzothiophene-2-carboxamide |
| 075 | 3-[4-(3,5-dimethyl-isoxazole-4-sulfonyl)-morpholin-2-yl]-benzo[b]thiophene-2-carboxylic acid methylamide |
| 076 | 3-[4-(1-methyl-1H-pyrazole-4-sulfonyl)-morpholin-2-yl]-benzo[b]thiophene-2-carboxylic acid isopropylamide |
| 077 | 3-[4-(cyclopentylsulfonyl)-2-morpholinyl]-N-isopropyl-1-benzothiophene-2-carboxamide |

| | |
|---|---|
| 078 | 3-[4-(cyclopentylsulfonyl)-2-morpholinyl]-N,N-dimethyl-1-benzothiophene-2-carboxamide |
| 079 | 3-{4-[(1,5-dimethyl-1H-pyrazol-4-yl)sulfonyl]-2-morpholinyl}-N,N-dimethyl-1-benzothiophene-2-carboxamide |
| 080 | N-(2-hydroxyethyl)-3-[4-(phenylsulfonyl)-2-morpholinyl]-1-benzothiophene-2-carboxamide |
| 081 | 3-(4-cyclopentanesulfonyl-morpholin-2-yl)-benzo[b]thiophene-2-carboxylic acid methylamide |
| 082 | 3-{4-[(2-fluoro-5-methylphenyl)sulfonyl]-2-morpholinyl}-N-methyl-1-benzothiophene-2-carboxamide |
| 083 | 3-{4-[(3,5-dimethyl-1H-pyrazol-4-yl)sulfonyl]-2-morpholinyl}-N,N-dimethyl-1-benzothiophene-2-carboxamide |
| 084 | 3-(4-cyclopentylsulfonylmorpholin-2-yl)benzothiophene-2-carboxamide |
| 085 | N-methyl-3-(4-morpholinosulfonylmorpholin-2-yl)benzothiophene-2-carboxamide |
| 087 | 3-[4-(benzenesulfonyl)morpholin-2-yl]-N-isopropyl-benzothiophene-2-carboxamide |
| 088 | 3-[4-(4-fluorophenyl)sulfonylmorpholin-2-yl]-N-methyl-benzothiophene-2-carboxamide |
| 089 | N,N-dimethyl-3-[4-(1-methyipyrazol-4-yl) sulfonylmorpholin-2-yl]benzothiophene-2-carboxamide and |
| 090 | 3-[4-(3,5-dimethylisoxazol-4-yl)sulfonylmorpholin-2-yl]-N,N-dimethyl-benzothiophene-2-carboxamide. |

In the following, the present invention shall be illustrated by means of some examples, which are not construed to be viewed as limiting the scope of the invention.

The following abbreviations are hereinafter used in the accompanying examples: acetic acid (AcOH), aryl (Ar), apparent triplet (app-t), apparent doublet of triplet (app-dt), apparent doublet (app-d), apparent singlet (app-s), aqueous (aq.), atmospheres (atm), benzyl (Bn), broad signal (bs), tert-butyl (tBu), tert-butylmethyl ether (TBME); normal-butyl lithium (nBuLi), calculated (calcd), carbon nuclear magnetic resonance spectroscopy (13C NMR), m-chloro perbenzoic acid (m-CPBA), cyclohexane (CyH or Cy), Deuterium (D), doublet (d), dichloromethane (DCM), doublet of doublet (dd), doublet of doublet of triplets (ddt), diisopropyl azodicarboxylate (DIAD), ethyldiisopropylamine (DIPEA), doublet of quartet (dq), N, N-dimethylformamide (DMF), dimethyl sulfoxide (DMSO), hexadeuterodimethyl sulfoxide (DMSO-$d_6$), doublet of triplet (dt), N-(3-dimethylamino propyl)-N'-ethylcarbodiimide (EDC), half maximal effective concentration (EC50), equivalents (equiv. or eq.), enantiomeric excess (e.e.), electrospray ionization (ESI), ethyl (Et), diethyl ether (Et$_2$O), ethyl acetate (EtOAc), hour (h), proton nuclear magnetic resonance spectroscopy ($^1$H NMR), 1-[bis(dimethylamino)methylene]-1H-1, 2, 3-triazolo[4,5-b] pyridinium 3-oxid hexafluorophosphate (HATU), 1-hydroxybenzotriazole hydrate (HOBt), high performance liquid chromatography (HPLC), hertz (Hz), infrared spectroscopy (IR), half maximal inhibitory concentration (IC50), coupling constant (J), potassium carbonate (K$_2$CO$_3$), liter (L), lithium hydroxide (LiOH), molarity (M), multiplet (m), methyl (Me), (MeOH), milligram (mg), acetonitrile (MeCN), methanol megahertz (MHz), minutes (min), milliliter (mL), millimole (mmol), Mass Spectrometry (MS), molecular weight (MW), sodium hydride (NaH), sodium bicarbonate (NaHCO$_3$), sodium carbonate (Na$_2$CO$_3$), sodium sulphate (Na$_2$SO$_4$), ammonium chloride (NH$_4$Cl), not determined (nd), nanomolar (nM), Nuclear Magnetic Resonace (NMR), protecting group (Pg), parts per million (ppm), triphenylphospine (PPh$_3$), isopropyl (i-Pr), quartet (q), substituent (R), racemic (rac-), room temperature (rt), singlet(s), temperature (T), triplet or time (t), retention time (tr), triethylamine (TEA or Et$_3$N), trifluoroacetic acid (TFA), tetrahydrofuran (THF), thin-layer chromatography (TLC), ultraviolet (UV), Ultra-Performance Liquid Chromotography-Mass Spectroscopy (UPLC-MS), anionic ligand, halide, substituent, or number (X), chemical shift (δ), microliter (μL), micromolar (μM), Watt (W).

Chemicals, Materials and Methods

Solvents and reagents were obtained from commercial suppliers and were used without further purification.

Automated column chromatography purifications were performed on Teledyne ISCO apparatus (CombiFlash® Rf) with pre-packed silica gel columns of different sizes (Re-disep). Hydrogenation reactions were performed on H-Cube® continuous hydrogenation equipment (SS-reaction line version), employing disposable catalyst cartridges (CatCart®) preloaded with the required heterogeneous catalyst. NMR experiments were run on a Bruker Avance III 400 system (400.13 MHz for 1H, and 100.62 MHz for 13C), equipped with a BBI probe and Z-gradients and Bruker FT NMR Avance III 600 MHz spectrometer equipped with a 5 mm CryoProbe™ QCI $^1$H/$^{19}$F-$^{13}$C/$^{15}$N-D quadruple resonance, a shielded z-gradient coil and the automatic sample changer SampleJet™ NMR system (600 MHz for $^1$H, 151 MHz for $^{13}$C and 565 MHz for $^{19}$F). Chemical shifts for $^1$H and $^{13}$C spectra were recorded in parts per million using the residual non-deuterated solvent as the internal standard (for CDCl$_3$:7.26 ppm, $^1$H and 77.16 ppm, $^{13}$C; for DMSO-d$_6$: 2.50 ppm, $^1$H; 39.52 ppm, $^{13}$C, for D$_2$O: TSP as internal standard 0.00 ppm).

The analyses by UPLC/MS were run on a Waters ACQUITY UPLC/MS system consisting of a SQD (Single Quadrupole Detector) Mass Spectrometer equipped with an Electrospray Ionization interface and a Photodiode Array Detector. The PDA range was 210-400 nm. The analyses were performed on either an ACQUITY UPLC HSS T3 C$_{18}$ column (50×2. 1 mmID, particle size 1.8 μm) with a VanGuard HSS T3 C$_{18}$ pre-column (5×2. 1 mmID, particle size 1.8 μm) (LogD<1) or an ACQUITY UPLC BEH C$_{18}$ column (50×2.1 mmID, particle size 1.7 μm) with a VanGuard BEH C$_{18}$ pre-column (5×2. 1 mmID, particle size 1.7 μm) (LogD>1).

The mobile phase was 10 mM NH$_4$OAc in H$_2$O at pH 5 adjusted with AcOH (A) and 10 mM NH$_4$OAc in MeCN—H$_2$O (95:5) at pH 5 (B).

Electrospray ionization in positive and negative mode was applied in the mass scan range 100-650 Da or 150-750 Da.

Analyses were performed either with "Polar method", "Generic method" and "Apolar Method" herein reported:

Polar Method:
- Column: Waters ACQUITY UPLC HSS T3 $C_{18}$/1.8 μm, 50×2.1 mmID
- Pre-column: VanGuard HSS T3 $C_{18}$, 1.8 μm, 5×2.1 mmID
- Linear gradient: 0-0.2 min: 0% B, 0.2-2.7 min: 0-50% B, 2.7-2.8 min: 50-100% B, 2.8-3.0 min: 100% B
- Flow rate: 0.5 mL/min Generic Method:
- Column: Waters ACQUITY UPLC BEH $C_{18}$, 1.7 μm, 50×2.1 mmID
- Pre-column: VanGuard BEH $C_{18}$, 1.7 μm, 5×2.1 mmID
- Linear gradient: 0-0.2 min: 5% B, 0.2-2.7 min: 5-95% B, 2.7-2.8 min: 95-100% B, 2.8-3.0 min: 100% B
- Flow rate: 0.5 mL/min Apolar Method:
- Column: Waters ACQUITY UPLC BEH $C_{18}$, 1.7 μm, 50×2.1 mmID
- Pre-column: VanGuard BEH $C_{18}$, 1.7 μm, 5×2.1 mmID
- Gradient: 0-0.2 min: 50% B, 0.2-2.7 min: 50-100% B, 2.7-3.0 min: 100% B
- Flow rate: 0.5 mL/min The chiral separations by HPLC were run on a Waters Alliance HPLC instrument consisting of an e2695 Separation Module and a 2998 Photodiode Array Detector. The PDA range was 210-400 nm. The analyses were performed in isocratic mode on a Daicel ChiralCel OD-H column (250×4.6 mmID, particle size 5 μm) at 25° C.

Synthesis of
3-morpholin-2-ylbenzothiophene-2-carboxamide
(Int-1.6)

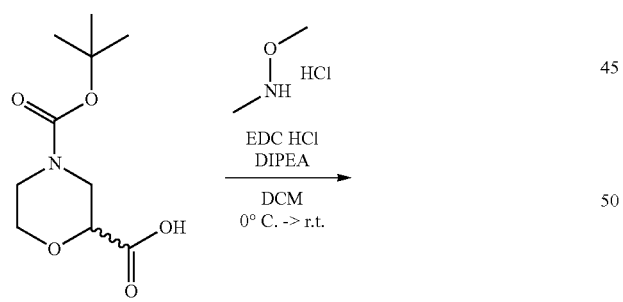

[Int-1.1]

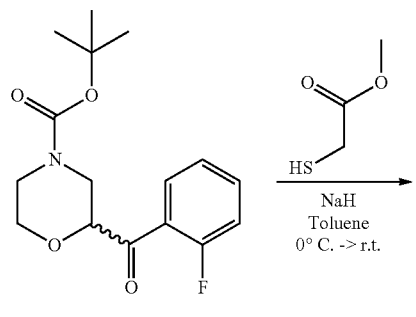

[Int-1.2]

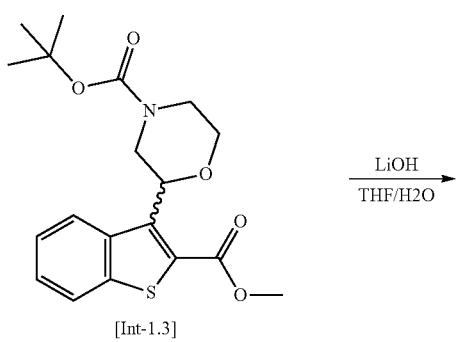

[Int-1.3]

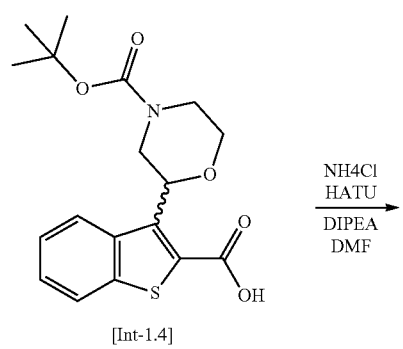

[Int-1.4]

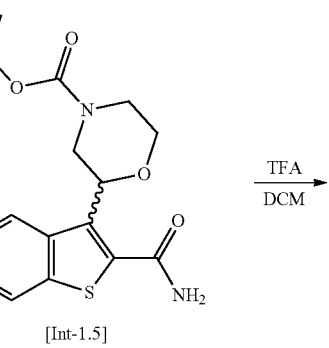

[Int-1.5]

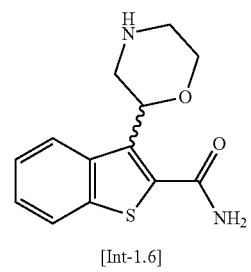

[Int-1.6]

-continued

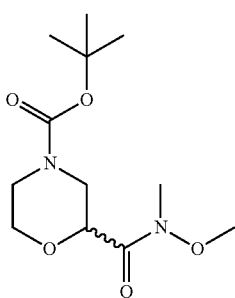

[Int-1.1]

[Int-1.1] tert-Butyl 2-[methoxy(methyl) carbamoyl] morpholine-4-carboxylate: To a solution of 4-tert-butoxycarbonylmorpholine-2-carboxylic acid (2.0 g, 8.65 mmol) in dry DCM (40 mL) at 0° C., HOBt (0.257 g, 1.90 mmol) and DIPEA (3.32 mL, 19.03 mmol) were added. After 20 minutes N, O-dimethylhydroxylamine hydrochloride (0.928 g, 9.51 mmol) and EDC hydrochloride (1.824 g, 9.51 mmol) were added and the mixture was stirred at room temperature for 72 h. The reaction was diluted with DCM (40 mL) and then organic phase was washed with water (30 mL), sat. aq. NH$_4$Cl (30 mL) and brine (30 mL). Organic layer was dried with Na$_2$SO$_4$, filtered and solvent evaporated. Crude compound was purified by silica gel flash-column chromatography, eluting with gradient from 0% to 80% of TBME in Cyclohexane. The title compound was isolated as a viscous oil (1.95 g, 7.14 mmol, 82%): $^1$H NMR (400 MHz, DMSO-d$_6$) δ 4.26 (d, J=9.5 Hz, 1H), 3.95-3.78 (m, 2H), 3.70 (s, 3H), 3.64 (s, 1H), 3.48 (td, J=11.2, 3.0 Hz, 1H), 3.12 (s, 3H), 2.98 (t, J=11.2 Hz, 2H), 1.41 (s, 9H). UPLC-MS: t$_R$=1.68 min (Generic method); MS (ESI) m/z calcd for C$_{12}$H$_{21}$N$_2$O$_5$ (M+H)$^+$: 275.1, found: 275.

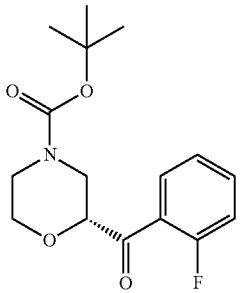

[Int-1.2]

[Int-1.2] tert-Butyl 2-(2-fluorobenzoyl) morpholine-4-carboxylate: In a flame dried flask, 1-bromo-2-fluorobenzene (0.641 mL, 5.83 mmol) was dissolved in dry THF (40 mL) and the mixture was cooled to −78° C. n-BuLi 1.6M in THF (4.734 mL, 7.58 mmol) was added dropwise. Mixture was stirred for 1 h and a solution of Int-1.1 (1.6 g, 5.83 mmol), dissolved in dry THF (5.0 mL), was added dropwise, maintaining temperature at −78° C. After 2 h the mixture was quenched with sat. aq. NH$_4$Cl and EtOAc was added (20 mL). Layers were separated, and aqueous layer was extracted with EtOAc (2×20 mL). Organics were washed with brine, dried with Na$_2$SO$_4$, filtered and the solvent evaporated. The crude product was purified by silica gel flash-column chromatography, eluting with gradient from 0% to 40% of EtOAc in cyclohexane. Fractions containing products were collected, and the solvent evaporated. The afforded oil was stripped with Et$_2$O and dried under vacuum. The title compound was isolated as an oil (1.2 g, 66%): $^1$H NMR (400 MHz, DMSO-d$_6$) δ 7.81-7.71 (m, 1H), 7.73-7.62 (m, 1H), 7.38-7.31 (m, 1H), 7.25-7.14 (m, 1H), 4.67 (d, J=9.1 Hz, 1H), 4.02-3.75 (m, 2H), 3.68-3.45 (m, 2H), 3.05 (ddd, J=14.7, 9.1, 2.9 Hz, 1H), 2.29 (s, 1H), 1.38 (s, 9H). UPLC-MS: t$_R$=2.28 min (Generic method); MS (ESI) m/z calcd for C$_{16}$H$_{21}$FNO$_4$ (M+H)$^+$: 309, found: 310.

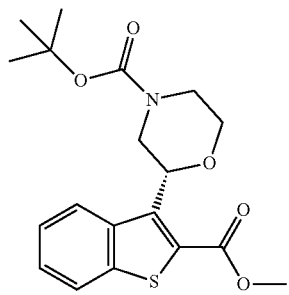

[Int-1.3]

[Int-1.3] tert-Butyl 2-(2-methoxycarbonylbenzothiophen-3-yl) morpholine-4-carboxylate: In a flame dried flask, methyl thioglycolate (0.45 mL, 5.04 mmol) was dissolved in dry toluene at 0° C. under N$_2$ atmosphere, and NaH (0.464 g, 11.6 mmol) was added portion wise. The reaction mixture was stirred at room temperature for 30 min, then cooled to 0° C. Int-1.2 (1.2 g, 3.88 mmol) was added and the mixture stirred at 40° C. for 3 hours, then left stirring at room temperature overnight. Upon full conversion of the starting material, the reaction was quenched with aq. 1M HCl until pH=7 then extracted with EtOAc. The organic layer was washed with brine, dried, filtered and concentrated. The crude product was purified by silica gel flash-column chromatography, eluting with EtOAc in cyclohexane from 0% to 30%. The title compound was isolated as a pale yellow oil (0.82 g, 56%): $^1$H NMR (400 MHz, DMSO-d$_6$) δ 8.52 (d, J=8.3 Hz, 1H), 8.05 (d, J=8.1 Hz, 1H), 7.55 (td, J=8.2, 1.2 Hz, 1H), 7.46 (td, J=8.2, 1.2 Hz, 1H), 5.62 (d, J=10.8 Hz, 1H), 4.03 (dd, J=8.2, 1.2 Hz, 2H), 3.90 (s, 3H), 3.57 (t, J=11.8 Hz, 1H), 1.44 (s, 9H). UPLC-MS: t$_R$=2.79 min (Generic method); MS (ESI) m/z calcd for C$_{19}$H$_{24}$NO$_5$S (M+H)$^+$: 378.1, found: 378.

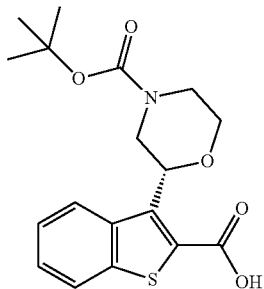

[Int-1.4]

[Int-1.4] 3-(4-tert-Butoxycarbonylmorpholin-2-yl) benzothiophene-2-carboxylic acid: To a solution of Int-1.3 (0.330 g, 0.86 mmol) in THF (10 mL), aqueous solution of LiOH (1N, 3.0 mL) was added dropwise and the reaction was stirred at room temperature overnight. The reaction was quenched upon addition of aq. 2M HCl until pH=4/5.

Aqueous layer was extracted with DCM (3×10 mL). The combined organic layers were washed with brine, dried, filtered and solvent evaporated. The crude compound was purified by silica gel flash-column chromatography, eluting with DCM/MeOH 95:5 with 5% AcOH. The title compound was isolated as a white powder (0.311 g, quantitative): $^1$H NMR (400 MHz, DMSO-$d_6$) δ 8.48 (d, J=8.2 Hz, 1H), 8.00 (d, J=8.0 Hz, 1H), 7.50 (ddd, J=8.2, 7.0, 1.2 Hz, 1H), 7.42 (ddd, J=8.2, 7.0, 1.2 Hz, 1H), 5.66 (dd, J=10.9, 2.9 Hz, 1H), 4.04 (dd, J=11.5, 3.1 Hz, 1H), 3.97-3.81 (m, 2H), 3.63-3.50 (m, 2H), 1.82-1.67 (m, 2H). UPLC-MS: $t_R$=1.79 min (Generic method); MS (ESI) m/z calcd for $C_{18}H_{20}NO_5S$ (M−H)$^−$: 362.1, found: 362.

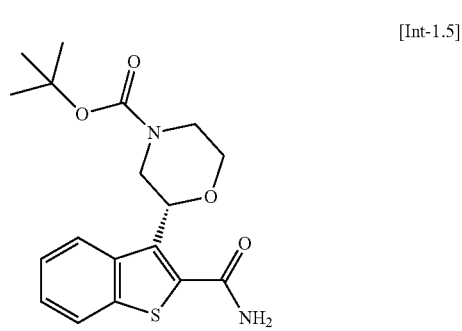 [SMILES: CC(C)(C)OC(=O)N1CCO[C@H](c2c(C(N)=O)sc3ccccc23)C1]

[Int-1.5]

[Int-1.5] tert-Butyl 2-(2-carbamoylbenzothiophen-3-yl) morpholine-4-carboxylate: To a solution of Int-1.4 (0.300 g, 0.85 mmol) in dry DMF (5.0 mL) at 0° C., HATU (0.470 g, 1.24 mmol) and DIPEA (0.316 mL, 3.30 mmol) were added. After 10 minutes NH$_4$Cl (0.088 g, 1.65 mmol) was added to the solution and the mixture left stirring overnight at room temperature. The reaction was treated with sat. aq. NH$_4$Cl and the mixture was extracted with EtOAc (3×15 mL). The organic layers were washed with brine, dried with Na$_2$SO$_4$ filtered and evaporated. The crude product was purified by silica gel flash-column chromatography, eluting with a gradient from 0% to 40% of EtOAc in DCM to afford the title product (0.313 g, 96%): $^1$H NMR (400 MHz, DMSO-$d_6$) δ 8.52 (dt, J=8.1, 1.0 Hz, 1H), 8.06 (dt, J=8.1, 1.0 Hz, 1H), 7.56 (ddd, J=8.3, 7.0, 1.2 Hz, 1H), 7.47 (ddd, J=8.3, 7.1, 1.2 Hz, 1H), 5.63 (dd, J=10.8, 2.9 Hz, 1H), 4.07 (dd, J=11.7, 3.2 Hz, 1H), 4.01-3.94 (m, 2H), 3.91 (s, 3H), 3.58 (td, J=11.8, 2.7 Hz, 1H), 3.20 (bs, 2H), 1.45 (s, 9H). UPLC-MS: $t_R$=2.27 min (Generic method); MS (ESI) m/z calcd for $C_{18}H_{23}N_2O_4S$ (M−H)$^−$: 363.1, found: 363.

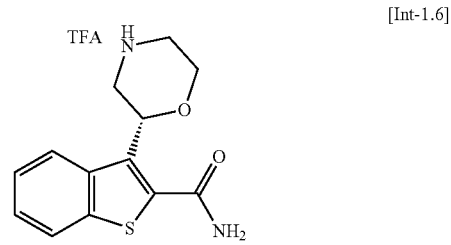 [SMILES: NC(=O)c1sc2ccccc2c1[C@@H]1CNCCO1]

[Int-1.6]

[Int-1.6] 3-Morpholin-2-ylbenzothiophene-2-carboxamide trifluoroacetate: To a solution of Int-1.5 (0.313 g, 0.86 mmol) in dry DCM at 0° C., TFA (0.282 mL, 4.32 mmol) was slowly added. The reaction was allowed to stir overnight at room temperature. The reaction mixture was evaporated under reduced pressure. The crude compound was purified with preparative LC/MS to obtain the title compound as a white powder (0.2 g, 89%). $^1$H NMR (400 MHz, DMSO-$d_6$) δ 8.32 (dd, J=8.2, 1.1 Hz, 1H), 8.16-8.03 (m, 1H), 7.97 (dd, J=8.2, 1.1 Hz, 1H), 7.82-7.67 (m, 1H), 7.48-7.39 (m, 1H), 5.32 (dd, J=10.5, 2.8 Hz, 1H), 3.96 (dd, J=11.1, 3.0 Hz, 1H), 3.61-3.60 (m, 1H), 3.03 (dd, J=12.4, 10.5 Hz, 1H), 2.88 (dq, J=24.2, 12.1, 11.5, 2.6 Hz, 2H). UPLC-MS: $t_R$=1.25 min (Generic method); MS (ESI) m/z calcd for $C_{13}H_{15}N_2O_2S$ (M+H)$^+$: 263.1, found: 263.

General Protocol for Sulfonyl Amide Synthesis (GP1).

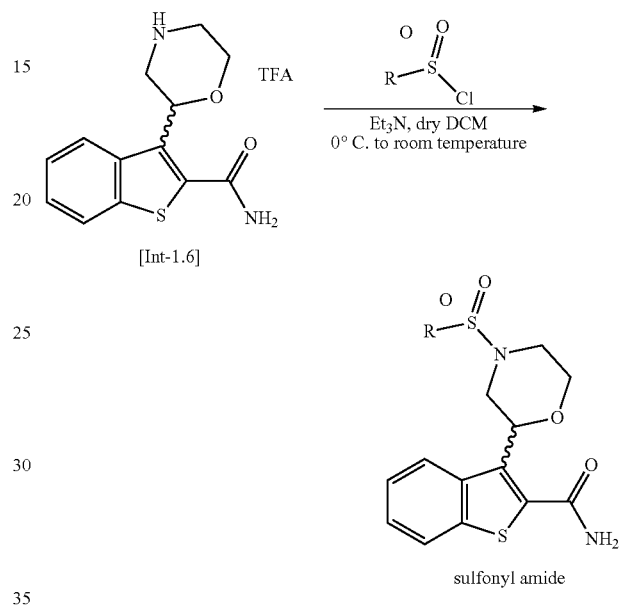

sulfonyl amide

In a round-bottomed flask, under nitrogen, Int-1.6 (1.1 eq) was dissolved in dry DCM (0.25M) and Et$_3$N (1.2 eq) was added. The sulfonyl chloride (1.0 eq) was added and the mixture was stirred until UPLC-MS analysis showed completion of the reaction (from 10 min to 1h). The reaction mixture was quenched with water, layers were separated and the organic layer was washed with brine, dried over Na$_2$SO$_4$, filtered and concentrated. Desired compounds were afforded in moderate to good yields after purification by silica gel flash-column chromatography.

3-[4-(4-Fluoro-3-methyl-phenyl) sulfonylmorpholin-2-yl] benzothiophene-2-carboxamide: The title compound was prepared following GP1, from Int-1.6 (0.06 g, 0.16 mmol) and (4-fluoro-3-methyl-phenyl) sulfonyl chloride (0.03 g, 0.14 mmol). The product was obtained, after purification by silica gel flash-column chromatography with DCM/EtOAc as the eluent, as a white solid (0.05 g, 74%). $^1$H NMR (400 MHz, DMSO-$d_6$) δ 8.14 (d, J=8.2, 1.1 Hz, 1H), 8.09-7.93 (m, 2H), 7.87-7.72 (m, 2H), 7.69-7.60 (m, 1H), 7.49-7.32 (m, 3H), 5.51 (dd, J=10.5, 2.8 Hz, 1H), 4.11 (d, J=11.6, 2.9 Hz, 1H), 3.85-3.56 (m, 3H), 2.67 (td, J=10.9, 3.7 Hz, 2H), 2.32 (s, 3H). UPLC-MS: $t_R$=2.33 min (Generic method); MS (ESI) m/z calcd for $C_{20}H_{20}FN_2O_4S_2$ (M+H)$^+$: 435.1, found: 435.

3-[4-(1,2-Dimethylimidazol-4-yl) sulfonylmorpholin-2-yl] benzothiophene-2-carboxamide: The title compound was prepared following GP1, from Int-1.6 (0.03 g, 0.1 mmol) and (1,2-dimethylimidazol-4-yl) sulfonyl chloride (0.02 g, 0.09 mmol). The product was obtained, after purification by silica gel flash-column chromatography with Cyclohexane/EtOAc as the eluent, as a white solid (0.03 g, 79%). $^1$H NMR (400 MHz, DMSO-d$_6$) δ 8.19 (d, J=8.1 Hz, 1H), 8.10-7.95 (m, 2H), 7.77 (bs, 1H), 7.75 (s, 1H), 7.47 (ddd, J=8.2, 7.0, 1.3 Hz, 1H), 7.41 (ddd, J=8.2, 7.0, 1.3 Hz, 1H), 5.49 (dd, J=10.7, 2.8 Hz, 1H), 4.13 (dd, J=11.5, 2.9 Hz, 1H), 3.73 (td, J=11.7, 2.5 Hz, 1H), 3.68-3.51 (m, 5H), 2.91 (t, J=11.2 Hz, 1H), 2.83 (td, J=11.9, 3.3 Hz, 1H), 2.30 (s, 3H). UPLC-MS: t$_R$=1.68 min (Generic method); MS (ESI) m/z calcd for C$_{18}$H$_{21}$N$_4$O$_4$S$_2$ (M+H)$^+$: 421.1, found: 421.

3-[4-(Benzenesulfonyl) morpholin-2-yl]benzothiophene-2-carboxamide: The title compound was prepared following GP1, from Int-1.6 (0.03 g, 0.09 mmol) and benzensulfonyl chloride (10.8 µL, 0.08 mmol). The product was obtained, after purification by silica gel flash-column chromatography with Cyclohexane/EtOAc as the eluent, as a white solid (0.03 g, 99%). $^1$H NMR (400 MHz, DMSO-d$_6$) δ 8.09 (d, J=8.2 Hz, 1H), 8.01-7.96 (m, 2H), 7.81-7.71 (m, 4H), 7.65 (t, J=7.6 Hz, 2H), 7.43 (ddd, J=8.2, 7.0, 1.2 Hz, 1H), 7.33 (ddd, J=8.2, 7.1, 1.2 Hz, 1H), 5.52 (dd, J=10.5, 2.8 Hz, 1H), 4.11 (dd, J=11.5, 2.9 Hz, 1H), 3.85-3.58 (m, 3H), 2.60 (dd, J=12.2, 9.7 Hz, 2H). UPLC-MS: t$_R$=2.13 min (Generic method); MS (ESI) m/z calcd for C$_{19}$H$_{19}$N$_2$O$_4$S$_2$ (M+H)$^+$: 403.1, found: 403.

3-[4-(1H-Imidazol-4-ylsulfonyl) morpholin-2-yl] benzothiophene-2-carboxamide: The title compound was prepared following GP1, from Int-1.6 (0.03 g, 0.10 mmol) and 1H-imidazol-4-yl-sulfonyl chloride (0.02 g, 0.09 mmol). The product was obtained, after purification by silica gel flash-column chromatography with cyclohexane/EtOAc as the eluent, as a white solid (0.02 g, 46%). $^1$H NMR (400 MHz, DMSO-d$_6$) δ 12.92 (s, 1H), 8.14 (d, J=8.1 Hz, 1H), 8.02-7.96 (m, 2H), 7.90 (s, 1H), 7.82 (s, 1H), 7.77 (bs, 1H), 7.46 (ddd, J=8.2, 7.1, 1.3 Hz, 1H), 7.39 (ddd, J=8.2, 7.1, 1.2 Hz, 1H), 5.50 (dd, J=10.7, 2.8 Hz, 1H), 4.13 (dd, J=11.7, 2.9 Hz, 1H), 3.85-3.50 (m, 3H), 2.90-2.72 (m, 2H). UPLC-MS: t$_R$=1.57 min (Generic method); MS (ESI) m/z calcd for C$_{16}$H$_{17}$N$_4$O$_4$S$_2$ (M+H)$^+$: 393.1, found: 393.

3-[4-(3-Thienylsulfonyl) morpholin-2-yl] benzothiophene-2-carboxamide: The title compound was prepared following GP1, from Int-1.6 (0.03 g, 0.10 mmol) and 3-thienylsulfonyl chloride (0.02 g, 0.09 mmol). The product was obtained, after purification by silica gel flash-column chromatography with DCM/MeOH as the eluent, as a white solid (0.02 g, 64%). $^1$H NMR (400 MHz, DMSO-d$_6$) δ 8.13 (d, J=8.1 Hz, 1H), 8.10-8.00 (m, 3H), 7.89-7.80 (bs, 1H), 7.69 (dd, J=3.7, 1.3 Hz, 1H), 7.45 (ddd, J=8.2, 7.0, 1.2 Hz, 1H), 7.37 (ddd, J=8.3, 7.1, 1.2 Hz, 1H), 7.29 (dd, J=5.0, 3.8 Hz, 1H), 5.55 (dd, J=10.5, 2.8 Hz, 1H), 4.16 (dd, J=10.5, 2.8 Hz, 1H), 3.76 (dt, J=11.5, 2.9 Hz, 2H), 3.64 (d, J=11.8 Hz, 1H), 2.75-2.61 (m, 2H). UPLC-MS: t$_R$=2.10 min (Generic method); MS (ESI) m/z calcd for C$_{17}$H$_{17}$N$_2$O$_4$S$_3$ (M+H)$^+$: 409.0, found: 409.

3-[4-(4-Phenoxyphenyl) sulfonylmorpholin-2-yl] benzothiophene-2-carboxamide: The title compound was prepared following GP1, from Int-1.6 (0.02 g, 0.08 mmol) and (4-phenoxyphenyl) sulfonyl chloride (0.02 g, 0.07 mmol). The product was obtained, after purification by silica gel flash-column chromatography with DCM/MeOH as the eluent, as a white solid (0.03 g, 96%). $^1$H NMR (400 MHz, DMSO-d$_6$) δ 8.13 (d, J=8.1, 1.0 Hz, 1H), 8.08-7.99 (m, 2H), 7.89-7.72 (m, 3H), 7.55-7.42 (m, 3H), 7.37 (ddd, J=8.2, 7.1, 1.2 Hz, 1H), 7.29 (ddd, J=8.2, 7.1, 1.2 Hz, 1H), 7.21-7.10 (m, 4H), 5.52 (dd, J=10.5, 2.8 Hz, 1H), 4.11 (d, J=11.7 Hz, 1H), 3.83-3.67 (m, 3H), 3.62 (d, J=11.7 Hz, 1H), 2.73-2.56 (m, 2H). UPLC-MS: t$_R$=2.55 min (Generic method); MS (EST) m/z calcd for C$_{25}$H$_{23}$N$_2$O$_5$S$_2$ (M+H)$^+$: 495.1, found: 495.

Methyl 3-[2-(2-carbamoylbenzothiophen-3-yl) morpholin-4-yl]sulfonylbenzoate: The title compound was prepared following GP1, from Int-1.6 (0.02 g, 0.08 mmol) and methyl 3-chlorosulfonylbenzoate (0.02 g, 0.07 mmol). The product was obtained, after purification by silica gel flash-column chromatography with DCM/MeOH as the eluent, as a white solid (0.03 g, 83%). $^1$H NMR (400 MHz, DMSO-d$_6$) δ 8.29 (dt, J=7.9, 1.3 Hz, 1H), 8.22 (t, J=1.8 Hz, 1H), 8.11 (dd, J=8.3, 1.1 Hz, 1H), 8.09-7.97 (m, 3H), 7.81 (t, J=7.9 Hz, 1H), 7.78 (bs, 1H), 7.43 (ddd, J=8.2, 7.1, 1.2 Hz, 1H), 7.33 (ddd, J=8.2, 7.1, 1.1 Hz, 1H), 5.51 (dd, J=10.5, 2.8 Hz, 1H), 4.12 (d, J=11.2 Hz, 1H), 3.90 (s, 3H), 3.80 (d, J=11.2 Hz, 1H), 3.76-3.63 (m, 2H), 2.80-2.59 (m, 2H). UPLC-MS: t$_R$=2.16 min (Generic method); MS (ESI) m/z calcd for C$_{21}$H$_{21}$N$_2$O$_6$S$_2$ (M+H)$^+$: 461.1, found: 461.

3-[4-(3,5-Dimethylisoxazol-4-yl) sulfonylmorpholin-2-yl] benzothiophene-2-carboxamide: The title compound was prepared following GP1, from Int-1.6 (0.03 g, 0.10 mmol) and (3,5-dimethylisoxazol-4-yl) sulfonyl chloride (0.02 g, 0.08 mmol). The product was obtained, after purification by silica gel flash-column chromatography with DCM/MeOH as the eluent, as a white solid (0.04 g, 97%). $^1$H NMR (400 MHz, DMSO-d$_6$) δ 8.29 (d, J=8.0, 1.0 Hz, 1H), 8.08-7.95 (m, 2H), 7.80 (bs, 1H), 7.47 (ddd, J=8.2, 7.1, 1.3 Hz, 1H), 7.41 (ddd, J=8.2, 7.1, 1.3 Hz, 1H), 5.49 (dd, J=10.5, 2.8 Hz, 1H), 4.14 (d, J=11.7 Hz, 1H), 3.81-3.67 (m, 2H), 3.63 (d, J=11.7 Hz, 1H), 3.14-2.95 (m, 2H), 2.60 (s, 3H), 2.32 (s, 3H). UPLC-MS: t$_R$=2.07 min (Generic method); MS (ESI) m/z calcd for C$_{18}$H$_{20}$N$_3$O$_5$S$_2$ (M+H)$^+$: 422.1, found: 422.

3-[4-(3-Bromophenyl) sulfonylmorpholin-2-yl] benzothiophene-2-carboxamide: The title compound was prepared following GP1, from Int-1.6 (0.02 g, 0.08 mmol) and (3-bromophenyl) sulfonyl chloride (0.02 g, 0.07 mmol). The product was obtained, after purification by silica gel flash-column chromatography with DCM/MeOH as the eluent, as a white solid (0.03 g, 81%). $^1$H NMR (400 MHz, DMSO-d$_6$) δ 8.15 (dd, J=8.2, 1.1 Hz, 1H), 8.08-8.00 (m, 2H), 7.99-7.88 (m, 1H), 7.87-7.70 (m, 3H), 7.60 (t, J=7.9 Hz, 1H), 7.45 (ddd, J=8.2, 7.0, 1.2 Hz, 1H), 7.36 (ddd, J=8.3, 7.1, 1.2 Hz, 1H), 5.51 (dd, J=10.6, 2.8 Hz, 1H), 4.11 (d, J=11.2 Hz, 1H), 3.81 (d, J=11.2 Hz, 1H), 3.77-3.53 (m, 2H), 2.71 (td, J=11.6, 11.1, 3.2 Hz, 2H). UPLC-MS: t$_R$=2.34 min (Generic method); MS (ESI) m/z calcd for C$_{19}$H$_{18}$BrN$_2$O$_4$S$_2$ (M+H)$^+$: 481. 0, found: 481.

3-[4-(4-Methoxyphenyl) sulfonylmorpholin-2-yl]benzothiophene-2-carboxamide: The title compound was prepared following GP1, from Int-1.6 (0.03 g, 0.10 mmol) and (4-methoxyphenyl) sulfonyl chloride (0.02 g, 0.09 mmol). The product was obtained, after purification by silica gel flash-column chromatography with DCM/MeOH as the eluent, as a white solid (0.03 g, 89%). $^1$H NMR (400 MHz, DMSO-d$_6$) δ 8.11 (dt, J=8.2, 1.0 Hz, 1H), 8.08-7.95 (m, 2H), 7.78 (bs, 1H), 7.70 (dt, J=8.2, 1.2 Hz, 2H), 7.44 (ddd, J=8.2, 7.0, 1.2 Hz, 1H), 7.35 (ddd, J=8.2, 7.1, 1.2 Hz, 1H), 7.14 (dt, J=8.2, 1.2 Hz, 2H), 5.51 (dd, J=10.5, 2.8 Hz, 1H), 4.11 (d, J=11.8, 2.8 Hz, 1H), 3.86 (s, 3H), 3.80-3.67 (m, 2H), 3.61 (d, J=11.9 Hz, 1H), 2.58 (t, J=10.8 Hz, 3H). UPLC-MS: t$_R$=2.15 min (Generic method); MS (ESI) m/z calcd for C$_{20}$H$_{21}$N$_2$O, S$_2$ (M+H)$^+$: 433.1, found: 433.

3-[4-[4-(Trifluoromethyl)phenyl]sulfonylmorpholin-2-yl] benzothiophene-2-carboxamide: The title compound was prepared following GP1, from Int-1.6 (0.04 g, 0.12 mmol) and (4-trifluoromethylphenyl) sulfonyl chloride (0.04 g, 0.11 mmol). The product was obtained, after purification by silica gel flash-column chromatography with DCM/EtOAc as the eluent, as a white solid (0.05 g, 95%). $^1$H NMR (400 MHz, DMSO-d$_6$) δ 8.15 (dd, J=8.2, 1.0 Hz, 1H), 8.01 (s, 4H), 8.01-7.99 (m, 2H), 7.79 (bs, 1H), 7.44 (ddd, J=8.2, 7.1, 1.2 Hz, 1H), 7.34 (ddd, J=8.2, 7.1, 1.1 Hz, 1H), 5.51 (dd, J=10.5, 2.8 Hz, 1H), 4.11 (d, J=10.9 Hz, 1H), 3.70 (t, J=12.1 Hz, 2H), 3.84 (d, J=11.4 Hz, 1H), 2.83-2.62 (m, 2H). UPLC-MS: $t_R$=2.40 min (Generic method); MS (ESI) m/z calcd for $C_{20}H_{18}F_3N_2O_4S_2$ (M+H)$^+$: 471. 1, found: 471.

3-[4-(m-Tolylsulfonyl) morpholin-2-yl]benzothiophene-2-carboxamide: The title compound was prepared following GP1, from Int-1.6 (0.03 g, 0.10 mmol) and (3-methylphenyl) sulfonyl chloride (0.02 g, 0.09 mmol). The product was obtained, after purification by silica gel flash-column chromatography with DCM/MeOH as the eluent, as a white solid (0.04 g, 99%). $^1$H NMR (400 MHz, DMSO-d$_6$) δ 8.10 (d, J=8.1 Hz, 1H), 8.06-7.97 (m, 2H), 7.88-7.65 (m, 1H), 7.60 (bs, 1H), 7.59-7.48 (m, 3H), 7.44 (ddd, J=8.1, 7.1, 1.2 Hz, 1H), 7.34 (ddd, J=8.2, 7.0, 1.2 Hz, 1H), 5.51 (dd, J=10.5, 2.8 Hz, 1H), 4.10 (d, J=11.3, 2.9 Hz, 1H), 3.86-3.60 (m, 3H), 2.72-2.56 (m, 2H), 2.41 (s, 3H). UPLC-MS: $t_R$=2.25 min (Generic method); MS (ESI) m/z calcd for $C_{20}H_{21}N_2O_4S_2$ (M+H)$^+$: 417.1, found: 417.

3-[4-[4-(2-Oxopyrrolidin-1-yl)phenyl] sulfonylmorpholin-2-yl]benzothiophene-2-carboxamide: The title compound was prepared following GP1, from Int-1.6 (0.02 g, 0.08 mmol) and [4-(2-oxopyrrolidin-1-yl)phenyl]sulfonyl chloride (0.02 g, 0.07 mmol). The product was obtained, after purification by silica gel flash-column chromatography with DCM/MeOH as the eluent, as a white solid (0.01 g, 20%). $^1$H NMR (400 MHz, DMSO-d$_6$) δ 8.11 (d, J=8.2 Hz, 1H), 8.07-7.97 (m, 2H), 7.95-7.90 (m, 2H), 7.86-7.71 (m, 3H), 7.44 (ddd, J=8.2, 7.1, 1.2 Hz, 1H), 7.34 (ddd, J=8.3, 7.1, 1.2 Hz, 1H), 5.52 (dd, J=10.5, 2.7 Hz, 1H), 4.11 (d, J=10.3 Hz, 1H), 3.88 (t, J=7.0 Hz, 2H), 3.82-3.60 (m, 3H), 2.65-2.54 (m, 4H), 2.10 (q, J=7.5 Hz, 2H). UPLC-MS: $t_R$=1.98 min (Generic method); MS (ESI) m/z calcd for $C_{23}H_{24}N_3O_5S_2$ (M+H)$^+$: 486.1, found: 486.

3-(4-Cyclohexylsulfonylmorpholin-2-yl) benzothiophene-2-carboxamide: The title compound was prepared following GP1, from Int-1.6 (0.03 g, 0.09 mmol) and cyclohexylsulfonyl chloride (0.02 g, 0.08 mmol). The product was obtained, after purification by silica gel flash-column chromatography with DCM/MeOH as the eluent, as a white solid (0.02 g, 71%). $^1$H NMR (400 MHz, DMSO-d$_6$) δ 8.37 (d, J=7.5 Hz, 1H), 8.11-7.93 (m, 2H), 7.78 (bs, 1H), 7.47 (td, J=7.2, 1.5 Hz, 2H), 5.42 (dd, J=10.5, 2.9 Hz, 1H), 4.11 (d, J=10.6 Hz, 1H), 3.70-3.55 (m, 3H), 2.04 (dd, J=19.9, 11.3 Hz, 2H), 1.85-1.72 (m, 2H), 1.63 (d, J=12.6 Hz, 1H), 1.46-1.07 (m, 9H). UPLC-MS: $t_R$=2.22 min (Generic method); MS (ESI) m/z calcd for $C_{19}H_{25}N_2O_4S_2$ (M+H)$^+$: 409.1, found: 409.

3-[4-(1,3-Benzodioxol-5-ylsulfonyl) morpholin-2-yl]benzothiophene-2-carboxamide: The title compound was prepared following GP1, from Int-1.6 (0.02 g, 0.07 mmol) and 1,3-benzodioxol-5-ylsulfonyl chloride (0.01 g, 0.06 mmol). The product was obtained, after purification by silica gel flash-column chromatography with DCM/EtOAc as the eluent, as a white solid (0.02 g, 63%). $^1$H NMR (400 MHz, DMSO-d$_6$) δ 8.15 (d, J=8.2, 1.1 Hz, 1H), 8.07-7.95 (m, 2H), 7.78 (bs, 1H), 7.44 (ddd, J=8.2, 7.0, 1.2 Hz, 1H), 7.36 (ddd, J=8.2, 7.1, 1.2 Hz, 1H), 7.33-7.26 (m, 2H), 7.11 (d, J=8.1 Hz, 1H), 6.19 (dd, J=4.6, 1.1 Hz, 2H), 5.51 (dd, J=10.5, 2.8 Hz, 1H), 4.11 (dd, J=11.7, 2.7 Hz, 1H), 3.81-3.66 (m, 2H), 3.61 (d, J=11.9 Hz, 1H), 2.64 (td, J=11.4, 11.0, 3.0 Hz, 2H). UPLC-MS: $t_R$=2.09 min (Generic method); MS (ESI) m/z calcd for $C_{20}H_{19}N_2O_6S_2$ (M+H)$^+$: 447.1, found: 447.

3-[4-(2,3-Dihydro-1,4-benzodioxin-6-ylsulfonyl) morpholin-2-yl]benzothiophene-2-carboxamide: The title compound was prepared following GP1, from Int-1.6 (0.02 g, 0.07 mmol) and 1,3-benzodioxol-5-ylsulfonyl chloride (0.01 g, 0.06 mmol). The product was obtained, after purification by silica gel flash-column chromatography with DCM/EtOAc as the eluent, as a white solid (0.01 g, 44%). $^1$H NMR (400 MHz, DMSO-d$_6$) δ 8.13 (dt, J=8.2, 1.1 Hz, 1H), 8.04-7.97 (m, 2H), 7.77 (bs, 1H), 7.44 (ddd, J=8.2, 7.1, 1.2 Hz, 1H), 7.35 (ddd, J=8.2, 7.1, 1.2 Hz, 1H), 7.21 (dd, J=8.1, 1.2 Hz, 2H), 7.06 (dd, J=8.0, 0.8 Hz, 1H), 5.50 (dd, J=10.6, 2.8 Hz, 1H), 4.42-4.20 (m, 4H), 4.16-4.06 (m, 1H), 3.70 (td, J=11.7, 2.6 Hz, 2H), 3.60 (d, J=11.9 Hz, 1H), 2.67-2.55 (m, 2H). UPLC-MS: $t_R$=2.10 min (Generic method); MS (ESI) m/z calcd for $C_{21}H_{21}N_2O_6S_2$ (M+H)$^+$: 461.1, found: 461.

3-[4-[4-(4-Methoxyphenoxy)phenyl]sulfonylmorpholin-2-yl]benzothiophene-2-carboxamide: The title compound was prepared following GP1, from Int-1.6 (0.02 g, 0.07 mmol) and [4-(4-methoxyphenoxy)phenyl]sulfonyl chloride (0.02 g, 0.06 mmol). The product was obtained, after purification by silica gel flash-column chromatography with DCM/EtOAc as the eluent, as a white solid (0.02 g, 62%). $^1$H NMR (400 MHz, DMSO-d$_6$) δ 8.13 (d, J=8.2 Hz, 1H), 8.08-7.95 (m, 2H), 7.78 (bs, 1H), 7.76-7.68 (m, 2H), 7.45 (ddd, J=8.2, 7.0, 1.2 Hz, 1H), 7.37 (ddd, J=8.3, 7.1, 1.2 Hz, 1H), 7.14-7.06 (m, 3H), 7.06-7.00 (m, 3H), 5.51 (dd, J=10.5, 2.8 Hz, 1H), 4.11 (d, J=9.5 Hz, 1H), 3.78 (s, 3H), 3.76-3.65 (m, 2H), 3.61 (d, J=11.8 Hz, 1H), 2.68-2.54 (m, 2H). UPLC-MS: $t_R$=2.48 min (Generic method); MS (ESI) m/z calcd for $C_{26}H_{25}N_2O_6S_2$ (M+H)$^+$: 525.1, found: 525.

3-[4-(3-Fluorophenyl) sulfonylmorpholin-2-yl] benzothiophene-2-carboxamide: The title compound was prepared following GP1, from Int-1.6 (0.02 g, 0.07 mmol) and (3-fluorophenyl) sulfonyl chloride (0.01 g, 0.06 mmol). The product was obtained, after purification by silica gel flash-column chromatography with DCM/EtOAc as the eluent, as a white solid (0.01 g, 30%). $^1$H NMR (400 MHz, DMSO-d$_6$) δ 8.13 (dd, J=8.2, 1.0 Hz, 1H), 8.03-7.97 (m, 2H), 7.77 (bs, 1H), 7.73-7.66 (m, 1H), 7.67-7.58 (m, 3H), 7.43 (ddd, J=8.2, 7.1, 1.2 Hz, 1H), 7.34 (ddd, J=8.2, 7.1, 1.2 Hz, 1H), 5.51 (dd, J=10.5, 2.8 Hz, 1H), 4.11 (d, 1H), 3.79 (d, J=11.4, 2.3 Hz, 1H), 3.75-3.62 (m, 2H), 2.76-2.59 (m, 2H). UPLC-MS: $t_R$=2.17 min (Generic method); MS (ESI) m/z calcd for $C_{19}H_{18}FN_2O_4S_2$ (M+H)$^+$: 421. 1, found: 421.

3-[4-(3,4-Difluorophenyl) sulfonylmorpholin-2-yl] benzothiophene-2-carboxamide: The title compound was prepared following GP1, from Int-1.6 (0.02 g, 0.07 mmol) and (3,4-difluorophenyl) sulfonyl chloride (0.01 g, 0.06 mmol). The product was obtained, after purification by silica gel flash-column chromatography with DCM/EtOAc as the eluent, as a white solid (0.01 g, 31%). $^1$H NMR (400 MHz, DMSO-d$_6$) δ 8.16 (d, J=8.2 Hz, 1H), 8.06-7.97 (m, 2H), 7.93 (ddd, J=8.5, 6.8, 1.6 Hz, 1H), 7.77 (bs, 1H), 7.74-7.61 (m, 2H), 7.44 (ddd, J=8.2, 7.1, 1.2 Hz, 1H), 7.35 (ddd, J=8.2, 7.1, 1.2 Hz, 1H), 5.51 (dd, J=10.5, 2.8 Hz, 1H), 4.10 (dd, J=10.5, 2.8 Hz, 1H), 3.78 (dd, J=10.5, 2.8 Hz, 1H), 3.75-3.59 (m, 2H), 2.80-2.68 (m, 2H). UPLC-MS: $t_R$=2.24 min (Generic method); MS (ESI) m/z calcd for $C_{19}H_{17}F_2N_2O_4S_2$ (M+H)$^+$: 439.1, found: 439.

3-[4-(4-Fluorophenyl) sulfonylmorpholin-2-yl] benzothiophene-2-carboxamide: The title compound was prepared following GP1, from Int-1.6 (0.02 g, 0.07 mmol) and (4-fluorophenyl) sulfonyl chloride (0.01 g, 0.06 mmol). The product was obtained, after purification by silica gel flash-column chromatography with DCM/EtOAc as the eluent, as a white solid (0.02 g, 59%). $^1$H NMR (400 MHz, DMSO-d$_6$) δ 8.13 (d, J=8.3 Hz, 1H), 8.05-7.98 (m, 2H), 7.90-7.84 (m, 2H), 7.81 (bs, 1H), 7.57-7.41 (m, 3H), 7.35 (ddd, J=8.2, 7.0, 1.2 Hz, 1H), 5.51 (dd, J=10.5, 2.8 Hz, 1H), 4.11 (dd, J=11.7, 2.8 Hz, 1H), 3.82-3.59 (m, 3H), 2.64 (dd, J=12.3, 9.6 Hz, 2H). UPLC-MS: $t_R$=2.18 min (Generic method); MS (ESI) m/z calcd for $C_{19}H_{18}FN_2O_4S_2$ (M+H)$^+$: 421.1, found: 421.

3-[4-(4-Methoxy-3-methyl-phenyl) sulfonylmorpholin-2-yl]benzothiophene-2-carboxamide: The title compound was prepared following GP1, from Int-1.6 (0.03 g, 0.10 mmol) and (4-methoxy-3-methylphenyl) sulfonyl chloride (0.02 g, 0.09 mmol). The product was obtained, after purification by silica gel flash-column chromatography with DCM/EtOAc as the eluent, as a white solid (0.01 g, 34%). $^1$H NMR (400 MHz, DMSO-d$_6$) δ 8.10 (dt, J=8.2, 1.1 Hz, 1H), 8.05-7.95 (m, 2H), 7.76 (bs, 1H), 7.61-7.50 (m, 2H), 7.43 (ddd, J=8.2, 7.1, 1.3 Hz, 1H), 7.33 (ddd, J=8.3, 7.1, 1.2 Hz, 1H), 7.12 (d, J=8.6 Hz, 1H), 5.49 (dd, J=10.5, 2.8 Hz, 1H), 4.08 (d, J=11.9 Hz, 1H), 3.87 (s, 3H), 3.79-3.63 (m, 2H), 3.59 (d, J=11.8 Hz, 1H), 2.57 (td, J=11.4, 4.2 Hz, 2H), 2.19 (s, 3H). UPLC-MS: $t_R$=2.28 min (Generic method); MS (ESI) m/z calcd for $C_{21}H_{23}N_2O_5S_2$ (M+H)$^+$: 447.1, found: 447.

3-[4-[4-(4-Pyridyloxy)phenyl]sulfonylmorpholin-2-yl] benzothiophene-2-carboxamide: The title compound was prepared following GP1, from Int-1.6 (0.03 g, 0.10 mmol) and [3-(4-pyridyloxy)phenyl]sulfonyl chloride (0.03 g, 0.09 mmol). The product was obtained, after purification by silica gel flash-column chromatography with DCM/EtOAc as the eluent, as a white solid (0.02 g, 54%). $^1$H NMR (400 MHz, DMSO-d$_6$) δ 8.54 (dt, J=8.2, 1.1 Hz, 2H), 8.13 (d, J=8.2 Hz, 1H), 8.05-7.96 (m, 2H), 7.84 (dt, J=8.2, 1.1 Hz, 2H), 7.76 (bs, 1H), 7.44 (ddd, J=8.2, 7.0, 1.2 Hz, 1H), 7.41-7.30 (m, 3H), 7.07 (dt, J=8.2, 1.1 Hz, 2H), 5.50 (dd, J=10.5, 2.8 Hz, 1H), 4.18-4.04 (m, 1H), 3.81-3.59 (m, 3H), 2.76-2.57 (m, 2H). UPLC-MS: $t_R$=2.05 min (Generic method); MS (ESI) m/z calcd for $C_{24}H_{22}N_3O_5S_2$ (M+H)$^+$: 496.1, found: 496.

3-[4-(3-Fluoro-4-methyl-phenyl) sulfonylmorpholin-2-yl]benzothiophene-2-carboxamide: The title compound was prepared following GP1, from Int-1.6 (0.04 g, 0.10 mmol) and (3-fluoro-4-methyl-phenyl) sulfonyl chloride (0.03 g, 0.09 mmol). The product was obtained, after purification by silica gel flash-column chromatography with DCM/EtOAc as the eluent, as a white solid (0.03 g, 70%). $^1$H NMR (400 MHz, DMSO-d$_6$) δ 8.13 (d, J=8.1 Hz, 1H), 8.02-7.96 (m, 2H), 7.76 (bs, 1H), 7.59-7.49 (m, 3H), 7.43 (ddd, J=8.2, 7.1, 1.2 Hz, 1H), 7.34 (ddd, J=8.2, 7.0, 1.1 Hz, 1H), 5.50 (dd, J=10.5, 2.8 Hz, 1H), 4.09 (dd, J=11.3, 3.0 Hz, 1H), 3.81-3.59 (m, 3H), 2.74-2.57 (m, 2H), 2.32 (s, 3H). UPLC-MS: $t_R$=2.28 min (Generic method); MS (ESI) m/z calcd for $C_{20}H_{20}FN_2O_4S_2$ (M+H)$^+$: 435.1, found: 435. Yield: 70%.

3-[4-(5-Fluoro-2-methyl-phenyl) sulfonylmorpholin-2-yl]benzothiophene-2-carboxamide: The title compound was prepared following GP1, from Int-1.6 (0.04 g, 0.10 mmol) and (2-methyl-5-fluoro-phenyl) sulfonyl chloride (0.02 g, 0.09 mmol). The product was obtained, after purification by silica gel flash-column chromatography with DCM/EtOAc as the eluent, as a white solid (0.02 g, 45%). $^1$H NMR (400 MHz, DMSO-d$_6$) § 8.24 (dd, J=8.0, 1.1 Hz, 1H), 8.00 (dd, J=7.9, 1.0 Hz, 1H), 7.99 (bs, 1H), 7.75 (bs, 1H), 7.61 (dd, J=8.8, 2.7 Hz, 1H), 7.56-7.35 (m, 4H), 5.45 (dd, J=10.6, 2.8 Hz, 1H), 4.10 (dd, J=11.4, 2.9 Hz, 1H), 3.77-3.52 (m, 3H), 3.14-2.94 (m, 2H), 2.56 (s, 3H). UPLC-MS: $t_R$=2.26 min (Generic method); MS (ESI) m/z calcd for $C_2H_{20}FN_2O_4S_2$ (M+H)$^+$: 435.1, found: 435. Yield: 45%.

3-[4-(2,4,6-Trimethylphenyl) sulfonylmorpholin-2-yl] benzothiophene-2-carboxamide: The title compound was prepared following GP1, from Int-1.6 (0.03 g, 0.07 mmol) and (2,4,6-trimethylphenyl) sulfonyl chloride (0.01 g, 0.06 mmol). The product was obtained, after purification by silica gel flash-column chromatography with DCM/EtOAc as the eluent, as a white solid (0.01 g, 42%). $^1$H NMR (400 MHz, DMSO-d$_6$) δ 8.28 (d, J=1.5 Hz, 1H), 8.01 (d, J=1.5 Hz, 1H), 7.97 (bs, 1H), 7.73 (bs, 1H), 7.51-7.36 (m, 2H), 7.09 (s, 2H), 5.42 (dd, J=10.6, 2.8 Hz, 1H), 4.08 (dd, J=11.6, 2.7 Hz, 1H), 3.65-3.50 (m, 2H), 3.31-3.25 (m, 1H), 3.18-3.05 (m, 2H), 2.57 (s, 6H), 2.28 (s, 3H). UPLC-MS: $t_R$=2.53 min (Generic method); MS (ESI) m/z calcd for $C_{22}H_{25}N_2O_4S_2$ (M+H)$^+$: 445.1, found: 445.

3-[4-(p-Tolylsulfonyl) morpholin-2-yl]benzothiophene-2-carboxamide: The title compound was prepared following GP1, from Int-1.6 (0.03 g, 0.07 mmol) and (4-methylphenyl) sulfonyl chloride (0.01 g, 0.06 mmol). The product was obtained, after purification by silica gel flash-column chromatography with DCM/EtOAc as the eluent, as a white solid (0.01 g, 50%). $^1$H NMR (400 MHz, DMSO-d$_6$) δ 8.08 (dt, J=8.4, 1.1 Hz, 1H), 8.04-7.96 (m, 2H), 7.76 (bs, 1H), 7.62 (d, J=8.4 Hz, 2H), 7.47-7.37 (m, 3H), 7.32 (ddd, J=8.3, 7.1, 1.2 Hz, 1H), 5.49 (dd, J=10.5, 2.8 Hz, 1H), 4.08 (dd, J=11.6, 2.9 Hz, 1H), 3.80-3.53 (m, 3H), 2.65-2.51 (m, 2H), 2.39 (s, 3H). UPLC-MS: $t_R$=2.30 min (Generic method); MS (ESI) m/z calcd for $C_{20}H_{21}N_2O_4S_2$ (M+H)$^+$: 417.1, found: 417.

3-[4-[(2-Methyl-1,3-benzoxazol-6-yl) sulfonyl]morpholin-2-yl]benzothiophene-2-carboxamide: The title compound was prepared following GP1, from Int-1.6 (0.03 g, 0.07 mmol) and (2-methyl-1,3-benzoxazol-6-yl) sulfonyl chloride (0.01 g, 0.06 mmol). The product was obtained, after purification by silica gel flash-column chromatography with DCM/EtOAc as the eluent, as a white solid (0.01 g, 40%). 1H NMR (400 MHz, DMSO-d$_6$) δ 8.13 (dd, J=1.7, 0.5 Hz, 1H), 8.07 (dt, J=8.3, 1.0 Hz, 1H), 8.03-7.94 (m, 2H), 7.86 (d, J=8.4 Hz, 1H), 7.82-7.66 (m, 2H), 7.40 (ddd, J=8.2, 7.1, 1.2 Hz, 1H), 7.28 (ddd, J=8.2, 7.1, 1.2 Hz, 1H), 5.50 (dd, J=10.5, 2.8 Hz, 1H), 4.08 (dd, J=11.3 Hz, 1H), 3.79 (d, J=11.2 Hz, 1H), 3.68 (t, J=12.0 Hz, 2H), 2.66 (s, 3H), 2.64-2.56 (m, 2H). UPLC-MS: $t_R$=2.05 min (Generic method); MS (ESI) m/z calcd for $C_{21}H_{20}N_3O_5S_2$ (M+H)$^+$: 458.1, found: 458.

3-[4-[3-(Trifluoromethyl)phenyl]sulfonylmorpholin-2-yl]benzothiophene-2-carboxamide: The title compound was prepared following GP1, from Int-1.6 (0.03 g, 0.07 mmol) and [3-(trifluoromethyl)phenyl]sulfonyl chloride (0.01 g, 0.06 mmol). The product was obtained, after purification by silica gel flash-column chromatography with DCM/EtOAc as the eluent, as a white solid (0.01 g, 50%). $^1$H NMR (400 MHz, DMSO-d$_6$) δ 8.16-8.06 (m, 3H), 8.05-7.94 (m, 3H), 7.88 (t, J=8.2 Hz, 1H), 7.75 (bs, 1H), 7.42 (ddd, J=8.2, 7.1, 1.2 Hz, 1H), 7.31 (ddd, J=8.2, 7.0, 1.2 Hz, 1H), 5.49 (dd, J=10.5, 2.8 Hz, 1H), 4.09 (dd, J=11.1, 3.0 Hz, 1H), 3.82 (dd, J=11.1, 3.1 Hz, 1H), 3.68 (t, J=10.4 Hz, 2H), 2.79-2.63 (m, 2H). UPLC-MS: $t_R$=2.40 min (Generic method); MS (ESI) m/z calcd for $C_{20}H_{18}F_3N_2O_4S_2$ (M+H)$^+$: 471.1, found: 471.

3-[4-(4-tert-Butylphenyl) sulfonylmorpholin-2-yl] benzothiophene-2-carboxamide: The title compound was prepared following GP1, from Int-1.6 (0.03 g, 0.07 mmol) and (4-tert-butylphenyl) sulfonyl chloride (0.01 g, 0.06 mmol). The product was obtained, after purification by silica gel flash-column chromatography with DCM/EtOAc as the eluent, as a white solid (0.01 g, 47%). $^1$H NMR (400 MHz, DMSO-d$_6$) δ 8.06 (dt, J=8.2, 1.0 Hz, 1H), 8.02-7.96 (m, 2H), 7.73 (bs, 1H), 7.69-7.59 (m, 4H), 7.41 (ddd, J=8.2, 7.1, 1.2 Hz, 1H), 7.29 (ddd, J=8.2, 7.1, 1.1 Hz, 1H), 5.49 (dd, J=10.5, 2.8 Hz, 1H), 4.09 (dd, J=10.5, 2.8 Hz, 1H), 3.80-3.54 (m, 3H), 2.71-2.54 (m, 2H), 1.29 (s, 9H). UPLC-MS: $t_R$=2.65 min (Generic method); MS (ESI) m/z calcd for $C_{23}H_{27}N_2O_4S_2$ (M+H)$^+$: 459.1, found: 459.

3-[4-(4-Cyanophenyl) sulfonylmorpholin-2-yl] benzothiophene-2-carboxamide: The title compound was prepared following GP1, from Int-1.6 (0.03 g, 0.07 mmol) and (4-cyanophenyl) sulfonyl chloride (0.01 g, 0.06 mmol). The product was obtained, after purification by silica gel flash-column chromatography with DCM/EtOAc as the eluent, as a white solid (0.01 g, 34%). $^1$H NMR (400 MHz, DMSO-$d_6$) δ 8.12 (dt, J=8.2, 1.0 Hz, 1H), 8.09 (d, J=8.3 Hz, 2H), 8.01-7.96 (m, 2H), 7.94 (d, J=8.3 Hz, 2H), 7.75 (bs, 1H), 7.42 (ddd, J=8.2, 7.0, 1.2 Hz, 1H), 7.33 (ddd, J=8.3, 7.1, 1.2 Hz, 1H), 5.46 (dd, J=10.5, 2.8 Hz, 1H), 4.08 (dd, J=11.2, 3.0 Hz, 1H), 3.79 (d, J=11.3 Hz, 1H), 3.67 (t, J=10.3 Hz, 2H), 2.72 (td, J=11.7, 11.2, 3.4 Hz, 2H). UPLC-MS: $t_R$=2.14 min (Generic method); MS (ESI) m/z calcd for $C_{20}H_{18}N_3O_4S_2$ (M+H)$^+$: 428.1, found: 428.

3-[4-[4-Fluoro-3-(trifluoromethyl)phenyl] sulfonylmorpholin-2-yl]benzothiophene-2-carboxamide: The title compound was prepared following GP1, from Int-1.6 (0.03 g, 0.07 mmol) and [4-fluoro-3-(trifluoromethyl)phenyl]sulfonyl chloride (0.02 g, 0.06 mmol). The product was obtained, after purification by silica gel flash-column chromatography with DCM/EtOAc as the eluent, as a white solid (0.01 g, 47%). $^1$H NMR (400 MHz, DMSO-$d_6$) δ 8.22-8.13 (m, 2H), 8.04 (dd, J=6.7, 2.3 Hz, 1H), 8.01-7.95 (m, 2H), 7.82-7.66 (m, 3H), 7.42 (ddd, J=8.2, 7.1, 1.2 Hz, 1H), 7.33 (ddd, J=8.2, 7.1, 1.2 Hz, 1H), 5.48 (dd, J=10.5, 2.8 Hz, 1H), 4.15-4.02 (m, 1H), 3.85-3.74 (m, 1H), 3.74-3.62 (m, 2H), 2.78 (td, J=11.8, 11.2, 3.4 Hz, 2H). UPLC-MS: $t_R$=2.46 min (Generic method); MS (ESI) m/z calcd for $C_{20}H_{17}F_4N_2O_4S_2$ (M+H)$^+$: 489.1, found: 489.

3-[4-[4-(Trifluoromethoxy)phenyl]sulfonylmorpholin-2-yl] benzothiophene-2-carboxamide: The title compound was prepared following GP1, from Int-1.6 (0.03 g, 0.07 mmol) and [4-(trifluoromethoxy)phenyl]sulfonyl chloride (0.02 g, 0.06 mmol). The product was obtained, after purification by silica gel flash-column chromatography with DCM/EtOAc as the eluent, as a white solid (0.01 g, 46%). $^1$H NMR (400 MHz, DMSO-$d_6$) δ 8.10 (dt, J=8.4, 1.0 Hz, 1H), 8.02-7.98 (m, 2H), 7.90 (dt, J=8.4, 1.0 Hz, 2H), 7.78 (bs, 1H), 7.60 (dt, J=8.9, 1.0 Hz, 2H), 7.42 (ddd, J=8.2, 7.0, 1.2 Hz, 1H), 7.31 (ddd, J=8.2, 7.1, 1.2 Hz, 1H), 5.49 (dd, J=10.5, 2.8 Hz, 1H), 4.09 (dd, J=11.3, 2.9 Hz, 1H), 3.77 (d, J=11.3 Hz, 1H), 3.73-3.58 (m, 2H), 2.73-2.60 (m, 2H). UPLC-MS: $t_R$=2.48 min (Generic method); MS (ESI) m/z calcd for $C_{20}H_{18}F_3N_2O_4S_2$ (M+H)$^+$: 487.1, found: 487.

3-[4-(4-Chlorophenyl) sulfonylmorpholin-2-yl] benzothiophene-2-carboxamide: The title compound was prepared following GP1, from Int-1.6 (0.03 g, 0.07 mmol) and (4-chorophenyl) sulfonyl chloride (0.01 g, 0.06 mmol). The product was obtained, after purification by silica gel flash-column chromatography with DCM/EtOAc as the eluent, as a white solid (0.01 g, 46%).$^1$H NMR (400 MHz, DMSO-$d_6$) δ 8.10 (dt, J=8.2, 1.0 Hz, 1H), 8.03-7.95 (m, 2H), 7.80-7.73 (m, 3H), 7.71-7.64 (m, 2H), 7.41 (ddd, J=8.2, 7.1, 1.2 Hz, 1H), 7.32 (ddd, J=8.2, 7.1, 1.2 Hz, 1H), 5.47 (dd, J=10.5, 2.8 Hz, 1H), 4.07 (dd, J=11.7, 2.9 Hz, 1H), 3.78-3.57 (m, 3H), 2.70-2.57 (m, 2H). UPLC-MS: $t_R$=2.37 min (Generic method); MS (ESI) m/z calcd for $C_{19}H_{18}ClN_2O_4S_2$ (M+H)$^+$: 437.0, found: 437.

3-[4-[3-Fluoro-4-(trifluoromethyl)phenyl] sulfonylmorpholin-2-yl]benzothiophene-2-carboxamide: The title compound was prepared following GP1, from Int-1.6 (0.03 g, 0.07 mmol) and [3-fluoro-4-(trifluoromethyl)phenyl]sulfonyl (0.02 g, 0.06 mmol). The product was obtained, after purification by silica gel flash-column chromatography with DCM/EtOAc as the eluent, as a white solid (0.01 g, 27%). $^1$H NMR (400 MHz, DMSO-$d_6$) δ 8.19 (d, J=8.2 Hz, 1H), 8.09-7.95 (m, 4H), 7.81 (d, J=8.3 Hz, 1H), 7.76 (bs, 1H), 7.44 (ddd, J=8.2, 7.0, 1.2 Hz, 1H), 7.34 (ddd, J=8.2, 7.1, 1.2 Hz, 1H), 5.50 (dd, J=10.6, 2.8 Hz, 1H), 4.10 (dd, J=11.4, 3.0 Hz, 1H), 3.84 (d, J=11.3 Hz, 1H), 3.77-3.61 (m, 2H), 2.95-2.77 (m, 2H). UPLC-MS: $t_R$=2.50 min (Generic method); MS (ESI) m/z calcd for $C_{20}H_{17}F_4N_2O_4S_2$ (M+H)$^+$: 489.1, found: 489.

3-[4-[3-Methyl-4-(trifluoromethyl)phenyl] sulfonylmorpholin-2-yl]benzothiophene-2-carboxamide: The title compound was prepared following GP1, from Int-1.6 (0.01 g, 0.05 mmol) and [3-methyl-4-(trifluoromethyl)phenyl]sulfonyl (0.02 g, 0.06 mmol). The product was obtained, after purification by silica gel flash-column chromatography with DCM/EtOAc as the eluent, as a white solid (0.01 g, 44%). $^1$H NMR (400 MHz, DMSO-$d_6$) δ 8.15 (dt, J=8.3, 1.0 Hz, 1H), 8.08-7.93 (m, 2H), 7.89 (td, J=8.3, 1.0 Hz, 2H), 7.86-7.67 (m, 2H), 7.42 (ddd, J=8.1, 7.1, 1.3 Hz, 1H), 7.33 (ddd, J=8.3, 7.1, 1.2 Hz, 1H), 5.48 (dd, J=10.5, 2.8 Hz, 1H), 4.09 (dd, J=10.5, 2.8 Hz, 1H), 3.82 (dd, J=11.4, 2.3 Hz, 1H), 3.75-3.60 (m, 2H), 2.83-2.63 (m, 2H), 2.52 (s, 3H). UPLC-MS: $t_R$=2.48 min (Generic method); MS (ESI) m/z calcd for $C_{21}H_{20}F_3N_2O_4S_2$ (M+H)$^+$: 485.1, found: 485.

3-[4-[3-Methoxy-4-(trifluoromethyl)phenyl]sulfonylmorpholin-2-yl]benzothiophene-2-carboxamide: The title compound was prepared following GP1, from Int-1.6 (0.01 g, 0.05 mmol) and [3-methoxy-4-(trifluoromethyl)phenyl] sulfonyl (0.02 g, 0.06 mmol). The product was obtained, after purification by silica gel flash-column chromatography with DCM/EtOAc as the eluent, as a white solid (0.01 g, 32%). $^1$H NMR (400 MHz, DMSO-$d_6$) δ 8.14 (d, J=8.1, 1.0 Hz, 1H), 8.04-7.93 (m, 2H), 7.84 (d, J=8.6 Hz, 1H), 7.73 (bs, 1H), 7.45 (d, J=6.5 Hz, 2H), 7.40 (ddd, J=8.2, 7.1, 1.2 Hz, 1H), 7.31 (ddd, J=8.2, 7.1, 1.2 Hz, 1H), 5.47 (dd, J=10.5, 2.8 Hz, 1H), 4.07 (dd, J=11.3, 2.9 Hz, 1H), 3.95 (s, 3H), 3.82 (dd, J=11.3, 2.9 Hz, 1H), 3.73-3.60 (m, 2H), 2.90-2.72 (m, 2H). UPLC-MS: $t_R$=2.42 min (Generic method); MS (ESI) m/z calcd for $C_{21}H_{20}F_3N_2O_5S_2$ (M+H)$^+$: 501.1, found: 501.

3-[4-[4-Methoxy-3-(trifluoromethyl)phenyl] sulfonylmorpholin-2-yl]benzothiophene-2-carboxamide: The title compound was prepared following GP1, from Int-1.6 (0.01 g, 0.05 mmol) and [4-methoxy-3-(trifluoromethyl)phenyl]sulfonyl chloride (0.02 g, 0.06 mmol). The product was obtained, after purification by silica gel flash-column chromatography with DCM/EtOAc as the eluent, as a white solid (0.01 g, 24%). $^1$H NMR (400 MHz, DMSO-$d_6$) δ 8.12 (dt, J=8.1, 0.9 Hz, 1H), 8.02 (dd, J=8.9, 2.4 Hz, 1H), 8.00-7.94 (m, 2H), 7.83 (d, J=2.4 Hz, 1H), 7.73 (bs, 1H), 7.50-7.36 (m, 2H), 7.31 (ddd, J=8.2, 7.1, 1.2 Hz, 1H), 5.47 (dd, J=10.5, 2.8 Hz, 1H), 4.08 (dd, J=11.3, 2.9 Hz, 1H), 3.97 (s, 3H), 3.77 (dd, J=11.1, 2.4 Hz, 1H), 3.74-3.56 (m, 2H), 2.65 (td, J=11.2, 3.7 Hz, 2H). UPLC-MS: $t_R$=2.33 min (Generic method); MS (ESI) m/z calcd for $C_{21}H_{20}F_3N_2O_5S_2$ (M+H)$^+$: 501.1, found: 501.

3-[4-(4-Methoxy-3-nitro-phenyl) sulfonylmorpholin-2-yl]benzothiophene-2-carboxamide: The title compound was prepared following GP1, from Int-1.6 (0.02 g, 0.06 mmol) and (4-methoxy-3-nitro-phenyl]sulfonyl chloride (0.01 g, 0.06 mmol). The product was obtained, after purification by silica gel flash-column chromatography with DCM/EtOAc as the eluent, as a white solid (0.01 g, 31%). $^1$H NMR (400 MHz, DMSO-$d_6$) δ 8.22 (d, J=2.4 Hz, 1H), 8.13 (d, J=8.2, 1.1 Hz, 1H), 8.08-7.91 (m, 3H), 7.72 (bs, 1H), 7.52 (d, J=9.0 Hz, 1H), 7.41 (ddd, J=8.1, 7.0, 1.2 Hz, 1H), 7.32 (ddd, J=8.2, 7.1, 1.2 Hz, 1H), 5.47 (dd, J=10.5, 2.8 Hz, 1H), 4.08 (dd, J=11.5, 2.9 Hz, 1H), 3.99 (s, 3H), 3.80-3.57 (m, 3H), 2.78-2.60 (m, 2H). UPLC-MS: $t_R$=2.12 min (Generic method); MS (ESI) m/z calcd for $C_{20}H_{20}N_3O_7S_2$ (M+H)$^+$: 478.1, found: 478.

3-[4-(3-Methoxyphenyl) sulfonylmorpholin-2-yl] benzothiophene-2-carboxamide: The title compound was prepared following GP1, from Int-1.6 (0.02 g, 0.04 mmol) and (3-methoxyphenyl) sulfonyl chloride (0.01 g, 0.04 mmol). The product was obtained, after purification by silica gel flash-column chromatography with DCM/EtOAc as the eluent, as a white solid (0.01 g, 31%). $^1$H NMR (400 MHz, DMSO-d$_6$) δ 8.10 (dt, J=8.3, 1.0 Hz, 1H), 8.03-7.96 (m, 2H), 7.78 (bs, 1H), 7.54 (t, J=8.0 Hz, 1H), 7.43 (ddd, J=8.1, 7.0, 1.2 Hz, 1H), 7.38-7.25 (m, 3H), 7.21 (dd, J=2.6, 1.6 Hz, 1H), 5.50 (dd, J=10.5, 2.8 Hz, 1H), 4.09 (dd, J=11.1, 3.0 Hz, 1H), 3.79-3.60 (m, 3H), 2.72-2.58 (m, 2H). UPLC-MS: t$_R$=2.14 min (Generic method); MS (ESI) m/z calcd for C$_{20}$H$_{21}$N$_2$O$_5$S$_2$ (M+H)$^+$: 433.1, found: 433.

3-[4-[3-(Trifluoromethoxy)phenyl]sulfonylmorpholin-2-yl]benzothiophene-2-carboxamide: The title compound was prepared following GP1, from Int-1.6 (0.02 g, 0.04 mmol) and [3-(trifluoromethoxy)phenyl]sulfonyl chloride (0.01 g, 0.04 mmol). The product was obtained, after purification by silica gel flash-column chromatography with DCM/EtOAc as the eluent, as a white solid (0.01 g, 32%). $^1$H NMR (400 MHz, DMSO-d$_6$) δ 8.10 (dt, J=8.3, 1.0 Hz, 1H), 8.07-7.94 (m, 2H), 7.83 (ddd, J=5.9, 4.6, 3.3 Hz, 1H), 7.80-7.75 (m, 3H), 7.74 (dt, J=2.3, 1.0 Hz, 1H), 7.43 (ddd, J=8.2, 7.1, 1.2 Hz, 1H), 7.32 (ddd, J=8.2, 7.1, 1.1 Hz, 1H), 5.51 (dd, J=10.5, 2.8 Hz, 1H), 4.10 (dd, J=11.1, 2.9 Hz, 1H), 3.80 (dt, J=11.4, 2.3 Hz, 1H), 3.69 (ddd, J=14.2, 11.1, 3.7 Hz, 2H), 2.74-2.58 (m, 2H). UPLC-MS: t$_R$=2.38 min (Generic method); MS (ESI) m/z calcd for C$_{20}$H$_{18}$F$_3$N$_2$O$_5$S$_2$ (M+H)$^+$: 487.1, found: 487.

3-[4-(2-Methoxyphenyl) sulfonylmorpholin-2-yl] benzothiophene-2-carboxamide: The title compound was prepared following GP1, from Int-1.6 (0.02 g, 0.04 mmol) and (2-methoxyphenyl) sulfonyl chloride (0.01 g, 0.04 mmol). The product was obtained, after purification by silica gel flash-column chromatography with DCM/EtOAc as the eluent, as a white solid (0.005 g, 23%). $^1$H NMR (400 MHz, DMSO-d$_6$) δ 8.19 (dt, J=7.9, 1.1 Hz, 1H), 8.03-7.97 (m, 2H), 7.78 (bs, 1H), 7.74 (dd, J=7.8, 1.7 Hz, 1H), 7.64 (ddd, J=8.3, 7.3, 1.7 Hz, 1H), 7.44 (ddd, J=8.1, 7.1, 1.3 Hz, 1H), 7.38 (ddd, J=8.2, 7.0, 1.3 Hz, 1H), 7.27 (dd, J=8.4, 1.0 Hz, 1H), 7.08 (td, J=7.6, 1.0 Hz, 1H), 5.43 (dd, J=10.7, 2.9 Hz, 1H), 4.09 (dd, J=11.4, 2.8 Hz, 1H), 3.72-3.56 (m, 2H), 3.08-2.88 (m, 3H). UPLC-MS: t$_R$=2.04 min (Generic method); MS (ESI) m/z calcd for C$_{20}$H$_{21}$N$_2$O$_5$S$_2$ (M+H)$^+$: 433.1, found: 433.

3-[4-(4-Phenylphenyl) sulfonylmorpholin-2-yl] benzothiophene-2-carboxamide: The title compound was prepared following GP1, from Int-1.6 (0.02 g, 0.04 mmol) and (4-phenylphenyl) sulfonyl chloride (0.01 g, 0.04 mmol). The product was obtained, after purification by silica gel flash-column chromatography with DCM/EtOAc as the eluent, as a white solid (0.005 g, 28%). $^1$H NMR (400 MHz, DMSO-d$_6$) δ 8.11 (dt, J=8.3, 1.0 Hz, 1H), 8.03 (bs, 1H), 8.00-7.96 (m, 1H), 7.92 (d, J=8.5 Hz, 2H), 7.82 (d, J=8.5 Hz, 2H), 7.75 (bs, 1H), 7.77-7.70 (m, 2H), 7.55-7.47 (m, 2H), 7.47-7.37 (m, 2H), 7.30 (ddd, J=8.2, 7.0, 1.1 Hz, 1H), 5.51 (dd, J=10.5, 2.8 Hz, 1H), 4.11 (dd, J=10.5, 2.8 Hz, 1H), 3.80 (d, J=10.9 Hz, 1H), 3.77-3.60 (m, 2H), 2.76-2.56 (m, 2H). UPLC-MS: t$_R$=2.50 min (Generic method); MS (ESI) m/z calcd for C$_{25}$H$_{23}$N$_2$O$_4$S$_2$ (M+H)$^+$: 479.1, found: 479.

3-[4-(2-Naphthylsulfonyl)morpholin-2-yl]benzothiophene-2-carboxamide: The title compound was prepared following GP1, from Int-1.6 (0.02 g, 0.04 mmol) and 2-napthylsulfonyl chloride (0.01 g, 0.04 mmol). The product was obtained, after purification by silica gel flash-column chromatography with DCM/EtOAc as the eluent, as a white solid (0.005 g, 27%). $^1$H NMR (400 MHz, DMSO-d$_6$) δ 8.47 (d, J=1.8 Hz, 1H), 8.19 (d, J=1.8 Hz, 1H), 8.14 (d, J=8.8 Hz, 1H), 8.10-7.99 (m, 4H), 7.97 (dt, J=8.2, 0.9 Hz, 1H), 7.81-7.64 (m, 3H), 7.38 (ddd, J=8.2, 7.1, 1.2 Hz, 1H), 7.24 (ddd, J=8.3, 7.1, 1.2 Hz, 1H), 5.52 (dd, J=10.5, 2.8 Hz, 1H), 4.09 (dd, v1H), 3.85 (d, J=11.3 Hz, 1H), 3.76-3.62 (m, 2H), 2.74-2.59 (m, 2H). UPLC-MS: t$_R$=2.35 min (Generic method); MS (ESI) m/z calcd for C$_{23}$H$_{21}$N$_2$O$_4$S$_2$(M+H)$^+$: 453.1, found: 453.

3-[4-(3-Fluoro-4-methoxy-phenyl)sulfonylmorpholin-2-yl]benzothiophene-2-carboxamide: The title compound was prepared following GP1, from Int-1.6 (0.02 g, 0.04 mmol) and (3-fluoro-4-methoxy-phenyl)sulfonyl chloride(0.01 g, 0.04 mmol). The product was obtained, after purification by silica gel flash-column chromatography with DCM/EtOAc as the eluent, as a white solid (0.005 g, 28%). $^1$H NMR (400 MHz, DMSO-d$_6$) δ 8.13 (d, J=8.1 Hz, 1H), 8.05-7.94 (m, 2H), 7.78 (bs, 1H), 7.64 (dd, J=10.7, 2.2 Hz, 1H), 7.62-7.55 (m, 1H), 7.43 (ddd, J=8.2, 7.1, 1.2 Hz, 1H), 7.40-7.31 (m, 2H), 5.50 (dd, J=10.5, 2.8 Hz, 1H), 4.10 (dd, J=10.5, 2.8 Hz, 1H), 3.93 (s, 3H), 3.80-3.54 (m, 3H), 2.67-2.56 (m, 2H). UPLC-MS: t$_R$=2.16 min (Generic method); MS (ESI) m/z calcd for C$_{20}$H$_{20}$FN$_2$O$_5$S$_2$ (M+H)$^+$: 451.1, found: 451.

3-[4-(3,4-Dimethoxyphenyl)sulfonylmorpholin-2-yl]benzothiophene-2-carboxamide: The title compound was prepared following GP1, from Int-1.6 (0.02 g, 0.04 mmol) and (3,4-dimethoxyphenyl)sulfonyl chloride (0.01 g, 0.04 mmol). The product was obtained, after purification by silica gel flash-column chromatography with DCM/EtOAc as the eluent, as a white solid (0.005 g, 26%). 1H NMR (400 MHz, DMSO-d$_6$) δ 8.11 (dd, J=8.3, 1.1 Hz, 1H), 8.03-7.98 (m, 2H), 7.78 (bs, 1H), 7.43 (ddd, J=8.1, 7.0, 1.2 Hz, 1H), 7.34 (ddd, J=9.7, 8.4, 1.7 Hz, 2H), 7.18 (d, J=2.1 Hz, 1H), 7.14 (d, J=8.5 Hz, 1H), 5.50 (dd, J=10.5, 2.8 Hz, 1H), 4.09 (dd, J=10.5, 2.8 Hz, 1H), 3.84 (s, 3H), 3.80 (s, 3H), 3.77-3.59 (m, 3H), 2.66-2.58 (m, 2H). UPLC-MS: t$_R$=2.05 min (Generic method); MS (ESI) m/z calcd for C$_{21}$H$_{23}$N$_2$O$_6$S$_2$ (M+H)$^+$: 463.1, found: 463.

3-[4-[(4-Methyl-2,3-dihydro-1,4-benzoxazin-7-yl) sulfonyl]morpholin-2-yl]benzothiophene-2-carboxamide: The title compound was prepared following GP1, from Int-1.6 (0.02 g, 0.04 mmol) and (4-methyl-2,3-dihydro-1,4-benzoxazin-7-yl)sulfonyl chloride(0.01 g, 0.04 mmol). The product was obtained, after purification by silica gel flash-column chromatography with DCM/EtOAc as the eluent, as a white solid (0.007 g, 30%). $^1$H NMR (400 MHz, DMSO-d$_6$) δ 8.13 (dd, J=8.1, 1.1 Hz, 1H), 8.04-7.99 (m, 2H), 7.78 (bs, 1H), 7.45 (ddd, J=8.1, 7.0, 1.2 Hz, 1H), 7.36 (ddd, J=8.3, 7.1, 1.2 Hz, 1H), 6.94 (dd, J=8.3, 2.1 Hz, 1H), 6.89 (d, J=2.1 Hz, 1H), 6.84 (d, J=8.3 Hz, 1H), 5.50 (dd, J=10.5, 2.8 Hz, 1H), 4.31 (dd, J=10.5, 2.8 Hz, 2H), 4.10 (d, J=11.6, 2.8 Hz, 1H), 3.71 (d, J=11.5 Hz, 2H), 3.60 (d, J=11.8 Hz, 1H), 3.32-3.28 (m, 2H), 2.84 (s, 3H), 2.74-2.56 (m, 2H). UPLC-MS: t$_R$=2.14 min (Generic method); MS (ESI) m/z calcd for C$_{22}$H$_{24}$N$_3$O$_5$S$_2$(M+H)$^+$: 474.1, found: 474.

3-(4-Tetrahydropyran-4-ylsulfonylmorpholin-2-yl) benzothiophene-2-carboxamide: The title compound was prepared following GP1, from Int-1.6 (0.02 g, 0.05 mmol) and 4-tetrahydropyran-4-yl-sulfonylchloride(0.01 g, 0.05 mmol). The product was obtained, after purification by silica gel flash-column chromatography with DCM/EtOAc as the eluent, as a white solid (0.008 g, 41%). $^1$H NMR (400 MHz, DMSO-d$_6$) δ 8.37 (dd, J=8.1, 1.1 Hz, 1H), 8.06-8.00 (m, 2H), 7.76 (bs, 1H), 7.53-7.41 (m, 2H), 5.43 (dd, J=10.5, 2.9 Hz, 1H), 4.12 (dd, J=11.4, 2.8 Hz, 1H), 3.99-3.87 (m, 2H), 3.72-3.63 (m, 2H), 3.60 (d, J=12.5 Hz, 1H), 3.53 (tt,J=11.9, 3.7 Hz, 1H), 1.91 (d, J=12.9 Hz, 1H), 1.67 (dq,J=11.9, 3.7 Hz, 2H). UPLC-MS: t$_R$=1.79 min (Generic method); MS (ESI) m/z calcd for C$_{18}$H$_{23}$N$_2$O$_5$S$_2$ (M+H)$^+$: 411.1, found: 411.

3-[4-(2-Methoxyethylsulfonyl)morpholin-2-yl]benzothiophene-2-carboxamide: The title compound was prepared following GP1, from Int-1.6 (0.02 g, 0.06 mmol) and 2-methoxyethylsulfonyl chloride(0.01 g, 0.05 mmol). The product was obtained, after purification by silica gel flash-column chromatography with DCM/EtOAc as the eluent, as a white solid (0.007 g, 37%). $^1$H NMR (400 MHz, DMSO-$d_6$) δ 8.34 (dd, J=8.1, 1.1 Hz, 1H), 8.08-7.99 (m, 2H), 7.80 (bs, 1H), 7.53-7.40 (m, 2H), 5.46 (dd, J=10.6, 2.9 Hz, 1H), 4.14 (dd, J=11.6, 2.8 Hz, 1H), 3.74-3.68 (m, 1H), 3.66 (td, J=5.5, 4.2 Hz, 2H), 3.56 (dd, J=21.8, 11.9 Hz, 2H), 3.42 (t, J=5.8 Hz, 2H), 3.27 (s, 3H), 3.21 (dd, J=12.1, 3.2 Hz, 2H). UPLC-MS: $t_R$=1.79 min (Generic method); MS (ESI) m/z calcd for $C_{16}H_{21}N_2O_5S_2$(M+H)$^+$: 385.1, found: 385.

3-[4-[4-(Pentafluoro-lambda6-sulfanyl)phenyl]sulfonylmorpholin-2-yl]benzothiophene-2-carboxamide: The title compound was prepared following GP1, from Int-1.6 (0.02 g, 0.05 mmol) and [4-(pentafluoro-lambda6-sulfanyl)phenyl]sulfonylchloride(0.02 g, 0.05 mmol). The product was obtained, after purification by silica gel flash-column chromatography with DCM/EtOAc as the eluent, as a white solid (0.01 g, 31%). $^1$H NMR (400 MHz, DMSO-$d_6$) δ 8.17 (dd, J=8.9, 1.9 Hz, 2H), 8.04-7.97 (m, 3H), 7.79 (bs, 1H), 7.44 (ddd, J=8.2, 7.1, 1.2 Hz, 1H), 7.34 (ddd, J=8.2, 7.1, 1.2 Hz, 1H), 5.51 (dd, J=10.5, 2.8 Hz, 1H), 4.11 (d, J=11.5 Hz, 1H), 3.84 (d, J=11.2 Hz, 1H), 3.78-3.56 (m, 2H), 2.88-2.72 (m, 2H). UPLC-MS: $t_R$=2.43 min (Generic method); MS (ESI) m/z calcd for $C_{19}H_{18}FN_2O_4S_3$ (M+H)$^+$: 529.1, found: 529.

3-(4-Butylsulfonylmorpholin-2-yl)benzothiophene-2-carboxamide: The title compound was prepared following GP1, from Int-1.6 (0.02 g, 0.05 mmol) and 4-butylsulfonylchloride (0.01 g, 0.05 mmol). The product was obtained, after purification by silica gel flash-column chromatography with DCM/EtOAc as the eluent, as a white solid (0.005 g, 27%). 1H NMR (400 MHz, DMSO-$d_6$) δ 8.37 (dd, J=8.9, 1.9 Hz, 1H), 8.06-7.99 (m, 2H), 7.76 (bs, 1H), 7.47 (qd, J=8.9, 1.9 Hz, 2H), 5.47 (dd, J=10.5, 2.8 Hz, 1H), 4.14 (dd, J=11.5, 2.8 Hz, 1H), 3.69 (td, J=11.7, 2.6 Hz, 1H), 3.65-3.51 (m, 2H), 3.28-3.17 (m, 2H), 3.17-3.08 (m, 2H), 1.75-1.59 (m, 2H), 1.41 (h, J=7.4 Hz, 2H), 0.91 (t, J=7.4 Hz, 3H). UPLC-MS: $t_R$=2.08 min (Generic method); MS (ESI) m/z calcd for $C_{17}H_{23}N_2O_4S_2$(M+H)$^+$: 383.1, found: 383.

3-[4-(3-Cyanophenyl)sulfonylmorpholin-2-yl]benzothiophene-2-carboxamide: The title compound was prepared following GP1, from Int-1.6 (0.02 g, 0.05 mmol) and (3-cyanophenyl)sulfonylchloride(0.01 g, 0.05 mmol). The product was obtained, after purification by silica gel flash-column chromatography with DCM/EtOAc as the eluent, as a white solid (0.01 g, 56%). 1H NMR (400 MHz, DMSO-$d_6$) δ 8.28 (t, J=1.6 Hz, 1H), 8.21 (dt, J=7.8, 1.3 Hz, 1H), 8.15 (dd, J=8.2, 1.1 Hz, 1H), 8.09 (dt, J=7.9, 1.9, 1.1 Hz, 1H), 8.06-7.94 (m, 2H), 7.83 (t, J=1.6 Hz, 1H), 7.76 (bs, 1H), 7.44 (ddd, J=8.2, 7.1, 1.2 Hz, 1H), 7.34 (ddd, J=8.3, 7.1, 1.2 Hz, 1H), 5.51 (dd, J=10.5, 2.8 Hz, 1H), 4.10 (dd, J=11.1, 3.0 Hz, 1H), 3.82 (d, J=11.4 Hz, 1H), 3.70 (t, J=10.6 Hz, 2H), 2.80-2.63 (m, 2H). UPLC-MS: $t_R$=2.04 min (Generic method); MS (ESI) m/z calcd for $C_{20}H_{10}N_3O_4S_2$(M+H)$^+$: 328.1, found: 428.

Methyl 4-[2-(2-carbamoylbenzothiophen-3-yl)morpholin-4-yl]sulfonylbenzoate: The title compound was prepared following GP1, from Int-1.6 (0.07 g, 0.19 mmol) and methyl 4-chlorosulfonylbenzoate chloride (0.04 g, 0.17 mmol). The product was obtained, after purification by silica gel flash-column chromatography with DCM/EtOAc as the eluent, as a white solid (0.03 g, 33%). $^1$H NMR (400 MHz, DMSO-$d_6$) δ 8.20-8.15 (m, 2H), 8.13 (dt, J=8.2, 1.0 Hz, 1H), 8.04-7.98 (m, 2H), 7.96-7.90 (m, 1H), 7.80 (bs, 1H), 7.44 (ddd, J=8.2, 7.1, 1.2 Hz, 1H), 7.33 (ddd, J=8.2, 7.1, 1.2 Hz, 1H), 5.51 (dd, J=10.5, 2.8 Hz, 1H), 4.11 (dd, 1H), 3.92 (s, 3H), 3.82 (d, J=11.1 Hz, 1H), 3.70 (t, J=12.2 Hz, 2H), 2.69 (t, J=11.1 Hz, 2H). UPLC-MS: $t_R$=2.12 min (Generic method); MS (ESI) m/z calcd for $C_{21}H_{21}N_2O_6S_2$ (M+H)$^+$: 461.1, found: 461.

tert-Butyl 4-[2-(2-carbamoylbenzothiophen-3-yl) morpholin-4-yl]sulfonylpiperidine-1-carboxylate: The title compound was prepared following GP1, from Int-1.6 (0.07 g, 0.19 mmol) and tert-butyl 4-chlorosulfonylpiperidine-1-carboxylate (0.05 g, 0.17 mmol). The product was obtained, after purification by silica gel flash-column chromatography with DCM/EtOAc as the eluent, as a white solid (0.05 g, 64%). $^1$H NMR (400 MHz, DMSO-$d_6$) δ 8.38 (dd, J=8.9, 1.9 Hz, 1H), 8.06-8.02 (m, 2H), 7.77 (bs, 1H), 7.47 (qd, J=8.9, 1.9 Hz, 2H), 5.44 (dd, J=10.6, 2.8 Hz, 1H), 4.12 (d, J=8.9 Hz, 1H), 4.10-3.96 (m, 2H), 3.74-3.56 (m, 3H), 3.53-3.42 (m, 1H), 3.42-3.35 (m, 1H), 2.78 (s, 2H), 2.01 (dd, J=23.1, 12.7 Hz, 2H), 1.48 (tt, J=12.2, 6.1 Hz, 3H), 1.41 (s, 9H). UPLC-MS: $t_R$=2.21 min (Generic method); MS (ESI) m/z calcd for $C_{23}H_{32}N_3O_6S_2$ (M+H)$^+$: 510.2, found:510.

3-[4-(4-Nitrophenyl)sulfonylmorpholin-2-yl]benzothiophene-2-carboxamide: The title compound was prepared following GP1, from Int-1.6 (0.07 g, 0.19 mmol) and (4-nitrophenyl)sulfonyl chloride (0.04 g, 0.17 mmol). The product was obtained, after purification by silica gel flash-column chromatography with DCM/EtOAc as the eluent, as a white solid (0.05 g, 68%). 1H NMR (400 MHz, DMSO-$d_6$) δ 8.42 (d, J=8.9 Hz, 2H), 8.16 (dt, J=8.9, 1.9 Hz, 1H), 8.07 (d, J=8.9 Hz, 2H), 8.05-7.98 (m, 2H), 7.79 (bs, 1H), 7.44 (ddd, J=8.2, 7.1, 1.2 Hz, 1H), 7.34 (ddd, J=8.3, 7.1, 1.2 Hz, 1H), 5.51 (dd, J=10.5, 2.7 Hz, 1H), 4.12 (dd, J=11.4, 3.0 Hz, 1H), 3.88 (dd, 1H), 3.76-3.64 (m, 2H), 2.88-2.74 (m, 2H). UPLC-MS: $t_R$=2.13 min (Generic method); MS (ESI) m/z calcd for $C_{19}H_{18}N_3O_6S_2$ (M+H)$^+$: 448.1, found:448.

3-[4-[2-(Trifluoromethyl)phenyl]sulfonylmorpholin-2-yl]benzothiophene-2-carboxamide: The title compound was prepared following GP1, from Int-1.6 (0.02 g, 0.05 mmol) and [2-(trifluoromethyl)phenyl]sulfonyl chloride (0.01 g, 0.05 mmol). The product was obtained, after purification by silica gel flash-column chromatography with DCM/EtOAc as the eluent, as a white solid (0.005 g, 20%). $^1$H NMR (400 MHz, DMSO-$d_6$) δ 8.26 (dt, J=8.0, 1.1 Hz, 1H), 8.16-8.12 (m, 1H), 8.08-8.04 (m, 2H), 8.02 (dt, J=8.1, 1.0 Hz, 1H), 7.95-7.89 (m, 2H), 7.76 (bs, 1H), 7.46 (ddd, J=8.2, 7.0, 1.3 Hz, 1H), 7.40 (ddd, J=8.2, 7.1, 1.3 Hz, 1H), 5.49 (dd, J=10.6, 2.9 Hz, 1H), 4.14 (dd, J=11.0, 2.8 Hz, 1H), 3.80 (dd, J=11.8, 2.6 Hz, 1H), 3.76-3.65 (m, 2H), 3.10 (td, J=12.1, 11.5, 3.5 Hz, 2H). UPLC-MS: $t_R$=2.21 min (Generic method); MS (ESI) m/z calcd for $C_{20}H_{18}F_3N_2O_4S_2$ (M+H)$^+$: 471.1, found: 471.

3-[4-[2-(Trifluoromethoxy)phenyl]sulfonylmorpholin-2-yl]benzothiophene-2-carboxamide: The title compound was prepared following GP1, from Int-1.6 (0.02 g, 0.05 mmol) and [2-(trifluoromethoxy)phenyl]sulfonyl chloride (0.01 g, 0.05 mmol). The product was obtained, after purification by silica gel flash-column chromatography with DCM/EtOAc as the eluent, as a white solid (0.006 g, 26%). $^1$H NMR (400 MHz, DMSO-$d_6$) δ 8.20 (dt, J=7.9, 1.7 Hz, 1H), 8.04-8.00 (m, 2H), 7.96 (dd, J=7.9, 1.7 Hz, 1H), 7.86 (ddd, J=8.2, 7.4, 1.7 Hz, 1H), 7.76 (bs, 1H), 7.65 (d, J=8.3, 1.5 Hz, 1H), 7.60 (ddd, J=7.7, 1.1 Hz, 1H), 7.45 (ddd, J=8.1, 7.1, 1.2 Hz, 1H), 7.38 (ddd, J=8.2, 7.1, 1.2 Hz, 1H), 5.48 (dd, J=10.6, 2.8 Hz, 1H), 4.15 (dd, J=11.1, 3.0 Hz, 1H), 3.81-3.61 (m, 3H), 3.06-2.88 (m, 2H). UPLC-MS: $t_R$=2.27 min (Generic method); MS (ESI) m/z calcd for $C_{20}H_{18}F_3N_2O_5S_2$ (M+H)$^+$: 487.1, found:487.

3-[4-(4-Hydroxyphenyl)sulfonylmorpholin-2-yl]benzothiophene-2-carboxamide: The title compound was prepared following GP1, from Int-1.6 (0.07 g, 0.19 mmol) and (4-hydroxyphenyl)sulfonyl chloride (0.04 g, 0.17 mmol). The product was obtained, after purification by silica gel flash-column chromatography with DCM/EtOAc as the eluent, as a white solid (0.05 g, 53%). $^1$H NMR (400 MHz, DMSO-$d_6$) δ 10.52 (bs, 1H), 8.08 (d, J=8.2, 1H), 8.04-7.90 (m, 2H), 7.79 (bs, 1H), 7.60-7.53 (m, 2H), 7.45-7.39 (m, 1H), 7.37-7.30 (m, 1H), 6.95-6.89 (m, 2H), 5.49 (dd, J=10.5, 2.8 Hz, 1H), 4.09 (dd, J=11.5, 3.0 Hz, 1H), 3.76-3.64 (m, 2H), 3.56 (d, J=11.7 Hz, 1H), 2.61-2.51 (m, 2H). UPLC-MS: $t_R$=1.85 min (Generic method); MS (ESI) m/z calcd for $C_{19}H_{19}N_2O_5S_2(M+H)^+$: 419.1, found: 419.

3-[4-(4-Isopropoxyphenyl)sulfonylmorpholin-2-yl]benzothiophene-2-carboxamide: To a solution of compound 068 (0.040 g, 0.10 mmol) in THF (1.0 mL), PPh$_3$ (0.052 g, 0.20 mmol) and DIAD (0.040 g, 0.20 mmol) were added. After 30 minutes of stirring at room temperature, IPA (0.012 g, 0.20 mmol) was added and the resulting solution was allowed to react overnight. The reaction was quenched by adding water and the aqueous phase was extracted with EtOAc (3×10 mL). The combined organic layers were dried over $Na_2SO_4$ and concentrated under vacuum. Subsequent flash chromatography (DCM/EtOAc 0% to 80%) afforded the title compound as white solid (0.008 g, 18%) $^1$H NMR (400 MHz, DMSO-$d_6$) δ 8.11-8.07 (m, 1H), 8.03-7.91 (m, 2H), 7.79 (bs, J=20.4 Hz, 1H), 7.68-7.60 (m, 2H), 7.46-7.39 (m, 1H), 7.35-7.29 (m, 1H), 7.13-7.05 (m, 2H), 5.49 (dd, J=10.6, 2.8 Hz, 1H), 4.72 (m, 1H), 4.09 (dd, J=11.4, 3.0 Hz, 1H), 3.75-3.65 (m, 2H), 3.59 (d, J=11.8 Hz, 1H), 2.61-2.52 (m, 2H), 1.31-1.26 (m, 6H). UPLC-MS: $t_R$=2.31 min (Generic method); MS (ESI) m z calcd for $C_{22}H_{25}N_2O_5S_2$ $(M+H)^+$: 461.1, found:461.

Synthesis of 3-benzothiophene-2-carboxylic acid intermediate (Int-2.3)

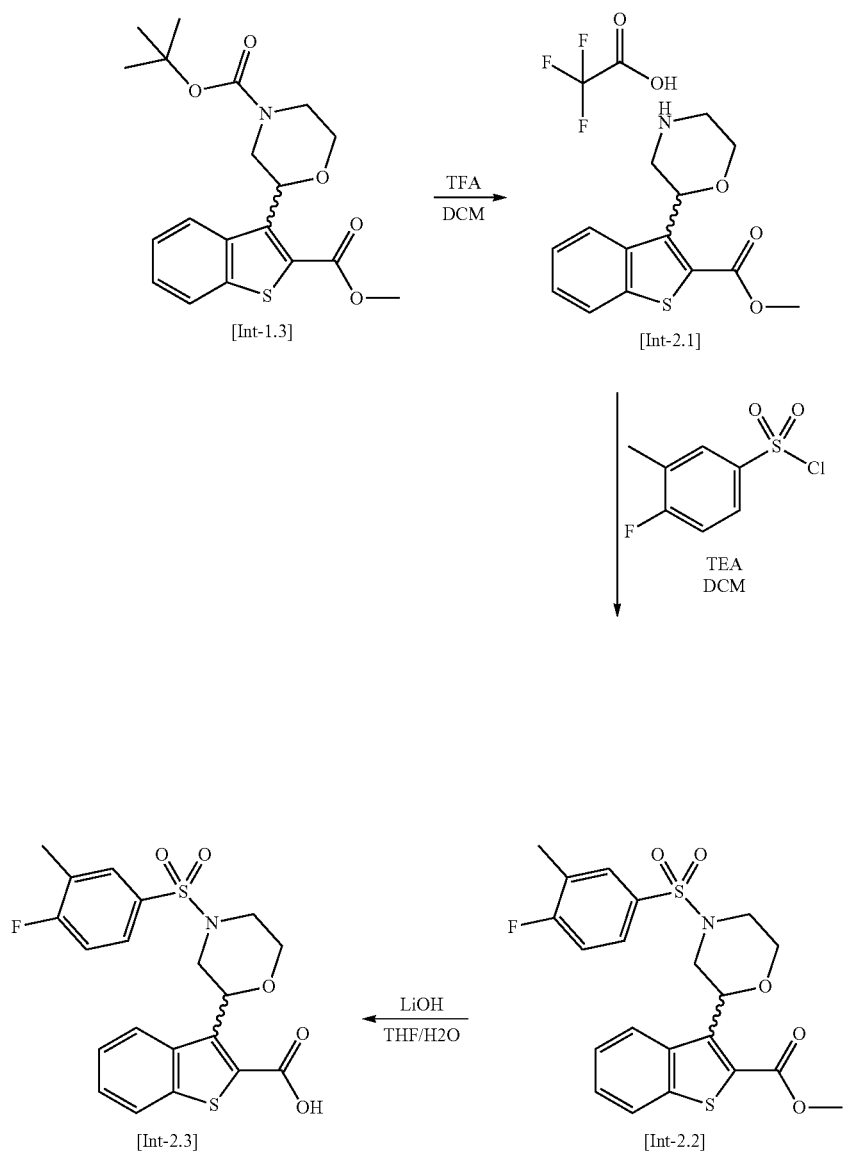

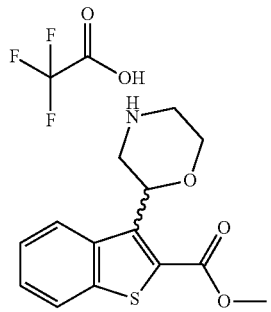

[Int-2.1] Methyl 3-morpholin-4-ium-2-ylbenzothiophene-2-carboxylate;2,2,2-trifluoroacetate: To a solution of Int-1.3 (0.4 g, 1.06 mmol) in dry DCM at 0° C., TFA was slowly added (0.347 mL, 5.30 mmol). The reaction was allowed to stir at room temperature for 7 hours. The solvent was evaporated under reduced pressure. The title compound (0.294 g, quantitative) was used in the next step without further purification. $^1$H NMR (400 MHz, DMSO-$d_6$) δ 8.48 (d, J=7.8 Hz, 1H), 8.05 (d, J=7.6 Hz, 1H), 7.50 (dt, J=33.7, 7.1 Hz, 2H), 5.99 (d, J=7.0 Hz, 1H), 4.19 (d, J=12.0 Hz, 2H), 3.89 (s, 3H), 3.52-3.38 (m, 4H). UPLC-MS: $t_R$=1.62 min (Generic method); MS (ESI) m/z calcd for $C_{14}H_{16}NO_3S$ (M+H)$^+$: 278.1, found:278.

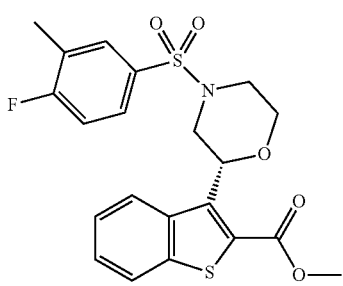

[Int-2.2] Methyl 3-[4-(4-fluoro-3-methyl-phenyl)sulfonyl morpholin-2-yl]benzothiophene-2-carboxylate: In a 20 mL round-bottomed flask, under nitrogen, Int-2.1 (0.294 g, 1.06 mmol) and Et$_3$N (0.161 mL, 1.16 mmol) were added in dry DCM, followed by 4-fluoro-3-methylbenzenesulfonyl chloride (0.201 g, 0.96 mmol). After 1 hour at room temperature, the mixture was quenched with water, and the organic layer was separated and washed with brine, dried over Na$_2$SO$_4$, filtered and concentrated. The crude product was purified with CombiFlash (DCM/EtOAc) to yield the title compound (0.433 g, quantitative). $^1$H NMR (400 MHz, DMSO-$d_6$) δ 8.29 (dt, J=8.4, 1.0 Hz, 1H), 8.02 (dt, J=8.1, 0.9 Hz, 1H), 7.76 (dd, J=8.2, 1.2 Hz, 1H), 7.70-7.59 (m, 1H), 7.50 (ddd, J=8.2, 7.0, 1.2 Hz, 1H), 7.42-7.32 (m, 2H), 5.76 (dd, J=10.4, 2.7 Hz, 1H), 4.13 (dd, J=11.6, 2.9 Hz, 1H), 3.92 (s, 3H), 3.82-3.58 (m, 3H), 2.69 (td, J=11.7, 3.3 Hz, 1H), 2.60 (t, J=11.7 Hz, 1H). UPLC-MS: $t_R$=2.79 min (Generic method); MS (ESI) m/z calcd for $C_{21}H_{21}FNO_5S_2$ (M+H)$^+$: 450.1, found:450.

[Int-2.3]

[Int-2.3] 3-[4-(4-Fluoro-3-methyl-phenyl)sulfonylmorpholin-2-yl]benzothiophene-2-carboxylic acid: To a solution of Int-2.2 (0.433 g, 0.99 mmol) in THF (15 mL),aqueous LiOH 1N (5 mL) was added dropwise and the reaction was stirred overnight at room temperature. The reaction was quenched upon addition of HCl 2N, until pH=4/5, and the resulting aqueous phase was extracted with EtOAc (3×15 mL). The combined organic layers were washed with brine, dried, filtered and concentrated to give a crude product, which was purified with CombiFlash (DCM/MeOH 95:5+ 5% AcOH), to obtain the desired compound as a white powder (0.384 g, 89%). $^1$H NMR (400 MHz, DMSO-$d_6$) δ 8.24 (d, J=8.3 Hz, 1H), 7.98 (d, J=8.1 Hz, 1H), 7.74 (dd, J=7.1, 2.4 Hz, 1H), 7.63 (ddd, J=8.0, 4.8, 2.4 Hz, 1H), 7.46 (ddd, J=8.2, 7.0, 1.2 Hz, 1H), 7.40-7.26 (m, 2H), 5.81 (dd, J=10.4, 2.7 Hz, 1H), 4.11 (dd, J=11.6, 3.0 Hz, 1H), 3.78-3.57 (m, 3H), 2.65 (td, J=11.8, 3.3 Hz, 1H), 2.55 (t, J=11.0 Hz, 1H), 2.27 (s, 3H). UPLC-MS: $t_R$=1.91 min (Generic method); MS (ESI) m/z calcd for $C_{20}H_{19}FNO_5S_2$ (M+H)$^+$: 436.1, found: 436.

General Protocol for Carboxy Amide Derivatives Synthesis (GP2).

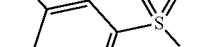

[Int-2.3]

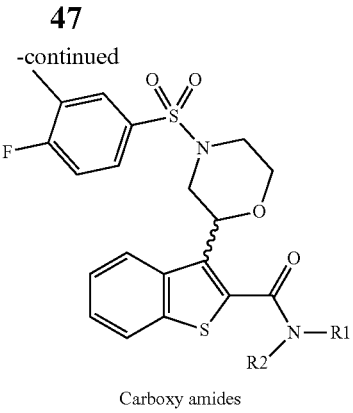

Carboxy amides

To a solution of Int-2.3 (1.0 eq) in dry DMF (0.1 M) cooled to 0° C., HATU (1.5 eq) and DIPEA (4.0 eq) were sequentially added. After 10 minutes, the desired amine (2.0 eq) was added and the mixture stirred for 30 min at room temperature. Sat. aq. NH$_4$Cl was added to quench the reaction and the mixture was extracted with EtOAc (3×). Collected organic layers were washed with brine, dried (Na$_2$SO$_4$), filtered and evaporated to give a crude product, which was purified with CombiFlash (DCM/EtOAc) to obtain the desired compounds in good yields.

3-[4-(4-Fluoro-3-methyl-phenyl)sulfonylmorpholin-2-yl]-N,N-dimethyl-benzothiophene-2-carboxamide: The title compound was prepared following GP2, from Int-2.3 (0.05 g, 0.11 mmol) and dimethyl amine (2.0 M THF solution, 11.0 µL, 0.22 mmol). The product was obtained, after purification by silica gel flash-column chromatography with DCM/EtOAc as the eluent, as a white solid (0.03 g, 63%). $^1$H NMR (400 MHz, DMSO-d$_6$) δ 8.03-7.99 (m, 1H), 7.98-7.94 (m, 1H), 7.74 (dd, J=7.8, 2.7 Hz, 1H), 7.63 (ddd, J=7.8, 4.8, 2.7 Hz, 1H), 7.46-7.37 (m, 3H), 4.91 (dd, J=10.6, 2.7 Hz, 1H), 4.04 (dd, J=10.6, 2.7 Hz, 1H), 3.76 (td, J=11.6, 2.5 Hz, 1H), 3.63 (t, J=12.9 Hz, 2H), 2.94 (d, 6H), 2.72-2.56 (m, 2H), 2.31 (s, 3H). UPLC-MS: t$_R$=2.45 min (Generic method); MS (ESI) m/z calcd for C$_{22}$H$_{24}$FN$_2$O$_4$S$_2$ (M+H)$^+$: 463.1, found: 463.

3-[4-(4-Fluoro-3-methyl-phenyl)sulfonylmorpholin-2-yl]-N-methyl-benzothiophene-2-carboxamide: The title compound was prepared following GP2, from Int-2.3 (0.05 g, 0.11 mmol) and methyl amine (2.0 M THF solution, 11.0 µL, 0.22 mmol). The product was obtained, after purification by silica gel flash-column chromatography with DCM/EtOAc as the eluent, as a white solid (0.02 g, 47%). $^1$H NMR (400 MHz, DMSO-d$_6$) δ 8.46 (d, J=4.7 Hz, 1H), 8.11 (dt, J=8.2, 1.1 Hz, 1H), 7.99 (dt, J=8.2, 1.0 Hz, 1H), 7.79-7.72 (m, 1H), 7.63 (ddd, J=7.6, 4.6, 2.5 Hz, 1H), 7.42 (ddd, J=8.1, 7.0, 1.2 Hz, 1H), 7.40-7.35 (m, 1H), 7.33 (ddd, J=8.2, 6.5, 1.3 Hz, 1H), 5.42 (dd, J=10.5, 2.8 Hz, 1H), 4.07 (dd, J=10.9, 3.0 Hz, 1H), 3.77 (d, J=11.2 Hz, 1H), 3.71-3.54 (m, 2H), 2.77 (d, J=4.5 Hz, 3H), 2.70-2.56 (m, 2H), 2.30 (d, J=2.2 Hz, 3H). UPLC-MS: t$_R$=2.38 min (Generic method); MS (ESI) m/z calcd for C$_{21}$H$_{22}$FN$_2$O$_4$S$_2$ (M+H)$^+$: 449.1, found: 449.

3-[4-(4-Fluoro-3-methyl-phenyl)sulfonylmorpholin-2-yl]-N-(2-hydroxyethyl) benzothiophene-2-carboxamide: The title compound was prepared following GP2, from Int-2.3 (0.04 g, 0.08 mmol) and ethanolamine (10.0 µL, 0.16 mmol). The product was obtained, after purification by silica gel flash-column chromatography with DCM/EtOAc as the eluent, as a white solid (0.02 g, 38%). $^1$H NMR (400 MHz, DMSO-d$_6$) δ 8.53 (t, J=5.6 Hz, 1H), 8.10 (dd, J=8.2, 1.1 Hz, 1H), 7.99 (dd, J=8.2, 1.1 Hz, 1H), 7.74 (dt, J=8.2, 1.1 Hz, 1H), 7.68-7.58 (m, 1H), 7.48-7.29 (m, 3H), 5.40 (dd, J=10.6, 2.8 Hz, 1H), 4.75 (t, J=5.5 Hz, 1H), 4.08 (dd, J=11.5, 2.8 Hz, 1H), 3.84-3.66 (m, 2H), 3.61 (dd, J=12.0 Hz, 1H), 3.54-3.40 (m, 2H), 3.29-3.20 (m, 1H), 2.74-2.58 (m, 2H), 2.29 (s, 3H). UPLC-MS: t$_R$=2.21 min (Generic method); MS (ESI) m/z calcd for C$_{22}$H$_{24}$FN$_2$O$_5$S$_2$ (M+H)$^+$: 479.1, found: 479.

N-Ethyl-3-[4-(4-fluoro-3-methyl-phenyl)sulfonyl morpholin-2-yl]benzothiophene-2-carboxamide: The title compound was prepared following GP2, from Int-2.3 (0.05 g, 0.11 mmol) and ethyl amine (2.0 M THF solution, 11.0 µL, 0.22 mmol). The product was obtained, after purification by silica gel flash-column chromatography with DCM/EtOAc as the eluent, as a white solid (0.01 g, 18%). $^1$H NMR (400 MHz, DMSO-d$_6$) δ 8.54 (t, J=5.6 Hz, 1H), 8.11 (d, J=8.1 Hz, 1H), 7.98 (d, J=8.1 Hz, 1H), 7.75 (dd, J=8.2, 1.1 Hz, 1H), 7.69-7.57 (m, 1H), 7.49-7.27 (m, 3H), 6.97 (bs, 1H), 5.39 (dd, J=10.5, 2.8 Hz, 1H), 4.09 (dd, J=11.8, 3.0 Hz, 1H), 3.80-3.53 (m, 3H), 3.30-3.18 (m, 2H), 2.63 (t, J=11.0 Hz, 2H), 2.29 (s, 3H). UPLC-MS: t$_R$=2.46 min (Generic method); MS (ESI) m/z calcd for C$_{22}$H$_{24}$FN$_2$O$_4$S$_2$ (M+H)$^+$: 463.1, found: 463.

3-[4-(4-Fluoro-3-methyl-phenyl)sulfonylmorpholin-2-yl]-N-isopropyl-benzothiophene-2-carboxamide: The title compound was prepared following GP2, from Int-2.3 (0.05 g, 0.11 mmol) and isopropyl amine (17.8 µL, 0.22 mmol). The product was obtained, after purification by silica gel flash-column chromatography with DCM/EtOAc as the eluent, as a white solid (0.04 g, 73%). $^1$H NMR (400 MHz, DMSO-d$_6$) δ 8.40 (d, J=7.7 Hz, 1H), 8.09 (dt, J=8.0, 1.0 Hz, 1H), 7.98 (dt, J=8.0, 1.0 Hz, 1H), 7.74 (dd, J=7.7, 2.4 Hz, 1H), 7.63 (ddd, J=7.7, 4.9, 2.4 Hz, 1H), 7.46-7.30 (m, 3H), 5.33 (dd, J=10.5, 2.8 Hz, 1H), 4.10 (dd, J=11.6, 2.9 Hz, 1H), 4.01 (q, J=6.7 Hz, 1H), 3.78-3.68 (m, 1H), 3.63 (d, J=11.9 Hz, 1H), 2.71-2.53 (m, 2H), 2.29 (s, 3H), 1.13 (d, J=6.6 Hz, 3H), 1.06 (d, J=6.6 Hz, 3H). UPLC-MS: t$_R$=2.57 min (Generic method); MS (ESI) m/z calcd for C$_{23}$H$_{26}$FN$_2$O$_4$S$_2$ (M+H)$^+$: 477.1, found: 477.

Pure enantiomers were obtained from the corresponding racemates, after separation by chiral column chromatography.

3-1[(R)-4-(4-Fluoro-3-methyl-phenyl) sulfonylmorpholin-2-yl]benzothiophene-2-carboxamide: The title compound was obtained from racemic 001, using a Daicel ChiralCel OD-H column (250×4.6mmID, particle size 5 µm) at 25° C. Mobile phase: Heptane-EtOH (90:10). Flow Rate: 1 mL/min; UV: 278 nm. $^1$H NMR (400 MHz, DMSO-d$_6$) δ 8.14 (d, J=8.2, 1.1 Hz, 1H), 8.09-7.93 (m, 2H), 7.87-7.72 (m, 2H), 7.69-7.60 (m, 1H), 7.49-7.32 (m, 3H), 5.51 (dd, J=10.5, 2.8 Hz, 1H), 4.11 (d, J=11.6, 2.9 Hz, 1H), 3.85-3.56 (m, 3H), 2.67 (td, J=10.9, 3.7 Hz, 2H), 2.32 (s, 3H). UPLC-MS: t$_R$=2.33 min (Generic method); MS (ESI) m/z calcd for C$_{20}$H$_{20}$FN$_2$O$_4$S$_2$ (M+H)$^+$: 435.1, found: 435. Chiral HPLC: t$_R$=29.995 min, >99.5% ee.

3-[(S)-4-(4-Fluoro-3-methyl-phenyl) sulfonylmorpholin-2-yl]benzothiophene-2-carboxamide: The title compound was obtained from racemic 001, using a Daicel ChiralCel OD-H column (250×4.6mmID, particle size 5 µm) at 25° C. Mobile phase: Heptane-EtOH (90:10). Flow Rate: 1 mL/min; UV: 278 nm: $^1$H NMR (400 MHz, DMSO-d$_6$) δ 8.14 (d, J=8.2, 1.1 Hz, 1H), 8.09-7.93 (m, 2H), 7.87-7.72 (m, 2H), 7.69-7.60 (m, 1H), 7.49-7.32 (m, 3H), 5.51 (dd, J=10.5, 2.8 Hz, 1H), 4.11 (d, J=11.6, 2.9 Hz, 1H), 3.85-3.56 (m, 3H), 2.67 (td, J=10.9, 3.7 Hz, 2H), 2.32 (s, 3H). UPLC-MS: t$_R$=2.33 min (Generic method); MS (ESI) m/z calcd for C$_{20}$H$_{20}$FN$_2$O$_4$S$_2$ (M+H)$^+$: 435.1, found: 435. Chiral HPLC: t$_R$=36.540 min, >99.5% ee.

3-[(R)-4-[4-(Trifluoromethyl)phenyl]sulfonylmorpholin-2-yl]benzothiophene-2-carboxamide: The title compound was obtained from racemic 011, using a Daicel ChiralCel OD-H column (250×4.6mmID, particle size 5 μm) at 25° C. Mobile phase: Heptane-EtOH (90:10). Flow Rate: 1 mL/min; UV: 278 nm. 1H NMR (400 MHz, DMSO-$d_6$) δ 8.15 (dd, J=8.2, 1.0 Hz, 1H), 8.01 (s, 4H), 8.01-7.99 (m, 2H), 7.79 (bs, 1H), 7.44 (ddd, J=8.2, 7.1, 1.2 Hz, 1H), 7.34 (ddd, J=8.2, 7.1, 1.1 Hz, 1H), 5.51 (dd, J=10.5, 2.8 Hz, 1H), 4.11 (d, J=10.9 Hz, 1H), 3.70 (t, J=12.1 Hz, 2H), 3.84 (d, J=11.4 Hz, 1H), 2.83-2.62 (m, 2H). UPLC-MS: $t_R$=2.40 min (Generic method); MS (ESI) m/z calcd for $C_{20}H_{18}F_3N_2O_4S_2$ (M+H)$^+$: 471.1, found:471. Chiral HPLC: $t_R$=39.324 min, >99.5% ee.

3-[(S)-4-[4-(Trifluoromethyl)phenyl]sulfonylmorpholin-2-yl]benzothiophene-2-carboxamide: The title compound was obtained from racemic 011, using a Daicel ChiralCel OD-H column (250×4.6mmID, particle size 5 μm) at 25° C. Mobile phase: Heptane-EtOH (90:10). Flow Rate: 1 mL/min; UV: 278 nm. 1H NMR (400 MHz, DMSO-$d_6$) δ 8.15 (dd, J=8.2, 1.0 Hz, 1H), 8.01 (s, 4H), 8.01-7.99 (m, 2H), 7.79 (bs, 1H), 7.44 (ddd, J=8.2, 7.1, 1.2 Hz, 1H), 7.34 (ddd, J=8.2, 7.1, 1.1 Hz, 1H), 5.51 (dd, J=10.5, 2.8 Hz, 1H), 4.11 (d, J=10.9 Hz, 1H), 3.70 (t, J=12.1 Hz, 2H), 3.84 (d, J=11.4 Hz, 1H), 2.83-2.62 (m, 2H). UPLC-MS: $t_R$=2.40 min (Generic method); MS (ESI) m/z calcd for $C_{20}H_{18}F_3N_2O_4S_2$ (M+H)$^+$: 471.1, found:471. Chiral HPLC: $t_R$=30.875 min, >99.5% ee.

3-[(S)-4-[3-Fluoro-4-(trifluoromethyl) phenyl]sulfonylmorpholin-2-yl]benzothiophene-2-carboxamide: The title compound was obtained from racemic 041, using a Daicel ChiralCel OD-H column (250×4.6mmID, particle size 5 μm) at 25° C. Mobile phase: Heptane-EtOH (90:10). Flow Rate: 1 mL/min; UV: 278 nm. $^1$H NMR (400 MHz, DMSO-$d_6$) δ 8.19 (d, J=8.2 Hz, 1H), 8.09-7.95 (m, 4H), 7.81 (d, J=8.3 Hz, 1H), 7.76 (bs, 1H), 7.44 (ddd, J=8.2, 7.0, 1.2 Hz, 1H), 7.34 (ddd, J=8.2, 7.1, 1.2 Hz, 1H), 5.50 (dd, J=10.6, 2.8 Hz, 1H), 4.10 (dd, J=11.4, 3.0 Hz, 1H), 3.84 (d, J=11.3 Hz, 1H), 3.77-3.61 (m, 2H), 2.95-2.77 (m, 2H). UPLC-MS: $t_R$=2.50 min (Generic method); MS (ESI) m/z calcd for $C_{20}H_{17}F_4N_2O_4S_2$ (M+H)$^+$: 489.1, found: 489. Chiral HPLC: $t_R$=36.123 min, >99.5% ee.

3-[(R)-4-[3-Fluoro-4-(trifluoromethyl) phenyl]sulfonylmorpholin-2-yl]benzothiophene-2-carboxamide: The title compound was obtained from racemic 041, using a Daicel ChiralCel OD-H column (250×4.6mmID, particle size 5 μm) at 25° C. Mobile phase: Heptane-EtOH (90:10). Flow Rate: 1 mL/min; UV: 278 nm; $^1$H NMR (400 MHz, DMSO-$d_6$) δ 8.19 (d, J=8.2 Hz, 1H), 8.09-7.95 (m, 4H), 7.81 (d, J=8.3 Hz, 1H), 7.76 (bs, 1H), 7.44 (ddd, J=8.2, 7.0, 1.2 Hz, 1H), 7.34 (ddd, J=8.2, 7.1, 1.2 Hz, 1H), 5.50 (dd, J=10.6, 2.8 Hz, 1H), 4.10 (dd, J=11.4, 3.0 Hz, 1H), 3.84 (d, J=11.3 Hz, 1H), 3.77-3.61 (m, 2H), 2.95-2.77 (m, 2H). UPLC-MS: $t_R$=2.50 min (Generic method); MS (ESI) m/z calcd for $C_{20}H_{17}F_4N_2O_4S_2$ (M+H)$^+$: 489.1, found: 489. Chiral HPLC: $t_R$=27.703 min, >99.5% ee.

3-[(S)-4-[(2-Methyl-1,3-benzoxazol-6-yl) sulfonyl]morpholin-2-yl]benzothiophene-2-carboxamide: The title compound was obtained from racemic 034, using a Daicel ChiralCel OD-H column (250×4.6mmID, particle size 5 μm) at 25° C. Mobile phase: Heptane-EtOH (50:50). Flow Rate: 1 mL/min; UV: 278 nm. $^1$H NMR (400 MHz, DMSO-$d_6$) δ 8.13 (dd, J=1.7, 0.5 Hz, 1H), 8.07 (dt, J=8.3, 1.0 Hz, 1H), 8.03-7.94 (m, 2H), 7.86 (d, J=8.4 Hz, 1H), 7.82-7.66 (m, 2H), 7.40 (ddd, J=8.2, 7.1, 1.2 Hz, 1H), 7.28 (ddd, J=8.2, 7.1, 1.2 Hz, 1H), 5.50 (dd, J=10.5, 2.8 Hz, 1H), 4.08 (d, J=11.3 Hz, 1H), 3.79 (d, J=11.2 Hz, 1H), 3.68 (t, J=12.0 Hz, 2H), 2.66 (s, 3H), 2.64-2.56 (m, 2H). UPLC-MS: $t_R$=2.05 min (Generic method); MS (ESI) m/z calcd for $C_{21}H_{20}N_3O_5S_2$ (M+H)$^+$: 458.1, found: 458. Chiral HPLC: $t_R$=11.8 min, >98.5% ee.

3-[(R)-4-[(2-Methyl-1,3-benzoxazol-6-yl) sulfonyl]morpholin-2-yl]benzothiophene-2-carboxamide: The title compound was obtained from racemic 034, using a Daicel ChiralCel OD-H column (250×4.6mmID, particle size 5 μm) at 25° C. Mobile phase: Heptane-EtOH (50:50). Flow Rate: 1 mL/min; UV: 278 nm. $^1$H NMR (400 MHz, DMSO-$d_6$) δ 8.13 (dd, J=1.7, 0.5 Hz, 1H), 8.07 (dt, J=8.3, 1.0 Hz, 1H), 8.03-7.94 (m, 2H), 7.86 (d, J=8.4 Hz, 1H), 7.82-7.66 (m, 2H), 7.40 (ddd, J=8.2, 7.1, 1.2 Hz, 1H), 7.28 (ddd, J=8.2, 7.1, 1.2 Hz, 1H), 5.50 (dd, J=10.5, 2.8 Hz, 1H), 4.08 (d, J=11.3 Hz, 1H), 3.79 (d, J=11.2 Hz, 1H), 3.68 (t, J=12.0 Hz, 2H), 2.66 (s, 3H), 2.64-2.56 (m, 2H). UPLC-MS: $t_R$=2.05 min (Generic method); MS (ESI) m/z calcd for $C_{21}H_{20}N_3O_5S_2$(M+H)$^+$: 458.1, found: 458. Chiral HPLC: $t_R$=8.3 min, >99.5% ee.

3-[(S)-4-(3-Fluoro-4-methyl-phenyl) sulfonylmorpholin-2-yl]benzothiophene-2-carboxamide: The title compound was obtained from racemic 026, using a Daicel ChiralCel OD-H column (250×4.6mmID, particle size 5 μm) at 25° C. Mobile phase: Heptane-EtOH (90:10). Flow Rate: 1 mL/min; UV: 278 nm. 1H NMR (400 MHz, DMSO-$d_6$) δ 8.22-8.13 (m, 2H), 8.04 (dd, J=6.7, 2.3 Hz, 1H), 8.01-7.95 (m, 2H), 7.82-7.66 (m, 3H), 7.42 (ddd, J=8.2, 7.1, 1.2 Hz, 1H), 7.33 (ddd, J=8.2, 7.1, 1.2 Hz, 1H), 5.48 (dd, J=10.5, 2.8 Hz, 1H), 4.15-4.02 (m, 1H), 3.85-3.74 (m, 1H), 3.74-3.62 (m, 2H), 2.78 (td, J=11.8, 11.2, 3.4 Hz, 2H). UPLC-MS: $t_R$=2.46 min (Generic method); MS (ESI) m/z calcd for $C_{20}H_{17}F_4N_2O_4S_2$ (M+H)$^+$: 489.1, found: 489. Chiral HPLC: $t_R$=15.2 min, >97.8% ee.

3-[(R) -4-(3-Fluoro-4-methyl-phenyl) sulfonylmorpholin-2-yl]benzothiophene-2-carboxamide: The title compound was obtained from racemic 041, using a Daicel ChiralCel OD-H column (250×4.6mmID, particle size 5 μm) at 25° C. Mobile phase: Heptane-EtOH (90:10). Flow Rate: 1 mL/min; UV: 278 nm. $^1$H NMR (400 MHz, DMSO-$d_6$) δ 8.22-8.13 (m, 2H), 8.04 (dd, J=6.7, 2.3 Hz, 1H), 8.01-7.95 (m, 2H), 7.82-7.66 (m, 3H), 7.42 (ddd, J=8.2, 7.1, 1.2 Hz, 1H), 7.33 (ddd, J=8.2, 7.1, 1.2 Hz, 1H), 5.48 (dd, J=10.5, 2.8 Hz, 1H), 4.15-4.02 (m, 1H), 3.85-3.74 (m, 1H), 3.74-3.62 (m, 2H), 2.78 (td, J=11.8, 11.2, 3.4 Hz, 2H). UPLC-MS: $t_R$=2.46 min (Generic method); MS (ESI) m/z calcd for $C_{20}H_{17}F_4N_2O_4S_2$ (M+H)$^+$: 489.1, found: 489. Chiral HPLC: $t_R$=10.7 min, >97.8% ee.

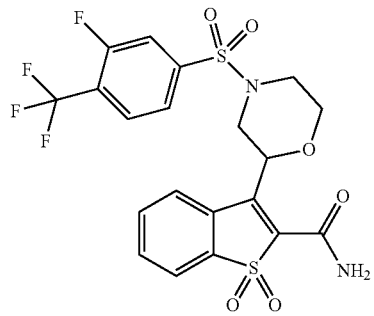 [SMILES: NC(=O)C1=C(C2CN(S(=O)(=O)c3ccc(C(F)(F)F)c(F)c3)CCO2)c2ccccc2S1(=O)=O]

3-[4-[3-Fluoro-4-(trifluoromethyl)phenyl]sulfonyl morpholin-2-yl]-1,1-dioxo-benzothiophene-2-carboxamide: To a solution of compound 041 (0.074 g, 0.15 mmol) in DCM (2.1 mL) m-CPBA (0.1 g, 0.45 mmol)was added at 0° C. The solution was stirred overnight at room temperature, washed with sat. sol. NaHCO$_3$ and dried over Na$_2$SO$_4$. The crude product was passed through a pad of silica gel using cyclohexane/AcOEt 0% to 40% as eluent. The title compound was obtained by recrystallization in CH$_3$CN/H$_2$O (0.016 g, 20%), as white solid. $^1$H NMR (400 MHz, DMSO-d$_6$) δ 8.16 (bs, 1H), 8.09-8.04 (m, 1H), 8.02 (dd, J=5.7, 3.0 Hz, 1H), 7.98 (d, J=10.3 Hz, 1H), 7.96-7.92 (m, 1H), 7.82 (d, J=8.2 Hz, 1H), 7.73-7.67 (m, 2H), 7.56 (bs, 1H), 5.12 (dd, J=10.6, 2.6 Hz, 1H), 4.06 (dd, J=11.1, 2.8 Hz, 1H), 3.90 (d, J=11.6 Hz, 1H), 3.69 (t, J=10.7 Hz, 2H), 2.94-2.76 (m, 2H). UPLC-MS: t$_R$=2.02 min (Generic method); MS (ESI) m/z calcd for C$_{20}$H$_{17}$F$_4$N$_2$O$_6$S$_2$ (M+H)$^+$: 521.0, found: 521.

Methods

Fluorescence Assay for CFTR Activity

Mutant CFTR activity was determined with the functional assay based on the halide-sensitive yellow fluorescent protein, HS—YFP (Galietta et al., FEBS Lett 499:220-224, 2001). CFBE41o- and FRT cells with stable expression of mutant CFTR and HS—YFP were plated on clear-bottom 96-well black microplates (Code 3603, Corning Life Sciences) at a density of 50,000 cells/well and kept at 37° C. in 5% CO$_2$ for 24 hours.

For the corrector assay, cells were treated for further 24 hours with test compounds, vehicle (DMSO), or the positive control VX-809. After treatment, the culture medium was removed and cells in each well were stimulated for 30 min at 37° C. with 60 µL PBS (containing 137 mM NaCl, 2.7 mM KCl, 8.1 mM Na$_2$HPO$_4$, 1.5 mM KH$_2$PO$_4$, 1 mM CaCl$_2$, and 0.5 mM MgCl$_2$) plus forskolin (20 µM) and genistein (50 µM).

For determination of potentiator activity on F508del-CFTR, cells were incubated for 24 hours at 27° C. to allow trafficking of the mutant protein to plasma membrane. Cells were then stimulated with for 30 min with PBS containing forskolin (20 µM) plus the compound to be tested at the desired concentration. For determination of potentiator activity on G551D-CFTR or G1349D-CFTR, cells were directly stimulated with forskolin plus test compound without previous incubation at low temperature. At the time of assay, microplates carrying CFBE41o- or FRT cells were transferred to microplate readers (BMG Labtech) equipped with high-quality excitation (HQ500/20×: 500±10 nm) and emission (HQ535/30M: 535±15 nm) filters for YFP (Chroma Technology). The assay consisted of a continuous 14 s fluorescence reading with 2 s before and 12 s after injection of an iodide-containing solution (165 µL of a modified PBS containing I$^-$ instead of Cl$^-$; final I$^-$ concentration in the well: 100 mM). Data were normalized to the initial background-subtracted fluorescence. Enhanced CFTR activity, induced by correctors and/or potentiators, results in accelerated I$^-$ influx that in turn causes faster HS—YFP quenching (Pedemonte et al., *Mol Pharmacol* 68:1736-1746, 2005; Pedemonte et al., *J Clin Invest* 115:2564-2571, 2015). To determine fluorescence quenching rate associated with I$^-$ influx, the final 10 s of data for each well were fitted with an exponential function to extrapolate initial slope (dF/dt).

EC$_{50}$ obtained are illustrated in Table 1 wherein+: EC$_{50}$>2 µM; ++: 1.0 µM <EC$_{50}$<2 µM; +++: EC$_{50}$<1 µM.

| # | Structure | Substance Name | Molecular Formula | Activity |
|---|---|---|---|---|
| 001 | 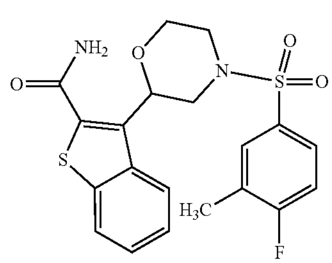 [SMILES: Cc1cc(S(=O)(=O)N2CCOC(c3c(C(N)=O)sc4ccccc34)C2)ccc1F] | rac-3-[4-(4-fluoro-3-methyl-benzenesulfonyl)-morpholin-2-yl]-benzo[b]thiophene-2-carboxylic acid amide | C20 H19 F N2 O4 S2 | + |
| 002 | 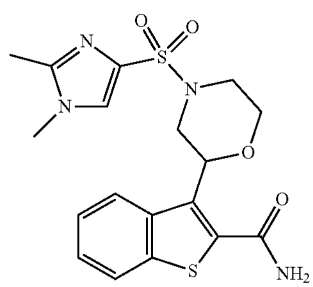 [SMILES: Cc1nc(S(=O)(=O)N2CCOC(c3c(C(N)=O)sc4ccccc34)C2)cn1C] | rac-3-[4-(1,2-dimethylimidazol-4-yl)sulfonylmorpholin-2-yl]benzothiophene-2-carboxamide | C18 H20 N4 O4 S2 | + |
| 003 | 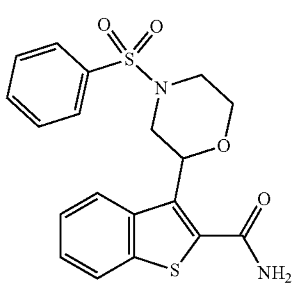 [SMILES: NC(=O)c1sc2ccccc2c1C1CN(S(=O)(=O)c2ccccc2)CCO1] | rac-3-[4-(benzenesulfonyl)morpholin-2-yl]benzothiophene-2-carboxamide | C19 H18 N2 O4 S2 | + |

-continued

| # | Structure | Substance Name | Molecular Formula | Activity |
|---|---|---|---|---|
| 004 | 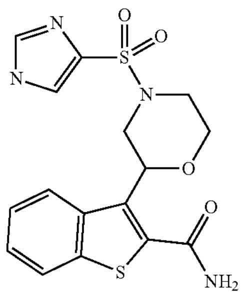 [SMILES: NC(=O)c1sc2ccccc2c1C1CN(S(=O)(=O)c2c[nH]cn2)CCO1] | rac-3-[4-(1H-imidazol-4-ylsulfonyl)morpholin-2-yl]benzothiophene-2-carboxamide | C16 H16 N4 O4 S2 | + |
| 005 | 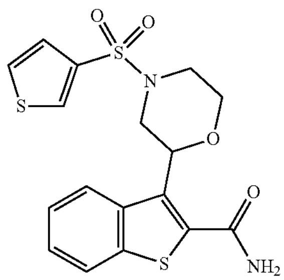 [SMILES: NC(=O)c1sc2ccccc2c1C1CN(S(=O)(=O)c2ccsc2)CCO1] | rac-3-[4-(3-thienylsulfonyl)morpholin-2-yl]benzothiophene-2-carboxamide | C17 H16 N2 O4 S3 | + |
| 006 | 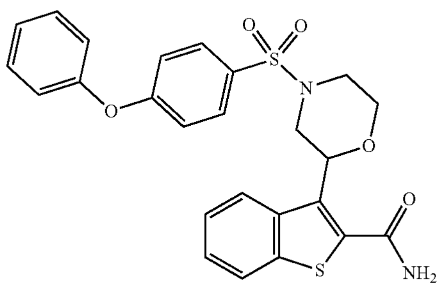 [SMILES: NC(=O)c1sc2ccccc2c1C1CN(S(=O)(=O)c2ccc(Oc3ccccc3)cc2)CCO1] | rac-3-[4-(4-phenoxyphenyl)sulfonylmorpholin-2-yl]benzothiophene-2-carboxamide | C25 H22 N2 O5 S2 | +++ |
| 007 | 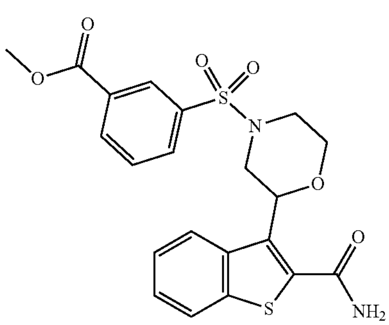 [SMILES: COC(=O)c1cccc(S(=O)(=O)N2CCOC(c3c(C(N)=O)sc4ccccc34)C2)c1] | rac-methyl 3-[2-(2-carbamoylbenzothiophen-3-yl)morpholin-4-yl]sulfonylbenzoate | C21 H20 N2 O6 S2 | + |
| 008 | 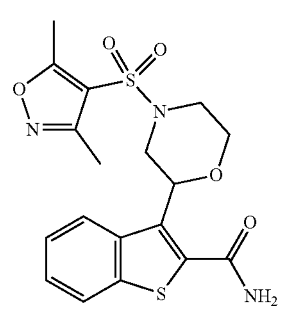 [SMILES: Cc1noc(C)c1S(=O)(=O)N1CCOC(c2c(C(N)=O)sc3ccccc23)C1] | rac-3-[4-(3,5-dimethylisoxazol-4-yl)sulfonylmorpholin-2-yl]benzothiophene-2-carboxamide | C18 H19 N3 O5 S2 | + |

| # | Structure | Substance Name | Molecular Formula | Activity |
|---|---|---|---|---|
| 009 | 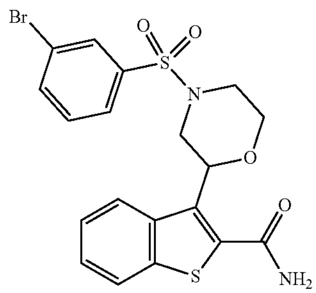 [SMILES: NC(=O)c1sc2ccccc2c1C1CN(S(=O)(=O)c2cccc(Br)c2)CCO1] | rac-3-[4-(3-bromophenyl)sulfonylmorpholin-2-yl]benzothiophene-2-carboxamide | C19 H17 Br N2 O4 S2 | + |
| 010 | 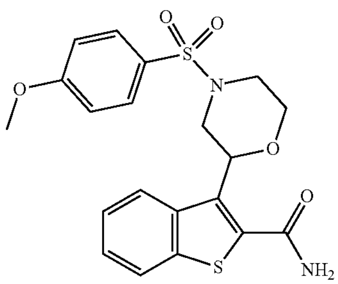 [SMILES: COc1ccc(S(=O)(=O)N2CCOC(c3c(C(N)=O)sc4ccccc34)C2)cc1] | rac-3-[4-(4-methoxyphenyl)sulfonylmorpholin-2-yl]benzothiophene-2-carboxamide | C20 H20 N2 O5 S2 | ++ |
| 011 | 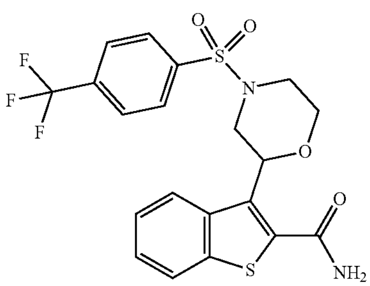 | rac-3-[4-[4-(trifluoromethyl)phenyl]sulfonylmorpholin-2-yl]benzothiophene-2-carboxamide | C20 H17 F3 N2 O4 S2 | ++ |
| 012 | 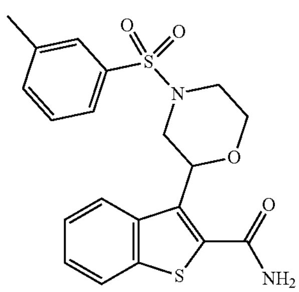 [SMILES: Cc1cccc(S(=O)(=O)N2CCOC(c3c(C(N)=O)sc4ccccc34)C2)c1] | rac-3-[4-(m-tolylsulfonyl)morpholin-2-yl]benzothiophene-2-carboxamide | C20 H20 N2 O4 S2 | ++ |
| 013 | 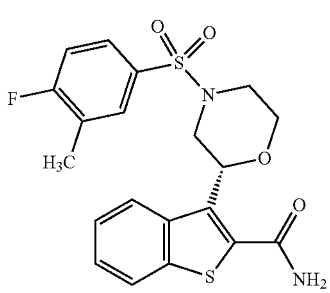 [SMILES: Cc1cc(S(=O)(=O)N2CCO[C@H](c3c(C(N)=O)sc4ccccc34)C2)ccc1F] | 3-[(R)-4-(4-fluoro-3-methyl-phenyl)sulfonylmorpholin-2-yl]benzothiophene-2-carboxamide | C20 H19 F N2 O4 S2 | + |

-continued

| # | Structure | Substance Name | Molecular Formula | Activity |
|---|---|---|---|---|
| 014 | 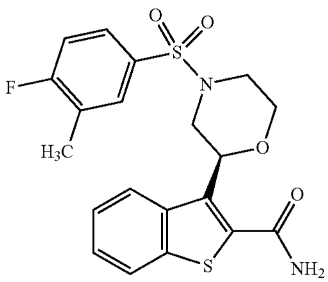 [SMILES: Cc1cc(S(=O)(=O)N2CCO[C@@H](c3c(C(N)=O)sc4ccccc34)C2)ccc1F] | 3-[(S)-4-(4-fluoro-3-methyl-phenyl)sulfonylmorpholin-2-yl]benzothiophene-2-carboxamide | C20 H19 F N2 O4 S2 | + |
| 015 | 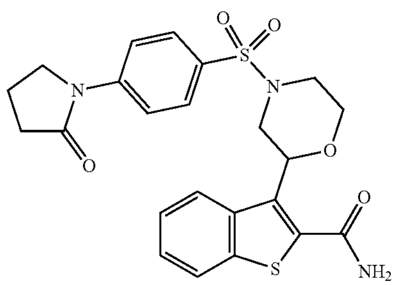 [SMILES: NC(=O)c1sc2ccccc2c1C1CN(S(=O)(=O)c2ccc(N3CCCC3=O)cc2)CCO1] | rac-3-[4-[4-(2-oxopyrrolidin-1-yl)phenyl]sulfonylmorpholin-2-yl]benzothiophene-2-carboxamide | C23 H23 N3 O5 S2 | + |
| 016 | 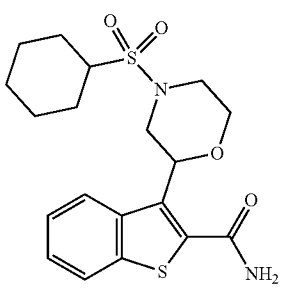 [SMILES: NC(=O)c1sc2ccccc2c1C1CN(S(=O)(=O)C2CCCCC2)CCO1] | rac-3-[4-cyclohexylsulfonylmorpholin-2-yl]benzothiophene-2-carboxamide | C19 H24 N2 O4 S2 | + |
| 017 | 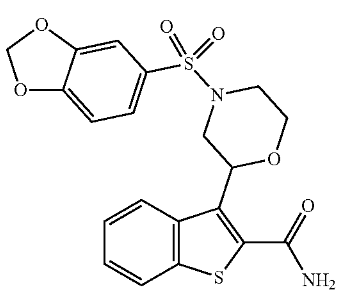 [SMILES: NC(=O)c1sc2ccccc2c1C1CN(S(=O)(=O)c2ccc3c(c2)OCO3)CCO1] | rac-3-[4-(1,3-benzodioxol-5-ylsulfonyl)morpholin-2-yl]benzothiophene-2-carboxamide | C20 H18 N2 O6 S2 | ++ |
| 018 | 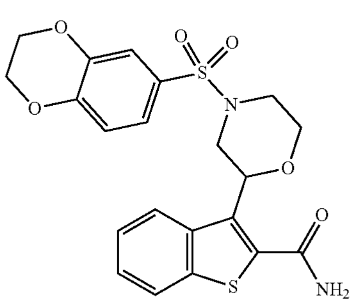 [SMILES: NC(=O)c1sc2ccccc2c1C1CN(S(=O)(=O)c2ccc3c(c2)OCCO3)CCO1] | rac-3-[(4-(2,3-dihydro-1,4-benzodioxin-6-ylsulfonyl)morpholin-2-yl]benzothiophene-2-carboxamide | C21 H20 N2 O6 S2 | +++ |

-continued

| # | Structure | Substance Name | Molecular Formula | Activity |
|---|---|---|---|---|
| 019 | 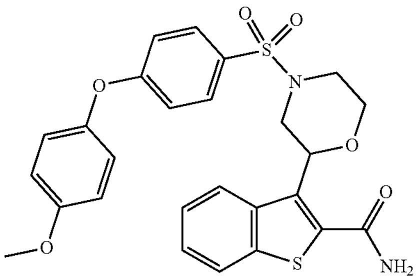 [SMILES: COc1ccc(Oc2ccc(S(=O)(=O)N3CCOC(c4c(C(N)=O)sc5ccccc45)C3)cc2)cc1] | rac-3-[4-[4-(4-methoxyphenoxy)phenyl]sulfonylmorpholin-2-yl]benzothiophene-2-carboxamide | C26 H24 N2 O6 S2 | + |
| 020 | 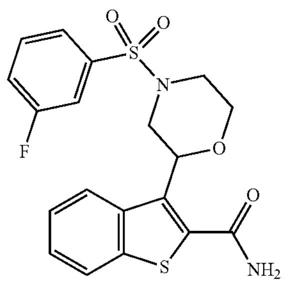 [SMILES: NC(=O)c1sc2ccccc2c1C1CN(S(=O)(=O)c2cccc(F)c2)CCO1] | rac-3-[4-(3-fluorophenyl)sulfonylmorpholin-2-yl]benzothiophene-2-carboxamide | C19 H17 F N2 O4 S2 | ++ |
| 021 | 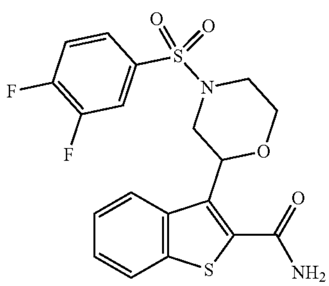 [SMILES: NC(=O)c1sc2ccccc2c1C1CN(S(=O)(=O)c2ccc(F)c(F)c2)CCO1] | rac-3-[4-(3,4-difluorophenyl)sulfonylmorpholin-2-yl]benzothiophene-2-carboxamide | C19 H16 F2 N2 O4 S2 | + |
| 022 | 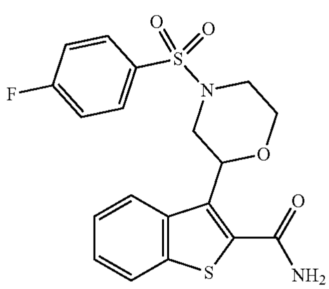 [SMILES: NC(=O)c1sc2ccccc2c1C1CN(S(=O)(=O)c2ccc(F)cc2)CCO1] | rac-3-[4-(4-fluorophenyl)sulfonylmorpholin-2-yl]benzothiophene-2-carboxamide | C19 H17 F N2 O4 S2 | + |
| 023 | 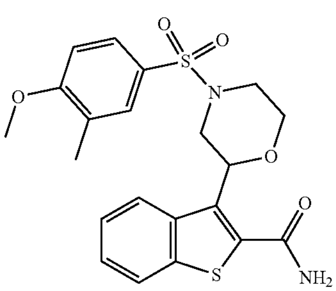 [SMILES: COc1ccc(S(=O)(=O)N2CCOC(c3c(C(N)=O)sc4ccccc34)C2)cc1C] | rac-3-[4-(4-methoxy-3-methyl-phenyl)sulfonylmorpholin-2-yl]benzothiophene-2-carboxamide | C21 H22 N2 O5 S2 | + |

-continued

| # | Structure | Substance Name | Molecular Formula | Activity |
|---|---|---|---|---|
| 024 | 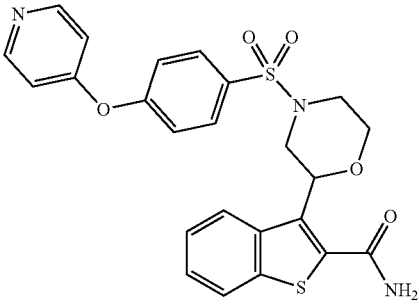 [SMILES: NC(=O)c1sc2ccccc2c1C1CN(S(=O)(=O)c2ccc(Oc3ccncc3)cc2)CCO1] | rac-3-[4-[4-(4-pyridyloxy)phenyl]sulfonylmorpholin-2-yl]benzothiophene-2-carboxamide | C24 H21 N3 O5 S2 | + |
| 025 | 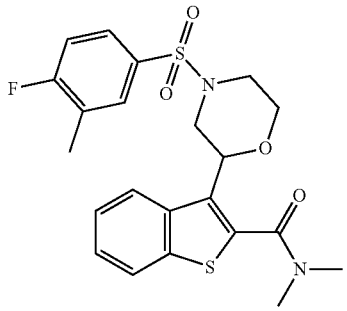 [SMILES: Cc1cc(S(=O)(=O)N2CCOC(c3c(C(=O)N(C)C)sc4ccccc34)C2)ccc1F] | rac-3-[4-(4-fluoro-3-methyl-phenyl)sulfonylmorpholin-2-yl]-N,N-dimethyl-benzothiophene-2-carboxamide | C22 H23 F N2 O4 S2 | + |
| 026 | 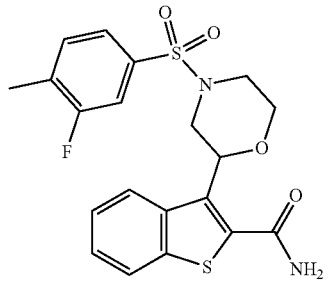 [SMILES: Cc1ccc(S(=O)(=O)N2CCOC(c3c(C(N)=O)sc4ccccc34)C2)cc1F] | rac-3-[4-(3-fluoro-4-methyl-phenyl)sulfonylmorpholin-2-yl]benzothiophene-2-carboxamide | C20 H19 F N2 O4 S2 | +++ |
| 027 | 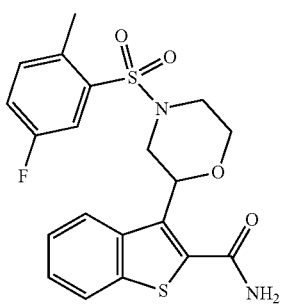 [SMILES: Cc1ccc(F)cc1S(=O)(=O)N1CCOC(c2c(C(N)=O)sc3ccccc23)C1] | rac-3-[4-(5-fluoro-2-methyl-phenyl)sulfonylmorpholin-2-yl]benzothiophene-2-carboxamide | C20 H19 F N2 O4 S2 | + |
| 028 | 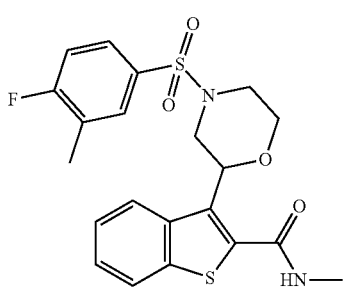 [SMILES: CNC(=O)c1sc2ccccc2c1C1CN(S(=O)(=O)c2ccc(F)c(C)c2)CCO1] | rac-3-[4-(4-fluoro-3-methyl-phenyl)sulfonylmorpholin-2-yl]-N-methyl-benzothiophene-2-carboxamide | C21 H21 F N2 O4 S2 | + |

-continued

| # | Structure | Substance Name | Molecular Formula | Activity |
|---|---|---|---|---|
| 029 | 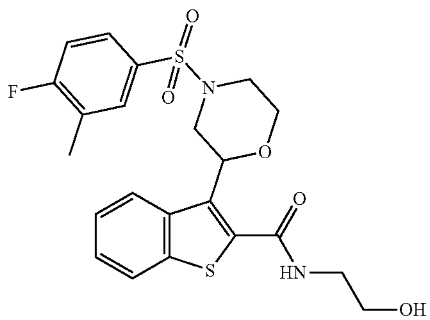 [SMILES: Cc1cc(S(=O)(=O)N2CCOC(c3c(C(=O)NCCO)sc4ccccc34)C2)ccc1F] | rac-3-[4-(4-fluoro-3-methyl-phenyl)sulfonylmorpholin-2-yl]-N-(2-hydroxyethyl)benzothiophene-2-carboxamide | C22 H23 F N2 O5 S2 | + |
| 030 | 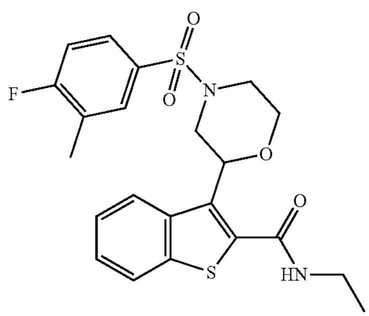 [SMILES: CCNC(=O)c1sc2ccccc2c1C1CN(S(=O)(=O)c2ccc(F)c(C)c2)CCO1] | rac-N-ethyl-3-[4-(4-fluoro-3-methyl-phenyl)sulfonylmorpholin-2-yl]benzothiophene-2-carboxamide | C22 H23 F N2 O4 S2 | + |
| 031 | 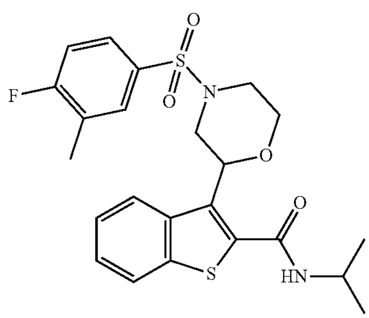 [SMILES: Cc1cc(S(=O)(=O)N2CCOC(c3c(C(=O)NC(C)C)sc4ccccc34)C2)ccc1F] | rac-3-[4-(4-fluoro-3-methyl-phenyl)sulfonylmorpholin-2-yl]-N-isopropyl-benzothiophene-2-carboxamide | C23 H25 F N2 O4 S2 | + |
| 032 | 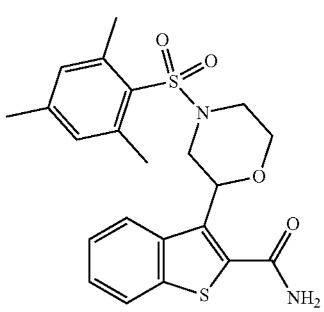 [SMILES: Cc1cc(C)c(S(=O)(=O)N2CCOC(c3c(C(N)=O)sc4ccccc34)C2)c(C)c1] | rac-3-[4-(2,4,6-trimethylphenyl)sulfonylmorpholin-2-yl]benzothiophene-2-carboxamide | C22 H24 N2 O4 S2 | + |
| 033 | 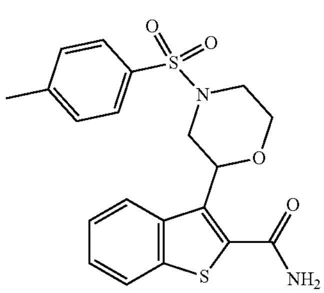 [SMILES: Cc1ccc(S(=O)(=O)N2CCOC(c3c(C(N)=O)sc4ccccc34)C2)cc1] | rac-3-[4-(p-tolylsulfonyl)morpholin-2-yl]benzothiophene-2-carboxamide | C20 H20 N2 O4 S2 | +++ |

| # | Structure | Substance Name | Molecular Formula | Activity |
|---|---|---|---|---|
| 034 | 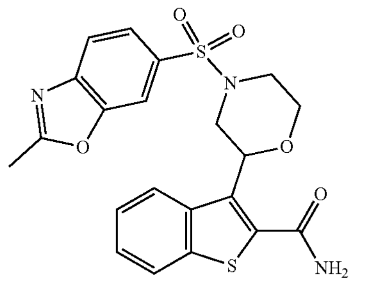 [SMILES: Cc1nc2ccc(S(=O)(=O)N3CCOC(c4c(C(N)=O)sc5ccccc45)C3)cc2o1] | rac-3-[4-[(2-methyl-1,3-benzoxazol-6-yl)sulfonyl]morpholin-2-yl]benzothiophene-2-carboxamide | C21 H19 N3 O5 S2 | +++ |
| 035 | 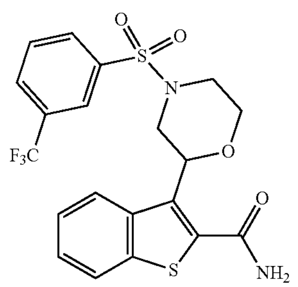 [SMILES: NC(=O)c1sc2ccccc2c1C1CN(S(=O)(=O)c2cccc(C(F)(F)F)c2)CCO1] | rac-3-[4-[3-(trifluoromethyl)phenyl]sulfonylmorpholin-2-yl]benzothiophene-2-carboxamide | C20 H17 F3 N2 O4 S2 | +++ |
| 036 | 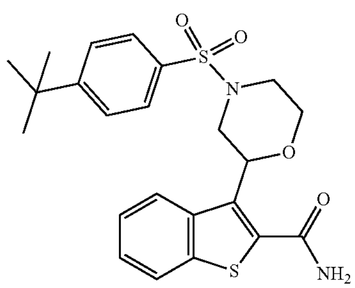 [SMILES: CC(C)(C)c1ccc(S(=O)(=O)N2CCOC(c3c(C(N)=O)sc4ccccc34)C2)cc1] | rac-3-[4-(4-tert-butylphenyl)sulfonylmorpholin-2-yl]benzothiophene-2-carboxamide | C23 H26 N2 O4 S2 | +++ |
| 037 | 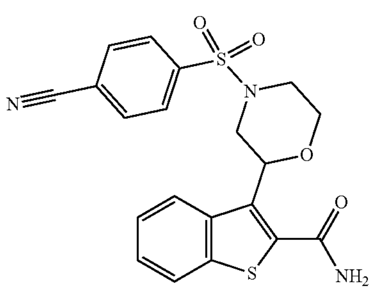 [SMILES: N#Cc1ccc(S(=O)(=O)N2CCOC(c3c(C(N)=O)sc4ccccc34)C2)cc1] | rac-3-[4-(4-cyanophenyl)sulfonylmorpholin-2-yl]benzothiophene-2-carboxamide | C20 H17 N3 O4 S2 | + |
| 038 | 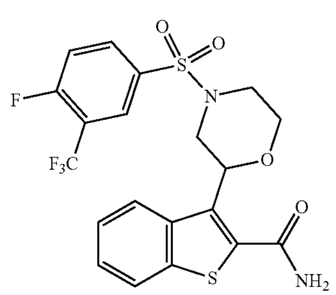 [SMILES: NC(=O)c1sc2ccccc2c1C1CN(S(=O)(=O)c2ccc(F)c(C(F)(F)F)c2)CCO1] | rac-3-[4-[4-fluoro-3-(trifluoromethyl)phenyl]sulfonylmorpholin-2-yl]benzothiophene-2-carboxamide | C20 H16 F4 N2 O4 S2 | + |

| # | Structure | Substance Name | Molecular Formula | Activity |
| --- | --- | --- | --- | --- |
| 039 | 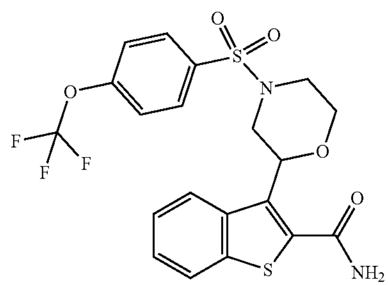 [SMILES: NC(=O)c1sc2ccccc2c1C1CN(S(=O)(=O)c2ccc(OC(F)(F)F)cc2)CCO1] | rac-3-[4-[4-(trifluoromethoxy)phenyl]sulfonylmorpholin-2-yl]benzothiophene-2-carboxamide | C20 H17 F3 N2 O5 S2 | +++ |
| 040 | 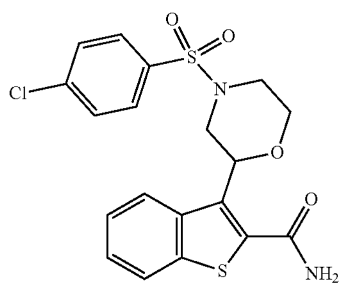 [SMILES: NC(=O)c1sc2ccccc2c1C1CN(S(=O)(=O)c2ccc(Cl)cc2)CCO1] | rac-3-[4-(4-chlorophenyl)sulfonylmorpholin-2-yl]benzothiophene-2-carboxamide | C19 H17 Cl N2 O4 S2 | ++ |
| 041 | 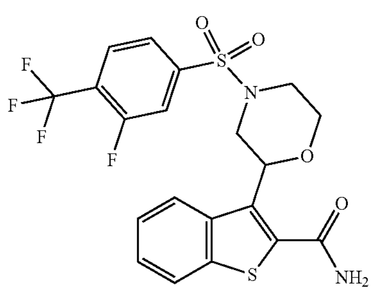 [SMILES: NC(=O)c1sc2ccccc2c1C1CN(S(=O)(=O)c2ccc(C(F)(F)F)c(F)c2)CCO1] | rac-3-[4-[3-fluoro-4-(trifluoromethyl)phenyl]sulfonylmorpholin-2-yl]benzothiophene-2-carboxamide | C20 H16 F4 N2 O4 S2 | +++ |
| 042 | 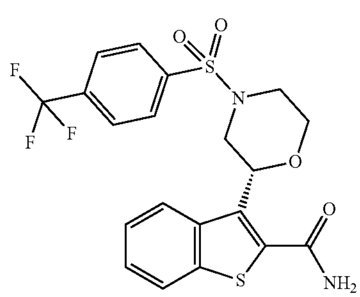 [SMILES: NC(=O)c1sc2ccccc2c1[C@@H]1CN(S(=O)(=O)c2ccc(C(F)(F)F)cc2)CCO1] | 3-[(R)-4-[4-(trifluoromethyl)phenyl]sulfonylmorpholin-2-yl]benzothiophene-2-carboxamide | C20 H17 F3 N2 O4 S2 | + |
| 043 | 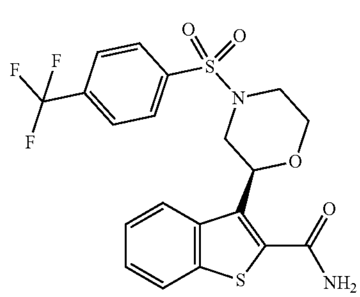 [SMILES: NC(=O)c1sc2ccccc2c1[C@H]1CN(S(=O)(=O)c2ccc(C(F)(F)F)cc2)CCO1] | 3-[(S)-4-[4-(trifluoromethyl)phenyl]sulfonylmorpholin-2-yl]benzothiophene-2-carboxamide | C20 H17 F3 N2 O4 S2 | +++ |

| # | Structure | Substance Name | Molecular Formula | Activity |
|---|---|---|---|---|
| 044 | 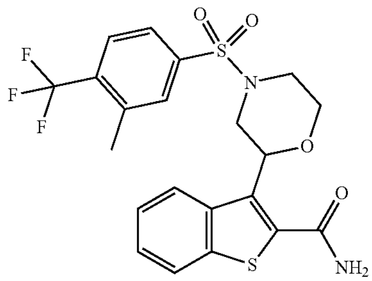 [SMILES: Cc1cc(S(=O)(=O)N2CCOC(c3c(C(N)=O)sc4ccccc34)C2)ccc1C(F)(F)F] | rac-3-[4-[3-methyl-4-(trifluoromethyl)phenyl]sulfonylmorpholin-2-yl]benzothiophene-2-carboxamide | C21 H19 F3 N2 O4 S2 | ++ |
| 045 | 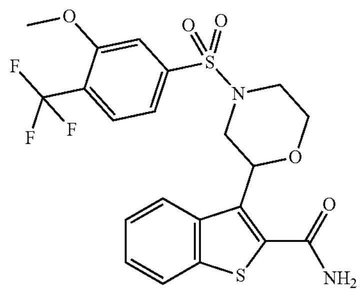 [SMILES: COc1cc(S(=O)(=O)N2CCOC(c3c(C(N)=O)sc4ccccc34)C2)ccc1C(F)(F)F] | rac-3-[4-[3-methoxy-4-(trifluoromethyl)phenyl]sulfonylmorpholin-2-yl]benzothiophene-2-carboxamide | C21 H19 F3 N2 O5 S2 | ++ |
| 046 | 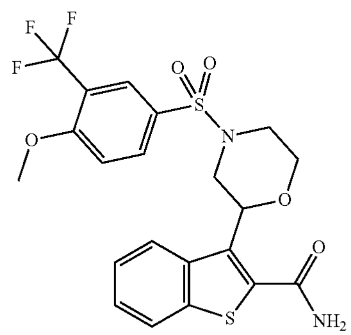 [SMILES: COc1ccc(S(=O)(=O)N2CCOC(c3c(C(N)=O)sc4ccccc34)C2)cc1C(F)(F)F] | rac-3-[4-[4-methoxy-3-(trifluoromethyl)phenyl]sulfonylmorpholin-2-yl]benzothiophene-2-carboxamide | C21 H19 F3 N2 O5 S2 | +++ |
| 047 | 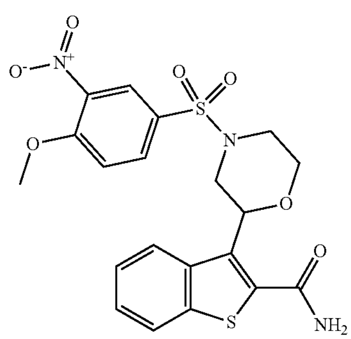 [SMILES: COc1ccc(S(=O)(=O)N2CCOC(c3c(C(N)=O)sc4ccccc34)C2)cc1[N+](=O)[O-]] | rac-3-[4-(4-methoxy-3-nitro-phenyl)sulfonylmorpholin-2-yl]benzothiophene-2-carboxamide | C20 H19 N3 O7 S2 | + |
| 048 | 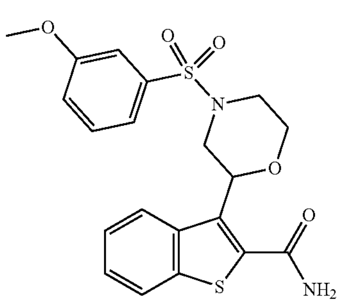 [SMILES: COc1cccc(S(=O)(=O)N2CCOC(c3c(C(N)=O)sc4ccccc34)C2)c1] | rac-3-[4-(3-methoxyphenyl)sulfonylmorpholin-2-yl]benzothiophene-2-carboxamide | C20 H20 N2 O5 S2 | + |

-continued

| # | Structure | Substance Name | Molecular Formula | Activity |
|---|---|---|---|---|
| 049 | 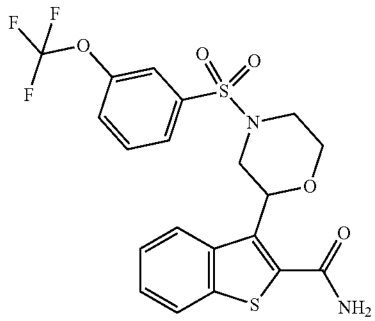 [SMILES: NC(=O)c1sc2ccccc2c1C1CN(S(=O)(=O)c2cccc(OC(F)(F)F)c2)CCO1] | rac-3-[4-[3-(trifluoromethoxy)phenyl]sulfonylmorpholin-2-yl]benzothiophene-2-carboxamide | C20 H17 F3 N2 O5 S2 | + |
| 050 | 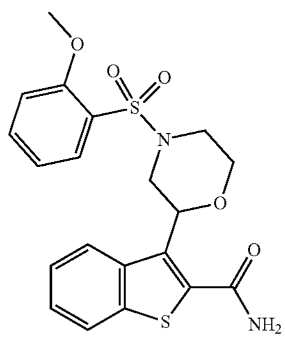 [SMILES: COc1ccccc1S(=O)(=O)N1CCOC(c2c(C(N)=O)sc3ccccc23)C1] | rac-3-[4-(2-methoxyphenyl)sulfonylmorpholin-2-yl]benzothiophene-2-carboxamide | C20 H20 N2 O5 S2 | + |
| 051 | 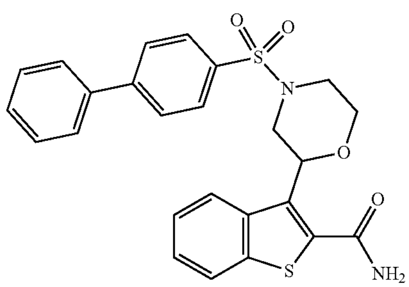 [SMILES: NC(=O)c1sc2ccccc2c1C1CN(S(=O)(=O)c2ccc(-c3ccccc3)cc2)CCO1] | rac-3-[4-(4-phenylphenyl)sulfonylmorpholin-2-yl]benzothiophene-2-carboxamide | C25 H22 N2 O4 S2 | +++ |
| 052 | 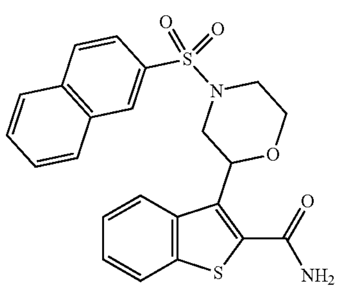 [SMILES: NC(=O)c1sc2ccccc2c1C1CN(S(=O)(=O)c2ccc3ccccc3c2)CCO1] | rac-3-[4-(2-naphthylsulfonyl)morpholin-2-yl]benzothiophene-2-carboxamide | C23 H20 N2 O4 S2 | + |
| 053 | 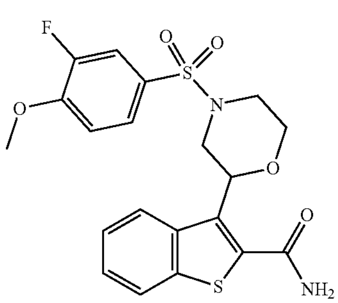 [SMILES: COc1ccc(S(=O)(=O)N2CCOC(c3c(C(N)=O)sc4ccccc34)C2)cc1F] | rac-3-[4-(3-fluoro-4-methoxy-phenyl)sulfonylmorpholin-2-yl]benzothiophene-2-carboxamide | C20 H19 F N2 O5 S2 | + |

-continued

| # | Structure | Substance Name | Molecular Formula | Activity |
|---|---|---|---|---|
| 054 | 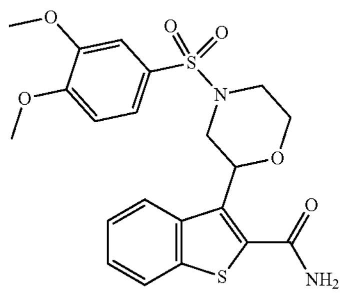 [SMILES: COc1ccc(S(=O)(=O)N2CCOC(c3c(C(N)=O)sc4ccccc34)C2)cc1OC] | rac-3-[4-(3,4-dimethoxyphenyl)sulfonylmorpholin-2-yl]benzothiophene-2-carboxamide | C21 H22 N2 O6 S2 | + |
| 055 | 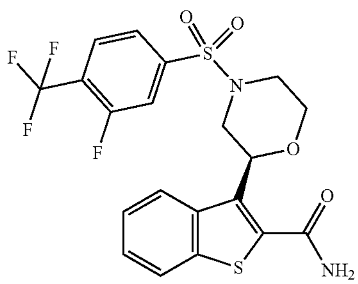 [SMILES: NC(=O)c1sc2ccccc2c1[C@H]1CN(S(=O)(=O)c2ccc(C(F)(F)F)c(F)c2)CCO1] | 3-[(S)-4-[3-fluoro-4-(trifluoromethyl)phenyl]sulfonylmorpholin-2-yl]benzothiophene-2-carboxamide | C20 H16 F4 N2 O4 S2 | + |
| 056 | 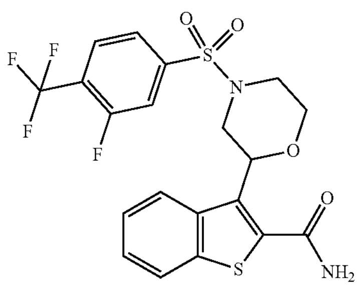 [SMILES: NC(=O)c1sc2ccccc2c1C1CN(S(=O)(=O)c2ccc(C(F)(F)F)c(F)c2)CCO1] | 3-[(R)-4-[3-fluoro-4-(trifluoromethyl)phenyl]sulfonylmorpholin-2-yl]benzothiophene-2-carboxamide | C20 H16 F4 N2 O4 S2 | +++ |
| 057 | 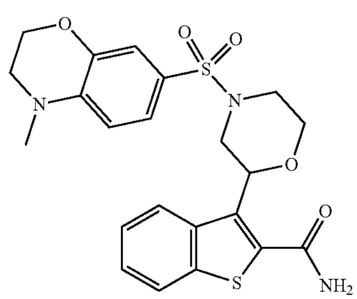 [SMILES: CN1CCOc2cc(S(=O)(=O)N3CCOC(c4c(C(N)=O)sc5ccccc45)C3)ccc21] | rac-3-[4-[(4-methyl-2,3-dihydro-1,4-benzoxazin-7-yl)sulfonyl]morpholin-2-yl]benzothiophene-2-carboxamide | C22 H23 N3 O5 S2 | +++ |
| 058 | 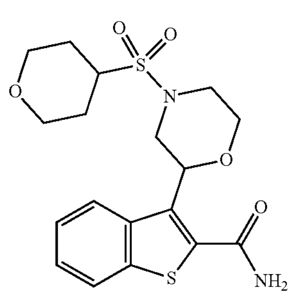 [SMILES: NC(=O)c1sc2ccccc2c1C1CN(S(=O)(=O)C2CCOCC2)CCO1] | rac-3-[4-tetrahydropyran-4-ylsulfonylmorpholin-2-yl]benzothiophene-2-carboxamide | C18 H22 N2 O5 S2 | + |

-continued

| # | Structure | Substance Name | Molecular Formula | Activity |
|---|---|---|---|---|
| 059 | 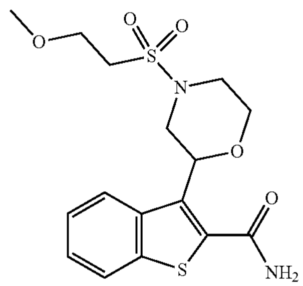 [SMILES: COCCS(=O)(=O)N1CCOC(c2c(C(N)=O)sc3ccccc23)C1] | rac-3-[4-(2-methoxyethylsulfonyl)morpholin-2-yl]benzothiophene-2-carboxamide | C16 H20 N2 O5 S2 | + |
| 060 | 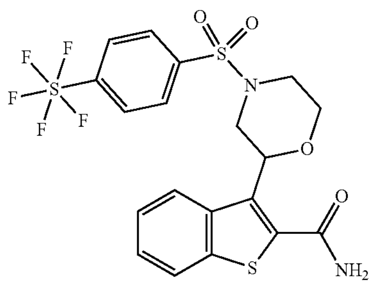 [SMILES: NC(=O)c1sc2ccccc2c1C1CN(S(=O)(=O)c2ccc(S(F)(F)(F)(F)F)cc2)CCO1] | rac-3-[4-[4-(pentafluoro-lambda6-sulfanyl)phenyl]sulfonylmorpholin-2-yl]benzothiophene-2-carboxamide | C19 H17 F5 N2 O4 S3 | ++ |
| 061 | 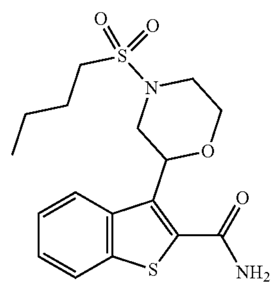 [SMILES: CCCCS(=O)(=O)N1CCOC(c2c(C(N)=O)sc3ccccc23)C1] | rac-3-[4-butylsulfonylmorpholin-2-yl]benzothiophene-2-carboxamide | C17 H22 N2 O4 S2 | + |
| 062 | 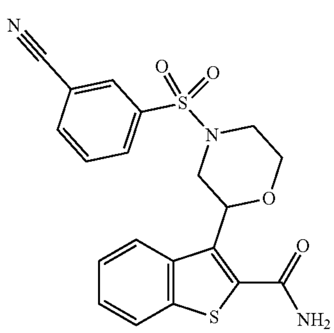 [SMILES: N#Cc1cccc(S(=O)(=O)N2CCOC(c3c(C(N)=O)sc4ccccc34)C2)c1] | rac-3-[4-(3-cyanophenyl)sulfonylmorpholin-2-yl]benzothiophene-2-carboxamide | C20 H17 N3 O4 S2 | + |
| 063 | 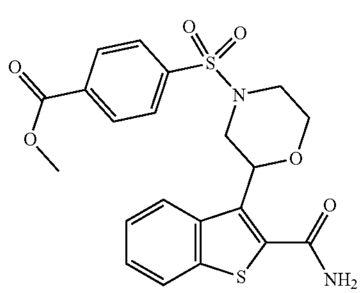 [SMILES: COC(=O)c1ccc(S(=O)(=O)N2CCOC(c3c(C(N)=O)sc4ccccc34)C2)cc1] | rac-methyl 4-[2-(2-carbamoylbenzothiophen-3-yl)morpholin-4-yl]sulfonylbenzoate | C21 H20 N2 O6 S2 | + |

-continued

| # | Structure | Substance Name | Molecular Formula | Activity |
|---|---|---|---|---|
| 064 | 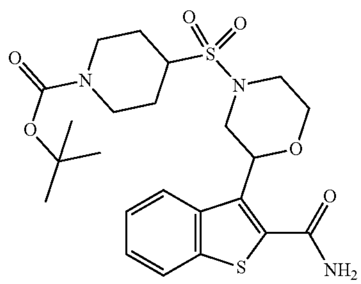 [SMILES: CC(C)(C)OC(=O)N1CCC(S(=O)(=O)N2CCOC(c3c(C(N)=O)sc4ccccc34)C2)CC1] | rac-tert-butyl 4-[2-(2-carbamoylbenzothiophen-3-yl)morpholin-4-yl]sulfonylpiperidine-1-carboxylate | C23 H31 N3 O6 S2 | + |
| 065 | 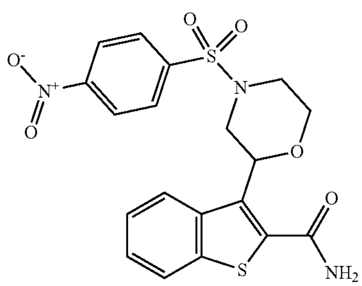 [SMILES: NC(=O)c1sc2ccccc2c1C1CN(S(=O)(=O)c2ccc([N+](=O)[O-])cc2)CCO1] | rac-3-[4-(4-nitrophenyl)sulfonylmorpholin-2-yl]benzothiophene-2-carboxamide | C19 H17 N3 O6 S2 | + |
| 066 | 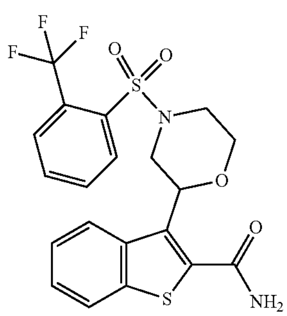 [SMILES: NC(=O)c1sc2ccccc2c1C1CN(S(=O)(=O)c2ccccc2C(F)(F)F)CCO1] | rac-3-[4-[2-(trifluoromethyl)phenyl]sulfonylmorpholin-2-yl]benzothiophene-2-carboxamide | C20 H17 F3 N2 O4 S2 | + |
| 067 | 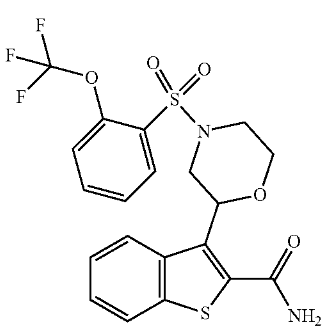 [SMILES: NC(=O)c1sc2ccccc2c1C1CN(S(=O)(=O)c2ccccc2OC(F)(F)F)CCO1] | rac-3-[4-[2-(trifluoromethoxy)phenyl]sulfonylmorpholin-2-yl]benzothiophene-2-carboxamide | C20 H17 F3 N2 O5 S2 | + |
| 068 | 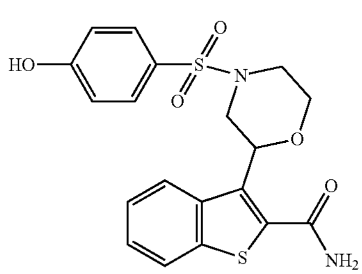 [SMILES: NC(=O)c1sc2ccccc2c1C1CN(S(=O)(=O)c2ccc(O)cc2)CCO1] | rac-3-[4-(4-hydroxyphenyl)sulfonylmorpholin-2-yl]benzothiophene-2-carboxamide | C19 H18 N2 O5 S2 | + |

| # | Structure | Substance Name | Molecular Formula | Activity |
|---|---|---|---|---|
| 069 | 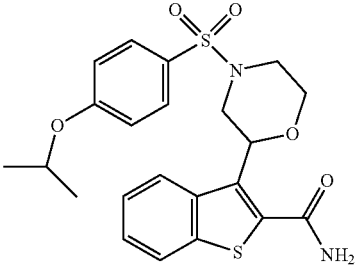 [SMILES: CC(C)Oc1ccc(S(=O)(=O)N2CCOC(c3c(C(N)=O)sc4ccccc34)C2)cc1] | rac-3-[4-(4-isopropoxyphenyl)sulfonylmorpholin-2-yl]benzothiophene-2-carboxamide | C22 H24 N2 O5 S2 | +++ |
| 070 | 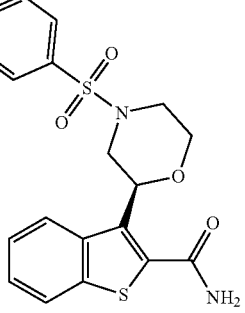 | 3-[(S)-4-[(2-methyl-1,3-benzoxazol-6-yl)sulfonyl]morpholin-2-yl]benzothiophene-2-carboxamide | C21 H19 N3 O5 S2 | + |
| 071 | 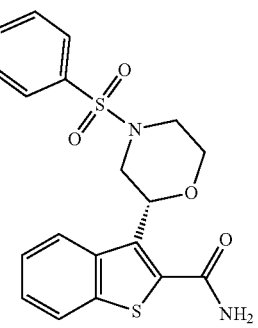 | 3-[(R)-4-[(2-methyl-1,3-benzoxazol-6-yl)sulfonyl]morpholin-2-yl]benzothiophene-2-carboxamide | C21 H19 N3 O5 S2 | +++ |
| 072 | 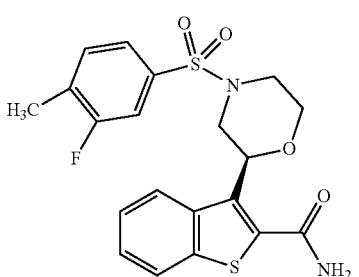 | 3-[(S)-4-(3-fluoro-4-methyl-phenyl)sulfonylmorpholin-2-yl]benzothiophene-2-carboxamide | C20 H19 F N2 O4 S2 | + |
| 073 | 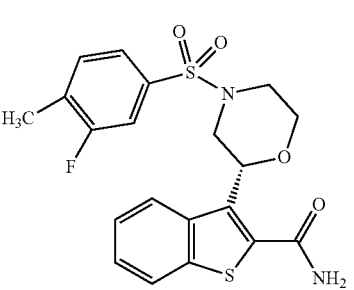 [SMILES: Cc1ccc(S(=O)(=O)N2CCO[C@H](c3c(C(N)=O)sc4ccccc34)C2)cc1F] | 3-[(R)-4-(3-fluoro-4-methyl-phenyl)sulfonylmorpholin-2-yl]benzothiophene-2-carboxamide | C20 H19 F N2 O4 S2 | +++ |

| # | Structure | Substance Name | Molecular Formula | Activity |
|---|---|---|---|---|
| 074 | 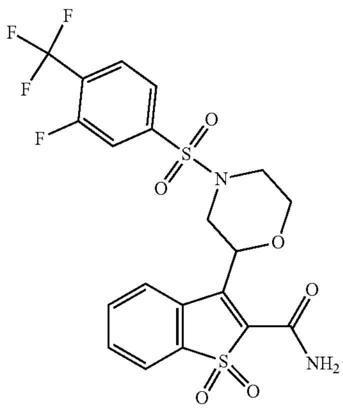 [SMILES: NC(=O)C1=C(C2CN(S(=O)(=O)c3ccc(C(F)(F)F)c(F)c3)CCO2)c2ccccc2S1(=O)=O] | rac-1,1-dioxo-3-[4-[3-fluoro-4-(trifluoromethyl)phenyl]sulfonylmorpholin-2-yl]benzothiophene-2-carboxamide | C20 H16 F4 N2 O6 S2 | +++ |
| 075 | 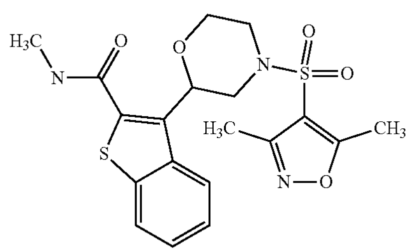 | 3-[4-(3,5-dimethyl-isoxazole-4-sulfonyl)-morpholin-2-yl]-benzo[b]thiophene-2-carboxylic acid methylamide | C19 H21 N3 O5 S2 | + |
| 076 | 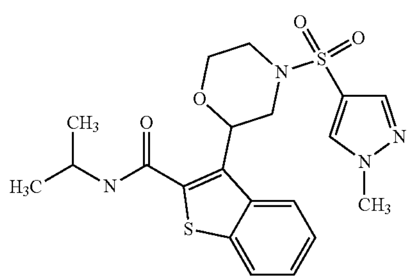 [SMILES: CC(C)NC(=O)c1sc2ccccc2c1C1CN(S(=O)(=O)c2cnn(C)c2)CCO1] | 3-[4-(1-methyl-1H-pyrazole-4-sulfonyl)-morpholin-2-yl]-benzo[b]thiophene-2-carboxylic acid isopropylamide | C20 H24 N4 O4 S2 | + |
| 078 | 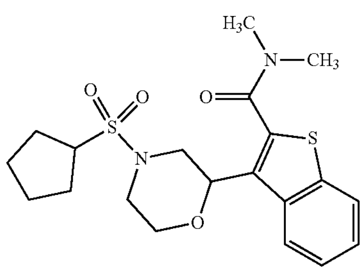 [SMILES: CN(C)C(=O)c1sc2ccccc2c1C1CN(S(=O)(=O)C2CCCC2)CCO1] | 3-[4-(cyclopentylsulfonyl)-2-morpholinyl]-N,N-dimethyl-1-benzothiophene-2-carboxamide | C20 H26 N2 O4 S2 | + |
| 079 | 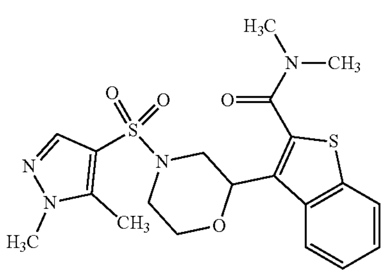 [SMILES: Cc1c(S(=O)(=O)N2CCOC(c3c(C(=O)N(C)C)sc4ccccc34)C2)cnn1C] | 3-{4-[(1,5-dimethyl-1H-pyrazol-4-yl)sulfonyl]-2-morpholinyl}-N,N-dimethyl-1-benzothiophene-2-carboxamide | C20 H24 N4 O4 S2 | + |

-continued

| # | Structure | Substance Name | Molecular Formula | Activity |
|---|-----------|----------------|-------------------|----------|
| 080 | 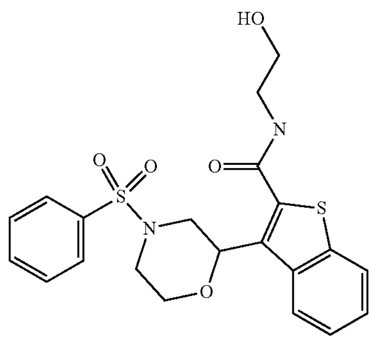 [SMILES: O=C(NCCO)c1sc2ccccc2c1C1CN(S(=O)(=O)c2ccccc2)CCO1] | N-(2-hydroxyethyl)-3-[4-(phenylsulfonyl)-2-morpholinyl]-1-benzothiophene-2-carboxamide | C21 H22 N2 O5 S2 | + |
| 081 | 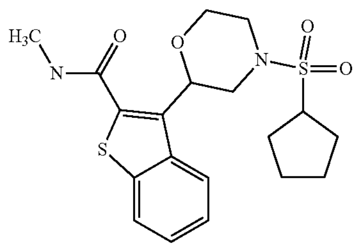 [SMILES: CNC(=O)c1sc2ccccc2c1C1CN(S(=O)(=O)C2CCCC2)CCO1] | 3-(4-cyclopentanesulfonyl-morpholin-2-yl)-benzo[b]thiophene-2-carboxylic acid methylamide | C19 H24 N2 O4 S2 | + |
| 082 | 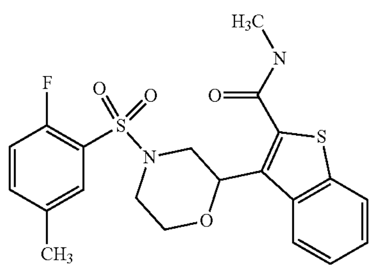 [SMILES: CNC(=O)c1sc2ccccc2c1C1CN(S(=O)(=O)c2cc(C)ccc2F)CCO1] | 3-{4-[(2-fluoro-5-methylphenyl)sulfonyl]-2-morpholinyl}-N-methyl-1-benzothiophene-2-carboxamide | C21 H21 F N2 O4 S2 | |
| 083 | 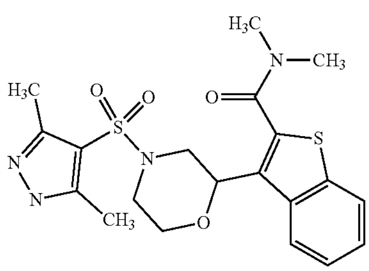 [SMILES: Cc1n[nH]c(C)c1S(=O)(=O)N1CCOC(c2c(C(=O)N(C)C)sc3ccccc23)C1] | 3-{4-[(3,5-dimethyl-1H-pyrazol-4-yl)sulfonyl]-2-morpholinyl}-N,N-dimethyl-1-benzothiophene-2-carboxamide | C20 H24 N4 O4 S2 | + |

Transepithelial Electrical Conductance (TEEC)

FRT cells expressing F508del-CFTR were plated on HTS Transwell-24 well permeable supports (Code 3379, Corning Life Sciences) at a density of 200,000 cells/well. After six days, cells were incubated for 24 hrs with test correctors, vehicle, or VX-809. Compounds were dissolved in both basolateral (800 μL) and apical (300 μL) culture medium. After treatment, the culture medium was removed and replaced on both sides with a saline solution containing (in mM): 130 NaCl, 2.7 KCl, 1.5 KH$_2$PO$_4$, 1 CaCl$_2$, 0.5 MgCl$_2$, 10 glucose, 10 Na-Hepes (pH 7.4). The basolateral and apical side received 800 μL and 100 μL, respectively. The 24-well tray with cells was placed on a block heater (SBH 130D, Stuart) to keep the temperature at 37° C. during the entire experiment. After 10 min, the basal transepithelial electrical resistance (TEER) across each layer of FRT cells was measured with a STX100C electrode pair connected to an EVOM2 voltohmeter (World Precision Instruments). To stimulate F508del-CFTR, each well received (apical side) 50 μL of saline solution containing 60 μM forskolin and 150 μM genistein (final concentrations: 20 μM forskolin, 50 μM genistein). Forskolin was also pipetted in the basolateral medium to obtain the 20 μM concentration. After 10 min TEER was measured again in each well. To block F508del-CFTR function, the inhibitor PPQ-102 was used at the final concentration of 30 μM. To achieve the desired concentration, 75 μL of the apical solution in each well was replaced with an equal volume of saline solution containing 20 μM forskolin, 50 μM genistein, and 60 μM PPQ-102. After further 10 min, the transepithelial electrical resistance was measured. All values of TEER were converted to transepithelial electrical conductance (TEEC) using the formula TEEC=1/TEER. The parameter to indicate activity of F508del-CFTR in each well (ATEEC) was calculated from the difference in TEEC measured after maximal stimulation of F508del-CFTR with forskolin and genistein and after block with PPQ-102.

Corrector activities obtained on selected compounds tested at 5.0 µM (expressed as ΔTEEC values) are illustrated in Table 2, wherein+: ΔTEEC<2000 µS; ++: 2000 µS <ΔTEEC<3000ρS; +++: ΔTEEC>3000 µS.

TABLE 2

| # | Substance Name | activity |
|---|---|---|
| 001 | rac-3-[4-(4-fluoro-3-methyl-benzenesulfonyl)-morpholin-2-yl]-benzo[b]thiophene-2-carboxylic acid amide | ++ |
| 011 | rac-3-[4-[4-(trifluoromethyl)phenyl] sulfonylmorpholin-2-yl]benzothiophene-2-carboxamide | ++ |
| 034 | rac-3-[4-[(2-methyl-1,3-benzoxazol-6-yl)sulfonyl]morpholin-2-yl] benzothiophene-2-carboxamide | ++ |
| 039 | rac-3-[4-[4-(trifluoromethoxy)phenyl] sulfonylmorpholin-2-yl]benzothiophene-2-carboxamide | ++ |
| 041 | rac-3-[4-[3-fluoro-4-(trifluoromethyl) phenyl]sulfonylmorpholin-2-yl]benzothiophene-2-carboxamide | +++ |
| 042 | 3-[(R) or (S)-4-[4 -(trifluoromethyl)phenyl]sulfonylmorpholin-2-yl]benzothiophene-2-carboxamide | + |
| 043 | 3-[(S) or (R)-4-[4-(trifluoromethyl) phenyl]sulfonylmorpholin-2-yl] benzothiophene-2-carboxamide | +++ |

Short-Circuit Current Recordings on Human Bronchial Epithelial Cells

Human bronchial epithelial (HBE) cells obtained from CF patients (F508del/F508del genotype) were plated on Snapwell inserts (Code 3801, Corning Life Sciences) at a density of 500,000 cells per insert. Cells were cultured for two weeks in a differentiating medium whose compositions has been previously described (Scudieri et al., J Physiol 590: 6141-6155, 2012). For the first week, the medium was kept on both apical and basolateral sides of inserts (submerged condition). For the second week, the apical medium was removed (air-liquid condition, ALC). To test the activity of correctors, cells were treated for 24 hrs with compounds dissolved in the basolateral medium. After treatment, Snapwell inserts carrying differentiated bronchial epithelia were mounted in a vertical chamber resembling an Ussing system with internal fluid circulation. Both apical and basolateral hemichambers were filled with 5 mL of a Krebs bicarbonate solution containing (in mM): 126 NaCl, 0.38 $KH_2PO_4$, 2.13 $K_2HPO_4$, 1 $MgSO_4$, 1 $CaCl_2$, 24 $NaHCO_3$, and 10 glucose. Both sides were continuously bubbled with a gas mixture containing 5% $CO_2$-95% air and the temperature of the solution was kept at 37° C. The transepithelial voltage was short-circuited with a voltage-clamp (DVC-1000, World Precision Instruments) connected to the apical and basolateral chambers via Ag/AgCl electrodes and agar bridges (1 M KCl in 1% agar). The offset between voltage electrodes and the fluid resistance were canceled before experiments. The short-circuit current was recorded with a PowerLab 4/25 (ADInstruments) analogical to digital converter connected to a Macintosh computer. During recordings, cells were sequentially treated with: amiloride (10 µM, apical side) to block $Na^+$ absorption through ENaC channel; CPT-cAMP (100 µM, apical and basolateral side) plus VX-770 (1 µM, apical side) to stimulate F508del-CFTR activity; CFTRinh-172 (10 µM, apical side) to fully inhibit F508del-CFTR. The difference between the current measured with CPT-cAMP plus potentiator and the current remaining after CFTRinh-172 treatment ($\Delta I_{CFTR}$) was taken as the parameter reflecting F508del-CFTR expression in the apical membrane.

Activities of selected compounds on HBE cells (expressed as $\Delta I_{CFTR}$) are illustrated in Table 3 wherein+: $\Delta I_{CFTR}$<2.0 µA; ++: 2.0 µA<$\Delta I_{CFTR}$<3.0 µA; +++: $\Delta I_{CFTR}$ >3.0 µA.

TABLE 3

| # | Substance Name | activity |
|---|---|---|
| 001 | rac-3-[4-(4-fluoro-3-methyl-benzenesulfonyl)-morpholin-2-yl]-benzo[b]thiophene-2-carboxylic acid amide | + |
| 011 | rac-3-[4-[4-(trifluoromethyl)phenyl] sulfonylmorpholin-2-yl]benzothiophene-2-carboxamide | +++ |
| 013 | 3-[(R)or (S)-4-(4-fluoro-3-methyl-phenyl) sulfonylmorpholin-2-yl]benzothiophene-2-carboxamide | ++ |
| 018 | rac-3-[(4-(2,3-dihydro-1,4-benzodioxin-6-ylsulfonyl)morpholin-2-yl]benzothiophene-2-carboxamide | ++ |
| 034 | rac-3-[4-[(2-methyl-1,3-benzoxazol-6-yl)sulfonyl]morpholin-2-yl]benzothiophene-2-carboxamide | +++ |
| 041 | rac-3-[4-[3-fluoro-4-(trifluoromethyl)phenyl] sulfonylmorpholin-2-yl]benzothiophene-2-carboxamide | ++ |
| 044 | rac-3-[4-[3-methyl-4-(trifluoromethyl)phenyl] sulfonylmorpholin-2-yl]benzothiophene-2-carboxamide | ++ |
| 071 | 3-[(R) or (S)-4-[(2-methyl-1,3-benzoxazol-6-yl)sulfonyl]morpholin-2-yl]benzothiophene-2-carboxamide | +++ |

The invention claimed is:
1. A compound of Formula (Ia):

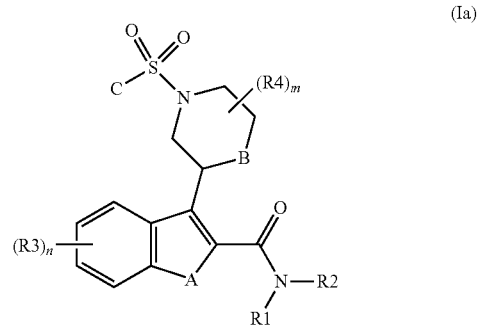

or pharmaceutically acceptable salts, hydrates, solvates, clathrates, polymorphs, stereoisomers thereof wherein:
R1 and R2 are independently selected from the group consisting of hydrogen, $C_{1-4}$alkyl, hydroxy$C_{1-4}$alkyl, and $C_{1-4}$alkyl-O—$C_{1-4}$alkyl;
R3 is selected from the group consisting of hydrogen, $C_{1-6}$alkyl, halo$C_{1-6}$alkyl, OH, O—$C_{1-6}$alkyl, $C_{1-6}$alkyl-O—$C_{1-6}$alkyl, CN, $NO_2$ and halogen;
R4 is independently selected from the group consisting of hydrogen, $C_{1-6}$alkyl, halo$C_{1-6}$ alkyl and halogen;
A is selected from the group consisting of S, SO, and $SO_2$;
B is selected from the group consisting of $CR^{iv}R^v$, O, and $NR^{ii}$;
C is selected from the group consisting of $C_{1-6}$alkyl, halo$C_{1-6}$alkyl, $C_{3-6}$cycloalkyl optionally substituted with one or more R5, $C_{3-6}$heterocycloalkyl optionally substituted with one or more R5, aryl optionally substituted with one or more R5, heteroaryl optionally substituted with one or more R5, $C_{1-6}$alkyl-O—$C_{1-6}$alkyl, $C_{1-6}$alkyl-O-aryl, $C_{1-6}$alkyl-O-heteroaryl, $C_{1-6}$alkyl-O—$C_{3-6}$heterocycloalkyl, aryl-O-aryl, and aryl-O-heteroaryl;

R5 is selected from the group consisting of $C_{1-6}$alkyl, halo$C_{1-6}$alkyl, O—$C_{1-6}$alkyl, $C_{3-6}$cycloalkyl, $C_{3-6}$heterocycloalkyl, aryl, heteroaryl, O-aryl, O-aryl-O—$C_{1-6}$alkyl, O-heteroaryl, O—$C_{3-6}$heterocycloalkyl, O-halo$C_{1-6}$alkyl, OH, CN, $NO_2$, $SF_6$, halogen and $COOR^i$;

n is an integer comprised from 0 to 2;

m is an integer comprised from 0 to 2;

$R^i$ is independently selected from the group consisting of hydrogen and $C_{1-6}$alkyl;

$R^{ii}$ is independently selected from the group consisting of hydrogen and $C_{1-6}$alkyl;

$R^{iv}$ and $R^v$ are independently selected from the group consisting of hydrogen, $C_{1-6}$alkyl and hydroxy$C_{1-6}$alkyl;

provided that:

a) when A is S, B is O, R1 and R2 are both $CH_3$, R3 and R4 are both hydrogen, C is not one of

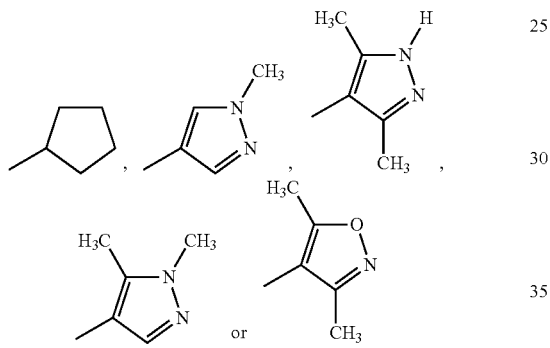

b) when A is S, B is O, R1 and R2 are respectively $CH_3$ and hydrogen, R3 and R4 are both hydrogen, C is not one of

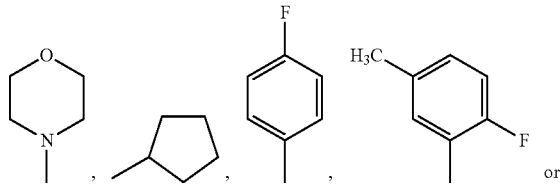

c) when A is S, B is O, R1 and R2 are respectively isopropyl and hydrogen, R3 and R4 are both hydrogen, C is not one of

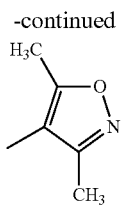

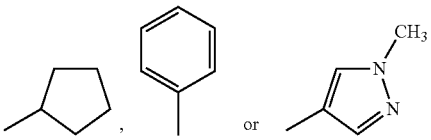

d) when A is S, B is O, R1 and R2 are both H, R3 and R4 are both hydrogen, C is not one of

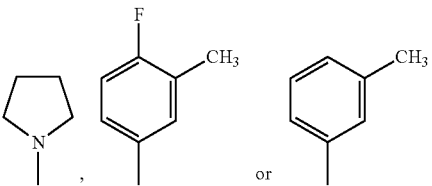

e) when A is S, B is O, R1 and R2 are respectively hydrogen and $CH_2CH_2OH$, R3 and R4 are both hydrogen, C is not phenyl.

2. The compound according to claim 1, wherein B is O.

3. The compound according to claim 1, wherein R1 and R2 are hydrogen.

4. The compound according to claim 1, wherein R3 and R4 are hydrogen.

5. The compound according to claim 1, wherein A is selected from the group consisting of S and $SO_2$.

6. The compound according to claim 1, wherein the compound is selected from the group consisting of:

| 002 | rac-3-[4-(1,2-dimethylimidazol-4-yl) sulfonylmorpholin-2-yl]benzothiophene-2-carboxamide |
| --- | --- |
| 003 | rac-3-[4-(benzenesulfonyl)morpholin-2-yl]benzothiophene-2-carboxamide |
| 004 | rac-3-[4-(1H-imidazol-4-ylsulfonyl)morpholin-2-yl]benzothiophene-2-carboxamide |
| 005 | rac-3-[4-(3-thienylsulfonyl)morpholin-2-yl]benzothiophene-2-carboxamide |
| 006 | rac-3-[4-(4-phenoxyphenyl)sulfonylmorpholin-2-yl]benzothiophene-2-carboxamide |
| 007 | rac-methyl 3-[2-(2-carbamoylbenzothiophen-3-yl)morpholin-4-yl] sulfonylbenzoate |
| 008 | rac-3-[4-(3,5-dimethylisoxazol-4-yl) sulfonylmorpholin-2-yl]benzothiophene-2-carboxamide |
| 009 | rac-3-[4-(3-bromophenyl)sulfonylmorpholin-2-yl]benzothiophene-2-carboxamide |
| 010 | rac-3-[4-(4-methoxyphenyl)sulfonylmorpholin-2-yl]benzothiophene-2-carboxamide |

-continued

| | |
|---|---|
| 011 | rac-3-[4-[4-(trifluoromethyl)phenyl] sulfonylmorpholin-2-yl]benzothiophene-2-carboxamide |
| 012 | rac-3-[4-(m-tolylsulfonyl)morpholin-2-yl]benzothiophene-2-carboxamide |
| 015 | rac-3-[4-[4-(2-oxopyrrolidin-1-yl)phenyl] sulfonylmorpholin-2-yl]benzothiophene-2-carboxamide |
| 016 | rac-3-[4-cyclohexylsulfonylmorpholin-2-yl]benzothiophene-2-carboxamide |
| 017 | rac-3-[4-(1,3-benzodioxol-5-ylsulfonyl)morpholin-2-yl]benzothiophene-2-carboxamide |
| 018 | rac-3-[(4-(2,3-dihydro-1,4-benzodioxin-6-ylsulfonyl)morpholin-2-yl]benzothiophene-2-carboxamide |
| 019 | rac-3-[4-[4-(4-methoxyphenoxy)phenyl] sulfonylmorpholin-2-yl]benzothiophene-2-carboxamide |
| 020 | rac-3-[4-(3-fluorophenyl)sulfonylmorpholin-2-yl]benzothiophene-2-carboxamide |
| 021 | rac-3-[4-(3,4-difluorophenyl)sulfonylmorpholin-2-yl]benzothiophene-2-carboxamide |
| 022 | rac-3-[4-(4-fluorophenyl)sulfonylmorpholin-2-yl]benzothiophene-2-carboxamide |
| 023 | rac-3-[4-(4-methoxy-3-methyl-phenyl) sulfonylmorpholin-2-yl]benzothiophene-2-carboxamide |
| 024 | rac-3-[4-[4-(4-pyridyloxy)phenyl]sulfonylmorpholin-2-yl]benzothiophene-2-carboxamide |
| 025 | rac-3-[4-(4-fluoro-3-methyl-phenyl) sulfonylmorpholin-2-yl]-N,N-dimethyl-benzothiophene-2-carboxamide |
| 026 | rac-3-[4-(3-fluoro-4-methyl-phenyl)sulfonylmorpholin-2-yl]benzothiophene-2-carboxamide |
| 027 | rac-3-[4-(5-fluoro-2-methyl-phenyl)sulfonylmorpholin -2-yl]benzothiophene-2-carboxamide |
| 028 | rac-3-[4-(4-fluoro-3-methyl-phenyl) sulfonylmorpholin-2-yl]-N-methyl-benzothiophene-2-carboxamide |
| 029 | rac-3-[4-(4-fluoro-3-methyl-phenyl)sulfonyl morpholin-2-yl]-N-(2-hydroxyethyl)benzothiophene-2-carboxamide |
| 030 | rac-N-ethyl-3-[4-(4-fluoro-3-methyl-phenyl)sulfonylmorpholin-2-yl]benzothiophene-2-carboxamide |
| 031 | rac-3-[4-(4-fluoro-3-methyl-phenyl) sulfonylmorpholin-2-yl]-N-isopropyl-benzothiophene-2-carboxamide |
| 032 | rac-3-[4-(2,4,6-trimethylphenyl)sulfonylmorpholin-2-yl]benzothiophene-2-carboxamide |
| 033 | rac-3-[4-(p-tolylsulfonyl)morpholin-2-yl] benzothiophene-2-carboxamide |
| 034 | rac-3-[4-[(2-methyl-1,3-benzoxazol-6-yl) sulfonyl]morpholin-2-yl]benzothiophene-2-carboxamide |
| 035 | rac-3-[4-[3-(trifluoromethyl)phenyl] sulfonylmorpholin-2-yl]benzothiophene-2-carboxamide |
| 036 | rac-3-[4-(4-tert-butylphenyl)sulfonylmorpholin-2-yl]benzothiophene-2-carboxamide |
| 037 | rac-3-[4-(4-cyanophenyl)sulfonylmorpholin-2-yl]benzothiophene-2-carboxamide |
| 038 | rac-3-[4-[4-fluoro-3-(trifluoromethyl)phenyl] sulfonylmorpholin-2-yl]benzothiophene-2-carboxamide |
| 039 | rac-3-[4-[4-(trifluoromethoxy)phenyl] sulfonylmorpholin-2-yl]benzothiophene-2-carboxamide |
| 040 | rac-3-[4-(4-chlorophenyl)sulfonylmorpholin-2-yl]benzothiophene-2-carboxamide |
| 041 | rac-3-[4-[3-fluoro-4-(trifluoromethyl)phenyl] sulfonylmorpholin-2-yl]benzothiophene-2-carboxamide |
| 042 | 3-[(R)-4-[4-(trifluoromethyl)phenyl] sulfonylmorpholin-2-yl]benzothiophene-2-carboxamide |
| 043 | 3-[(S)-4-[4-(trifluoromethyl)phenyl] sulfonylmorpholin-2-yl]benzothiophene-2-carboxamide |
| 044 | rac-3-[4-[3-methyl-4-(trifluoromethyl)phenyl] sulfonylmorpholin-2-yl]benzothiophene-2-carboxamide |
| 045 | rac-3-[4-[3-methoxy-4-(trifluoromethyl)phenyl] sulfonylmorpholin-2-yl]benzothiophene-2-carboxamide |
| 046 | rac-3-[4-[4-methoxy-3-(trifluoromethyl)phenyl] sulfonylmorpholin-2-yl]benzothiophene-2-carboxamide |
| 047 | rac-3-[4-(4-methoxy-3-nitro-phenyl) sulfonylmorpholin-2-yl]benzothiophene-2-carboxamide |
| 048 | rac-3-[4-(3-methoxyphenyl)sulfonylmorpholin-2-yl]benzothiophene-2-carboxamide |
| 049 | rac-3-[4-[3-(trifluoromethoxy)phenyl] sulfonylmorpholin-2-yl]benzothiophene-2-carboxamide |
| 050 | rac-3-[4-(2-methoxyphenyl)sulfonylmorpholin-2-yl]benzothiophene-2-carboxamide |
| 051 | rac-3-[4-(4-phenylphenyl)sulfonylmorpholin-2-yl]benzothiophene-2-carboxamide |
| 052 | rac-3-[4-(2-naphthylsulfonyl)morpholin-2-yl]benzothiophene-2-carboxamide |
| 053 | rac-3-[4-(3-fluoro-4-methoxy-phenyl) sulfonylmorpholin-2-yl]benzothiophene-2-carboxamide |

| | |
|---|---|
| 054 | rac-3-[4-(3,4-dimethoxyphenyl)sulfonylmorpholin-2-yl]benzothiophene-2-carboxamide |
| 055 | 3-[(S)-4-[3-fluoro-4-(trifluoromethyl)phenyl] sulfonylmorpholin-2-yl]benzothiophene-2-carboxamide |
| 056 | 3-[(R)-4-[3-fluoro-4-(trifluoromethyl)phenyl] sulfonylmorpholin-2-yl]benzothiophene-2-carboxamide |
| 057 | rac-3-[4-[(4-methyl-2,3-dihydro-1,4-benzoxazin-7-yl)sulfonyl]morpholin-2-yl]benzothiophene-2-carboxamide |
| 058 | rac-3-[4-tetrahydropyran-4-ylsulfonylmorpholin-2-yl]benzothiophene-2-carboxamide |
| 059 | rac-3-[4-(2-methoxyethylsulfonyl)morpholin-2-yl]benzothiophene-2-carboxamide |
| 060 | rac-3-[4-[4-(pentafluoro-lambda6-sulfanyl) phenyl]sulfonylmorpholin-2-yl]benzothiophene-2-carboxamide |
| 061 | rac-3-[4-butylsulfonylmorpholin-2-yl]benzothiophene-2-carboxamide |
| 062 | rac-3-[4-(3-cyanophenyl)sulfonylmorpholin-2-yl]benzothiophene-2-carboxamide |
| 063 | rac-methyl 4-[2-(2-carbamoylbenzothiophen-3-yl)morpholin-4-yl]sulfonylbenzoate |
| 064 | rac-tert-butyl 4-[2-(2-carbamoylbenzothiophen-3-yl)morpholin-4-yl]sulfonylpiperidine-1-carboxylate |
| 065 | rac-3-[4-(4-nitrophenyl)sulfonylmorpholin-2-yl] benzothiophene-2-carboxamide |
| 066 | rac-3-[4-[2-(trifluoromethyl)phenyl] sulfonylmorpholin-2-yl]benzothiophene-2-carboxamide |
| 067 | rac-3-[4-[2-(trifluoromethoxy)phenyl] sulfonylmorpholin-2-yl]benzothiophene-2-carboxamide |
| 068 | rac-3-[4-(4-hydroxyphenyl)sulfonylmorpholin-2-yl]benzothiophene-2-carboxamide |
| 069 | rac-3-[4-(4-isopropoxyphenyl)sulfonylmorpholin-2-yl]benzothiophene-2-carboxamide |
| 070 | 3-[(S)-4-[(2-methyl-1,3-benzoxazol-6-yl) sulfonyl]morpholin-2-yl]benzothiophene-2-carboxamide |
| 071 | 3-[(R)-4-[(2-methyl-1,3-benzoxazol-6-yl) sulfonyl]morpholin-2-yl]benzothiophene-2-carboxamide |
| 072 | 3-[(S)-4-(3-fluoro-4-methyl-phenyl) sulfonylmorpholin-2-yl]benzothiophene-2-carboxamide |
| 073 | 3-[(R)-4-(3-fluoro-4-methyl-phenyl) sulfonylmorpholin-2-yl]benzothiophene-2-carboxamide and |
| 074 | rac-1,1-dioxo-3-[4-[3-fluoro-4-(trifluoromethyl) phenyl]sulfonylmorpholin-2-yl]benzothiophene-2-carboxamide. |

7. A pharmaceutical composition comprising a compound of formula (Ia):

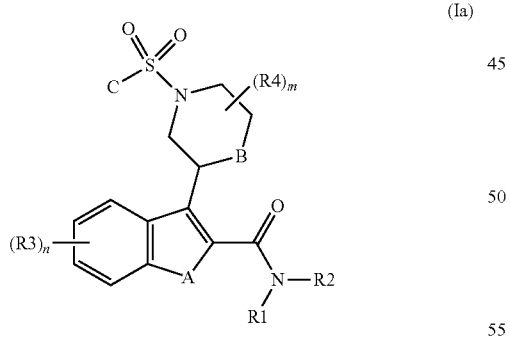

(Ia)

or pharmaceutically acceptable salts, hydrates, solvates, clathrates, polymorphs, stereoisomers thereof wherein:

R1 and R2 are independently selected from the group consisting of hydrogen, $C_{1-4}$alkyl, hydroxy$C_{1-4}$alkyl, and $C_{1-4}$alkyl-O—$C_{1-4}$alkyl;

R3 is selected from the group consisting of hydrogen, $C_{1-6}$alkyl, halo$C_{1-6}$alkyl, OH, O—$C_{1-6}$alkyl, $C_{1-6}$alkyl-O—$C_{1-6}$alkyl, CN, $NO_2$ and halogen;

R4 is independently selected from the group consisting of hydrogen, $C_{1-6}$alkyl, halo$C_{1-6}$ alkyl and halogen;

A is selected from the group consisting of S, SO, and $SO_2$;

B is selected from the group consisting of $CR^{iv}R^{v}$, O, and $NR^{ii}$;

C is selected from the group consisting of $C_{1-6}$alkyl, halo$C_{1-6}$alkyl, $C_{3-6}$cycloalkyl optionally substituted with one or more R5, $C_{3-6}$heterocycloalkyl optionally substituted with one or more R5, aryl optionally substituted with one or more R5, heteroaryl optionally substituted with one or more R5, $C_{1-6}$alkyl-O—$C_{1-6}$alkyl, $C_{1-6}$alkyl-O-aryl, $C_{1-6}$alkyl-O-heteroaryl, $C_{1-6}$alkyl-O—$C_{3-6}$heterocycloalkyl, aryl-O-aryl, and aryl-O-heteroaryl;

R5 is selected from the group consisting of $C_{1-6}$alkyl, halo$C_{1-6}$alkyl, O—$C_{1-6}$alkyl, $C_{3-6}$cycloalkyl, $C_{3-6}$heterocycloalkyl, aryl, heteroaryl, O-aryl, O-aryl-O—$C_{1-6}$alkyl, O-heteroaryl, O—$C_{3-6}$heterocycloalkyl, O-halo$C_{1-6}$alkyl, OH, CN, $NO_2$, $SF_6$, halogen and $COOR^{i}$;

n is an integer comprised from 0 to 2;

m is an integer comprised from 0 to 2;

$R^{i}$ is independently selected from the group consisting of hydrogen and $C_{1-6}$alkyl;

$R^{ii}$ is independently selected from the group consisting of hydrogen and $C_{1-6}$alkyl;

$R^{iv}$ and $R^{v}$ are independently selected from the group consisting of hydrogen, $C_{1-6}$alkyl and hydroxy$C_{1-6}$alkyl;

provided that:

a) when A is S, B is O, R1 and R2 are both $CH_3$, R3 and R4 are both hydrogen, C is not one of

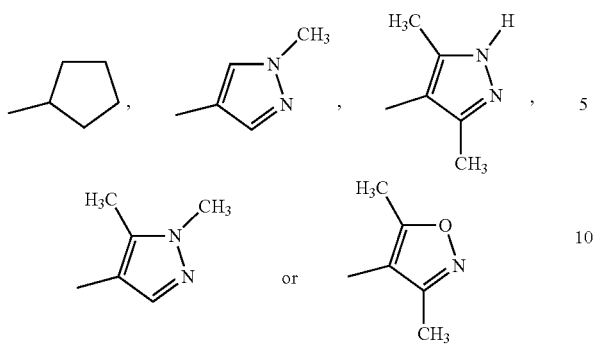

b) when A is S, B is O, R1 and R2 are respectively CH₃ and hydrogen, R3 and R4 are both hydrogen, C is not one of

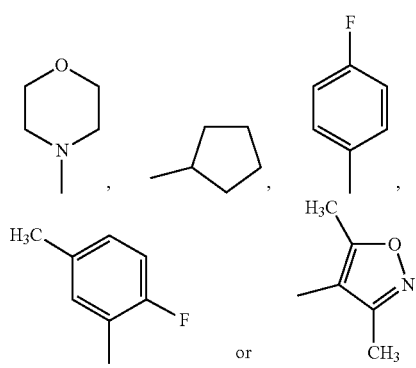

c) when A is S, B is O, R1 and R2 are respectively isopropyl and hydrogen, R3 and R4 are both hydrogen, C is not one of

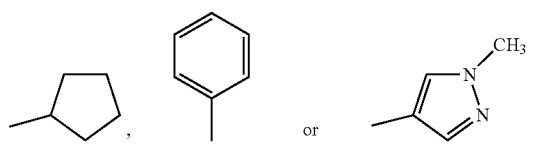

d) when A is S, B is O, R1 and R2 are both hydrogen, R3 and R4 are both hydrogen, C is not one of

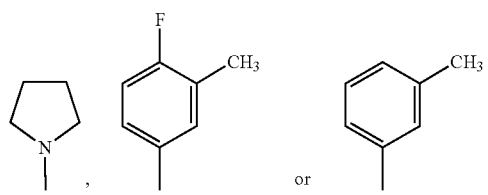

e) when A is S, B is O, R1 and R2 are respectively hydrogen and CH₂CH₂OH, R3 and R4 are both hydrogen, C is not phenyl;

and at least a pharmaceutically acceptable excipient.

8. A method for treating cystic fibrosis or modulating CFTR protein activities, the method comprising administering to a subject in need thereof a compound of formula (Ia)

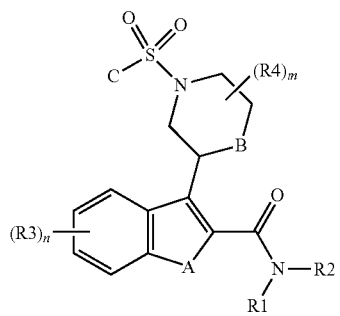

or pharmaceutically acceptable salts, hydrates, solvates, clathrates, polymorphs, stereoisomers thereof wherein:

R1 and R2 are independently selected from the group consisting of hydrogen, $C_{1-4}$alkyl, hydroxy$C_{1-4}$alkyl, and $C_{1-4}$alkyl-O—$C_{1-4}$alkyl;

R3 is selected from the group consisting of hydrogen, $C_{1-6}$alkyl, halo$C_{1-6}$alkyl, OH, O—$C_{1-6}$alkyl, $C_{1-6}$alkyl-O—$C_{1-6}$alkyl, CN, NO₂ and halogen;

R4 is independently selected from the group consisting of hydrogen, $C_{1-6}$alkyl, halo$C_{1-6}$ alkyl and halogen;

A is selected from the group consisting of S, SO, and SO₂;

B is selected from the group consisting of $CR^{iv}R^{v}$, O, and $NR^{ii}$;

C is selected from the group consisting of $C_{1-6}$alkyl, halo$C_{1-6}$alkyl, $C_{3-6}$cycloalky optionally substituted with one or more R5, $C_{3-6}$heterocycloalkyl optionally substituted with one or more R5, aryl optionally substituted with one or more R5, heteroaryl optionally substituted with one or more R5, $C_{1-6}$alkyl-O—$C_{1-6}$alkyl, $C_{1-6}$alkyl-O-aryl, $C_{1-6}$alkyl-O-heteroaryl, $C_{1-6}$alkyl-O—$C_{3-6}$heterocycloalkyl, aryl-O-aryl, and aryl-O-heteroaryl;

R5 is selected from the group consisting of $C_{1-6}$alkyl, halo$C_{1-6}$alkyl, O—$C_{1-6}$alkyl, $C_{3-6}$cycloalkyl, $C_{3-6}$heterocycloalkyl, aryl, heteroaryl, O-aryl, O-aryl-O—$C_{1-6}$alkyl, O-heteroaryl, O—$C_{3-6}$heterocycloalkyl, O-halo$C_{1-6}$alkyl, OH, CN, NO₂, SF₆, halogen and $COOR^{i}$;

n is an integer comprised from 0 to 2;

m is an integer comprised from 0 to 2;

$R^{i}$ is independently selected from the group consisting of hydrogen and $C_{1-6}$alkyl;

$R^{ii}$ is independently selected from the group consisting of hydrogen and $C_{1-6}$alkyl;

$R^{iv}$ and $R^{v}$ are independently selected from the group consisting of hydrogen, $C_{1-6}$alkyl and hydroxy$C_{1-6}$alkyl; provided that:

a) when A is S, B is O, R1 and R2 are both CH₃, R3 and R4 are both hydrogen, C is not one of

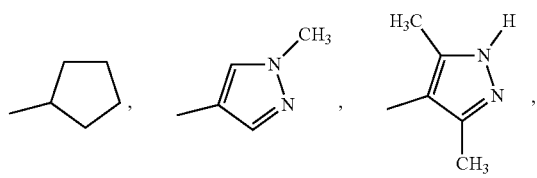

-continued

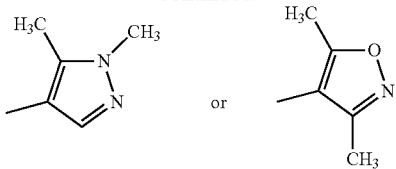

b) when A is S, B is O, R1 and R2 are respectively CH₃ and hydrogen, R3 and R4 are both hydrogen, C is not one of

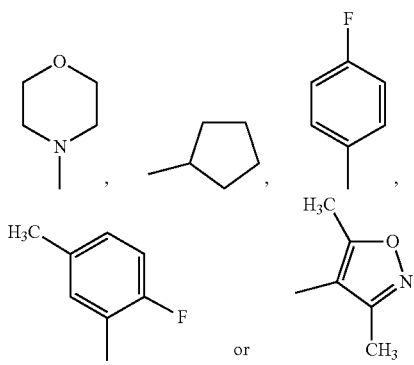

c) when A is S, B is O, R1 and R2 are respectively isopropyl and hydrogen, R3 and R4 are both hydrogen, C is not one of

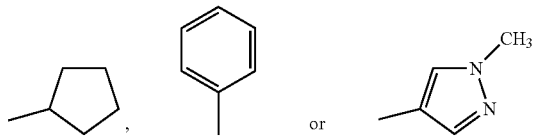

d) when A is S, B is O, R1 and R2 are both hydrogen, R3 and R4 are both hydrogen, C is not one of

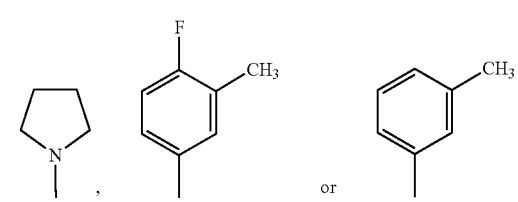

e) when A is S, B is O, R1 and R2 are respectively hydrogen and CH₂CH₂OH, R3 and R4 are both hydrogen, C is not phenyl.

9. The method according to claim 8, wherein the compound is selected from the group consisting of:

| | |
|---|---|
| 001 | rac-3-[4-(4-Fluoro-3-methyl-benzenesulfonyl)-morpholin-2-yl]-benzo[b]thiophene-2-carboxylic acid amide |
| 002 | rac-3-[4-(1,2-dimethylimidazol-4-yl) sulfonylmorpholin-2-yl]benzothiophene-2-carboxamide |
| 003 | rac-3-[4-(benzenesulfonyl)morpholin-2-yl]benzothiophene-2-carboxamide |
| 004 | rac-3-[4-(1H-imidazol-4-ylsulfonyl)morpholin-2-yl]benzothiophene-2-carboxamide |
| 005 | rac-3-[4-(3-thienylsulfonyl)morpholin-2-yl]benzothiophene-2-carboxamide |
| 006 | rac-3-[4-(4-phenoxyphenyl)sulfonylmorpholin-2-yl]benzothiophene-2-carboxamide |
| 007 | rac-methyl 3-[2-(2-carbamoylbenzothiophen-3-yl)morpholin-4-yl] sulfonylbenzoate |
| 008 | rac-3-[4-(3,5-dimethylisoxazol-4-yl) sulfonylmorpholin-2-yl]benzothiophene-2-carboxamide |
| 009 | rac-3-[4-(3-Bromophenyl)sulfonylmorpholin-2-yl]benzothiophene-2-carboxamide |
| 010 | rac-3-[4-(4-methoxyphenyl)sulfonylmorpholin-2-yl]benzothiophene-2-carboxamide |
| 011 | rac-3-[4-[4-(trifluoromethyl)phenyl] sulfonylmorpholin-2-yl]benzothiophene-2-carboxamide |
| 012 | rac-3-[4-(m-tolylsulfonyl)morpholin-2-yl]benzothiophene-2-carboxamide |
| 013 | 3-[(R)or (S)-4-(4-fluoro-3-methyl-phenyl) sulfonylmorpholin-2-yl]benzothiophene-2-carboxamide |
| 014 | 3-[(S)-4-(4-fluoro-3-methyl-phenyl) sulfonylmorpholin-2-yl]benzothiophene-2-carboxamide |
| 015 | rac-3-[4-[4-(2-oxopyrrolidin-1-yl)phenyl] sulfonylmorpholin-2-yl]benzothiophene-2-carboxamide |
| 016 | rac-3-[4-cyclohexylsulfonylmorpholin-2-yl]benzothiophene-2-carboxamide |
| 017 | rac-3-[4-(1,3-benzodioxol-5-ylsulfonyl)morpholin-2-yl]benzothiophene-2-carboxamide |
| 018 | rac-3-[(4-(2,3-dihydro-1,4-benzodioxin-6-ylsulfonyl)morpholin-2-yl]benzothiophene-2-carboxamide |
| 019 | rac-3-[4-[4-(4-methoxyphenoxy)phenyl] sulfonylmorpholin-2-yl]benzothiophene-2-carboxamide |
| 020 | rac-3-[4-(3-fluorophenyl)sulfonylmorpholin-2-yl]benzothiophene-2-carboxamide |
| 021 | rac-3-[4-(3,4-difluorophenyl)sulfonylmorpholin-2-yl]benzothiophene-2-carboxamide |
| 022 | rac-3-[4-(4-fluorophenyl)sulfonylmorpholin-2-yl]benzothiophene-2-carboxamide |
| 023 | rac-3-[4-(4-methoxy-3-methyl-phenyl) sulfonylmorpholin-2-yl]benzothiophene-2-carboxamide |
| 024 | rac-3-[4-[4-(4-pyridyloxy)phenyl] sulfonylmorpholin-2-yl]benzothiophene-2-carboxamide |

| | |
|---|---|
| 025 | rac-3-[4-(4-fluoro-3-methyl-phenyl) sulfonylmorpholin-2-yl]-N,N-dimethyl-benzothiophene-2-carboxamide |
| 026 | rac-3-[4-(3-fluoro-4-methyl-phenyl) sulfonylmorpholin-2-yl]benzothiophene-2-carboxamide |
| 027 | rac-3-[4-(5-fluoro-2-methyl-phenyl) sulfonylmorpholin-2-yl]benzothiophene-2-carboxamide |
| 028 | rac-3-[4-(4-fluoro-3-methyl-phenyl)sulfonylmorpholin -2-yl]-N-methyl-benzothiophene-2-carboxamide |
| 029 | rac-3-[4-(4-fluoro-3-methyl-phenyl) sulfonylmorpholin-2-yl]-N-(2-hydroxyethyl) benzothiophene-2-carboxamide |
| 030 | rac-N-ethyl-3-[4-(4-fluoro-3-methyl-phenyl) sulfonylmorpholin-2-yl]benzothiophene-2-carboxamide |
| 031 | rac-3-[4-(4-fluoro-3-methyl-phenyl) sulfonylmorpholin-2-yl]-N-isopropyl-benzothiophene-2-carboxamide |
| 032 | rac-3-[4-(2,4,6-trimethylphenyl)sulfonylmorpholin-2-yl]benzothiophene-2-carboxamide |
| 033 | rac-3-[4-(p-tolylsulfonyl)morpholin-2-yl]benzothiophene-2-carboxamide |
| 034 | rac-3-[4-[(2-methyl-1,3-benzoxazol-6-yl) sulfonyl]morpholin-2-yl]benzothiophene-2-carboxamide |
| 035 | rac-3-[4-[3-(trifluoromethyl)phenyl] sulfonylmorpholin-2-yl]benzothiophene-2-carboxamide |
| 036 | rac-3-[4-(4-tert-butylphenyl)sulfonylmorpholin-2-yl]benzothiophene-2-carboxamide |
| 037 | rac-3-[4-(4-cyanophenyl)sulfonylmorpholin-2-yl]benzothiophene-2-carboxamide |
| 038 | rac-3-[4-[4-fluoro-3-(trifluoromethyl)phenyl] sulfonylmorpholin-2-yl]benzothiophene-2-carboxamide |
| 039 | rac-3-[4-[4-(trifluoromethoxy)phenyl] sulfonylmorpholin-2-yl]benzothiophene-2-carboxamide |
| 040 | rac-3-[4-(4-chlorophenyl)sulfonylmorpholin-2-yl]benzothiophene-2-carboxamide |
| 041 | rac-3-[4-[3-fluoro-4-(trifluoromethyl)phenyl] sulfonylmorpholin-2-yl]benzothiophene-2-carboxamide |
| 042 | 3-[(R)-4-[4-(trifluoromethyl)phenyl] sulfonylmorpholin-2-yl]benzothiophene-2-carboxamide |
| 043 | 3-[(S)-4-[4-(trifluoromethyl)phenyl] sulfonylmorpholin-2-yl]benzothiophene-2-carboxamide |
| 044 | rac-3-[4-[3-methyl-4-(trifluoromethyl)phenyl] sulfonylmorpholin-2-yl]benzothiophene-2-carboxamide |
| 045 | rac-3-[4-[3-methoxy-4-(trifluoromethyl)phenyl] sulfonylmorpholin-2-yl]benzothiophene-2-carboxamide |
| 046 | rac-3-[4-[4-methoxy-3-(trifluoromethyl)phenyl] sulfonylmorpholin-2-yl]benzothiophene-2-carboxamide |
| 047 | rac-3-[4-(4-methoxy-3-nitro-phenyl) sulfonylmorpholin-2-yl]benzothiophene-2-carboxamide |
| 048 | rac-3-[4-(3-methoxyphenyl)sulfonylmorpholin-2-yl]benzothiophene-2-carboxamide |
| 049 | rac-3-[4-[3-(trifluoromethoxy)phenyl] sulfonylmorpholin-2-yl]benzothiophene-2-carboxamide |
| 050 | rac-3-[4-(2-methoxyphenyl)sulfonylmorpholin-2-yl]benzothiophene-2-carboxamide |
| 051 | rac-3-[4-(4-phenylphenyl)sulfonylmorpholin-2-yl]benzothiophene-2-carboxamide |
| 052 | rac-3-[4-(2-naphthylsulfonyl)morpholin-2-yl]benzothiophene-2-carboxamide |
| 053 | rac-3-[4-(3-fluoro-4-methoxy-phenyl) sulfonylmorpholin-2-yl]benzothiophene-2-carboxamide |
| 054 | rac-3-[4-(3,4-dimethoxyphenyl)sulfonylmorpholin-2-yl]benzothiophene-2-carboxamide |
| 055 | 3-[(S)-4-[3-fluoro-4-(trifluoromethyl) phenyl]sulfonylmorpholin-2-yl]benzothiophene-2-carboxamide |
| 056 | 3-[(R)-4-[3-fluoro-4-(trifluoromethyl) phenyl]sulfonylmorpholin-2-yl]benzothiophene-2-carboxamide |
| 057 | rac-3-[4-[(4-methyl-2,3-dihydro-1,4-benzoxazin-7-yl)sulfonyl]morpholin-2-yl]benzothiophene-2-carboxamide |
| 058 | rac-3-[4-tetrahydropyran-4-ylsulfonylmorpholin-2-yl]benzothiophene-2-carboxamide |
| 059 | rac-3-[4-(2-methoxyethylsulfonyl)morpholin-2-yl]benzothiophene-2-carboxamide |
| 060 | rac-3-[4-[4-(pentafluoro-lambda6-sulfanyl) phenyl] sulfonylmorpholin-2-yl]benzothiophene-2-carboxamide |
| 061 | rac-3-[4-butylsulfonylmorpholin-2-yl]benzothiophene-2-carboxamide |
| 062 | rac-3-[4-(3-cyanophenyl)sulfonylmorpholin-2-yl]benzothiophene-2-carboxamide |
| 063 | rac-methyl 4-[2-(2-carbamoylbenzothiophen-3-yl)morpholin-4-yl]sulfonylbenzoate |
| 064 | rac-tert-butyl 4-[2-(2-carbamoylbenzothiophen-3-yl)morpholin-4-yl]sulfonylpiperidine-1-carboxylate |
| 065 | rac-3-[4-(4-nitrophenyl)sulfonylmorpholin-2-yl] benzothiophene-2-carboxamide |

| | |
|---|---|
| 066 | rac-3-[4-[2-(trifluoromethyl)phenyl] sulfonylmorpholin-2-yl]benzothiophene-2-carboxamide |
| 067 | rac-3-[4-[2-(trifluoromethoxy)phenyl] sulfonylmorpholin-2-yl]benzothiophene-2-carboxamide |
| 068 | rac-3-[4-(4-hydroxyphenyl)sulfonylmorpholin-2-yl]benzothiophene-2-carboxamide |
| 069 | rac-3-[4-(4-isopropoxyphenyl)sulfonylmorpholin-2-yl]benzothiophene-2-carboxamide |
| 070 | 3-[(S)-4-[(2-methyl-1,3-benzoxazol-6-yl) sulfonyl]morpholin-2-yl]benzothiophene-2-carboxamide |
| 071 | 3-[(R)-4-[(2-methyl-1,3-benzoxazol-6-yl) sulfonyl]morpholin-2-yl]benzothiophene-2-carboxamide |
| 072 | 3-[(S)-4-(3-fluoro-4-methyl-phenyl) sulfonylmorpholin-2-yl]benzothiophene-2-carboxamide |
| 073 | 3-[(R)-4-(3-fluoro-4-methyl-phenyl) sulfonylmorpholin-2-yl]benzothiophene-2-carboxamide |
| 074 | rac-1,1-dioxo-3-[4-[3-fluoro-4-(trifluoromethyl) phenyl]sulfonylmorpholin-2-yl]benzothiophene-2-carboxamide |
| 075 | 3-[4-(3,5-dimethyl-isoxazole-4-sulfonyl)-morpholin-2-yl]-benzo[b]thiophene-2-carboxylic acid methylamide |
| 076 | 3-[4-(1-methyl-1H-pyrazole-4-sulfonyl)-morpholin-2-yl]-benzo[b]thiophene-2-carboxylic acid isopropylamide |
| 077 | 3-[4-(cyclopentylsulfonyl)-2-morpholinyl]-N-isopropyl-1-benzothiophene-2-carboxamide |
| 078 | 3-[4-(cyclopentylsulfonyl)-2-morpholinyl]-N,N-dimethyl-1-benzothiophene-2-carboxamide |
| 079 | 3-{4-[(1,5-dimethyl-1H-pyrazol-4-yl)sulfonyl]-2-morpholinyl}-N,N-dimethyl-1-benzothiophene-2-carboxamide |
| 080 | N-(2-hydroxyethyl)-3-[4-(phenylsulfonyl)-2-morpholinyl]-1-benzothiophene-2-carboxamide |
| 081 | 3-(4-cyclopentanesulfonyl-morpholin-2-yl)-benzo[b]thiophene-2-carboxylic acid methylamide |
| 082 | 3-{4-[(2-fluoro-5-methylphenyl)sulfonyl]-2-morpholinyl}-N-methyl-1 -benzothiophene-2-carboxamide |
| 083 | 3-{4-[(3,5-dimethyl-1H-pyrazol-4-yl)sulfonyl]-2-morpholinyl}-N,N-dimethyl-1-benzothiophene-2-carboxamide |
| 084 | 3-(4-cyclopentylsulfonylmorpholin-2-yl)benzothiophene-2-carboxamide |
| 085 | N-methyl-3-(4-morpholinosulfonylmorpholin-2-yl)benzothiophene-2-carboxamide |
| 087 | 3-[4-(benzenesulfonyl)morpholin-2-yl]-N-isopropyl-benzothiophene-2-carboxamide |
| 088 | 3-[4-(4-fluorophenyl)sulfonylmorpholin-2-yl]-N-methyl-benzothiophene-2-carboxamide |
| 089 | N,N-dimethyl-3-[4-(1-methyipyrazol-4-yl) sulfonylmorpholin-2-yl]benzothiophene-2-carboxamide and |
| 090 | 3-[4-(3,5-dimethylisoxazol-4-yl)sulfonylmorpholin-2-yl]-N,N-dimethyl-benzothiophene-2-carboxamide. |

\* \* \* \* \*